United States Patent
Urata et al.

[11] Patent Number: 5,910,600
[45] Date of Patent: Jun. 8, 1999

[54] BISPHOSPHITE COMPOUND, PROCESS FOR ITS PRODUCTION AND HYDROFORMYLATION PROCESS EMPLOYING THE BISPHOSPHITE COMPOUND

[75] Inventors: Hisao Urata; Hiroaki Itagaki; Eitaro Takahashi; Yasuhiro Wada; Yoshiyuki Tanaka, all of Yokohama; Yasukazu Ogino, Kurashiki, all of Japan

[73] Assignee: Mitsubishi Chemical Corporation, Tokyo, Japan

[21] Appl. No.: 08/845,835

[22] Filed: Apr. 28, 1997

[30] Foreign Application Priority Data

Apr. 30, 1996 [JP] Japan .................................. 8-109185
Apr. 30, 1996 [JP] Japan .................................. 8-109186

[51] Int. Cl.[6] .............................. C07F 9/12; C07C 45/50
[52] U.S. Cl. ..................... 558/162; 544/243; 544/244; 544/337; 546/23; 546/25; 548/114; 549/220; 568/429; 568/444; 568/451
[58] Field of Search ............................. 558/162; 568/451

[56] References Cited

U.S. PATENT DOCUMENTS

| | | | |
|---|---|---|---|
| 3,287,449 | 11/1966 | Baranaukas et al. | 558/156 X |
| 3,694,485 | 9/1972 | Drinkard, Jr. et al. | 558/335 |
| 5,663,369 | 9/1997 | Kreutzer et al. | 549/212 |
| 5,696,280 | 12/1997 | Shapiro | 558/140 |

FOREIGN PATENT DOCUMENTS

96/11182  4/1996  WIPO .
96/22968  8/1996  WIPO .

OTHER PUBLICATIONS

Database MARPAT on STN®, Chemical Abstracts Service, (Columbus, Ohio), Accession No. 127:294939, PCT International Application WO 97/33854, Sep. 1997, abstract.

Database MARPAT on STN®, Chemical Abstracts Service, (Columbus, Ohio), Accession No. 127:96824, PCT International Application WO 97/20801, Jun. 1997, abstract.

*Primary Examiner*—Michael G. Ambrose
*Attorney, Agent, or Firm*—Oblon, Spivak, McClelland, Maier & Neustadt, P.C.

[57] ABSTRACT

A bisphosphite compound of the following formula (A):

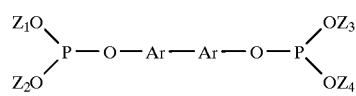

(A)

wherein —Ar—Ar— is a bisarylene group represented by any one of the formulae (A-I) to (A-III) defined in the specification, and each of $Z_1$ to $Z_4$ is a $C_{4-20}$ aromatic or heteroaromatic group which may have a substituent, wherein each of substituents on carbon atoms of an aromatic ring adjacent to the carbon atom bonded to the oxygen atom in each of $Z_1$ to $Z_4$, is a $C_{0-2}$ group, and each pair of $Z_1$ and $Z_2$, and $Z_3$ and $Z_4$, are not bonded to each other.

15 Claims, No Drawings

BISPHOSPHITE COMPOUND, PROCESS FOR ITS PRODUCTION AND HYDROFORMYLATION PROCESS EMPLOYING THE BISPHOSPHITE COMPOUND

BACKGROUND OF THE INVENTION

1. Field of the Invention

The present invention relates to a novel bisphosphite compound, a process for its production, and a process for hydroformylation of an olefinic compound employing the bisphosphite compound.

2. Discussion of Background

A process which comprises reacting an olefinic compound with water gas in the presence of a catalyst to produce aldehydes or alcohols as their hydrogenated products, is well-known as a hydroformylation process. As a catalyst for the hydroformylation reaction, it is common to use a soluble complex of an element selected from Groups 8 to 10 of the Periodic Table (hereinafter referred to as a "Group VIII metal") having an organic phosphorus compound as a ligand. In general, the ligand used together with the metal component of the catalyst gives a substantial influence to the catalytic reaction. Also in the hydroformylation reaction, it is well known that the catalytic activity and the selectivity are substantially influenced by the ligand. In order to carry out the hydroformylation reaction industrially advantageously, it is important to improve the catalytic activity and selectivity. Accordingly, various efforts to design the ligand have been made for this purpose.

Various phosphite compounds are known as a group of phosphorus compounds which may be used as the ligands for the hydroformylation reaction. In addition to simple monophosphites such as trialkyl phosphites or triarylphosphites, various phosphite compounds such as polyphosphites having a plurality of coordinating phosphorus atoms in their molecules, have been proposed. For example, JP-A-62-116587 discloses a bisphosphite compound wherein one of the two phosphite groups has a cyclic structure, and JP-A-6-184036 discloses a bisphosphite compound wherein both of the two phosphite groups have cyclic structures.

On the other hand, JP-A-5-178779 discloses a bisphosphite compound in which both of the two phosphite groups are not cyclized. In the bisphosphite compound, substituents on the bisarylene group as the crosslinking moiety are not particularly specified. As the four ester terminal groups, phenyl groups having a hydrocarbon substituent at least at the o-position, or β-naphthyl groups having a hydrocarbon substituent at least at the 3-position, are used. As the hydrocarbon substituent, a bulky organic group having at least three carbon atoms such as an isopropyl group or a tertiary butyl group, is used.

As mentioned above, various phosphite compounds have been proposed as the ligands to be used for the hydroformylation reaction. However, in the hydroformylation reactions using bisphosphite compounds so far reported, the selectivity for linear aldehydes as the desired products tended to be inadequate when a high reaction rate was obtained. Reversely, the reaction rate tended to be inadequate when high selectivity for linear aldehyde was obtained.

In JP-A-6-184036 and JP-A-5-178779, the above-mentioned bisphosphite compounds are synthesized by reacting a bisarylene diol with a bisarylene chlorophosphite or a bisaryl chlorophosphite in a solvent in the presence of a nitrogen-containing base such as pyridine or triethylamine, where hydrogen chloride produced as a by-product as the reaction proceeds is captured by a nitrogen-containing base.

However, when the present inventors have attempted to prepare a group of bisphosphite compounds having bulky groups as represented by the following formulae (I) to (III), by the above method, it has been found that a monophosphite is preferentially formed, and yield of a bisphosphite compound is virtually 0.

As described in the foregoing, various phosphite compounds have been proposed as the ligands to be used for the hydroformylation reaction. However, in the hydroformylation reactions using such compounds, a high reaction rate and high selectivity for the desired product have not simultaneously been satisfied. Accordingly, there has been a concern that in commercial production, the economical efficiency will be low, and there has been a problem that such compounds are hardly useful as industrial catalysts. Therefore, it has been desired to develop a bisphosphite compound which is capable of presenting excellent selectivity for the desired product while maintaining a high reaction rate and to develop an efficient process to produce such a bisphosphite compound.

SUMMARY OF THE INVENTION

In the course of a search for a ligand effective for improving and maintaining the catalytic activity and the selectivity for the desired product in the hydroformylation reaction, the present inventors have found a novel bisphosphite compound having a certain specific structure. Further, as a process for producing such a bisphosphite compound, a specific control has been found to be effective for the reaction of chlorophosphite with a metal salt converted from the starting material diol. It has been found that by this process, it is possible to obtain a novel bisphosphite compound which has not been synthesized heretofore, and by using such a phosphite compound as one component of the catalyst for the hydroformylation reaction, i.e. as a ligand used in combination with a metal component of the catalyst, the reaction can proceed at a high speed, and excellent selectivity for the desired product. The present invention has been accomplished on the basis of these discoveries.

That is, in a first aspect, the present invention provides a bisphosphite compound of the following formula (A):

(A)

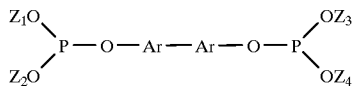

wherein —Ar—Ar— is a bisarylene group represented by any one of the following formulae (A-I) to (A-III), and each of $Z_1$ to $Z_4$ is a $C_{4-20}$ aromatic or heteroaromatic group which may have a substituent, wherein each of substituents on carbon atoms of an aromatic ring adjacent to the carbon atom bonded to the oxygen atom in each of $Z_1$ to $Z_4$, is a $C_{0-2}$ group, and each pair of $Z_1$ and $Z_2$, and $Z_3$ and $Z_4$, are not bonded to each other,

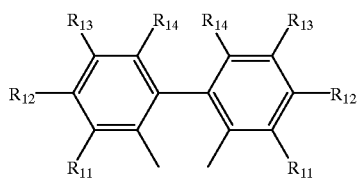
(A-I)

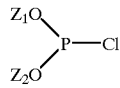
(B-I)

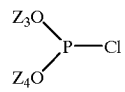
(B-II)

wherein each $R_{11}$ which is independent of the other $R_{11}$, is a $C_{3-20}$ alkyl or cycloalkyl group, and each of $R_{12}$ to $R_{14}$ which are independent of one another, is a hydrogen atom, a $C_{1-20}$ alkyl, alkoxy, cycloalkyl, cycloalkoxy, dialkylamino, aryl, aryloxy, alkylaryl, alkylaryloxy, arylalkyl or arylalkoxy group, a cyano group, a hydroxyl group or a halogen atom, wherein $Z_1$ to $Z_4$ are as defined in the above formula (A), at a temperature of at most 20° C. for at least one minute.

Further, in a third aspect, the present invention provides a hydroformylation process for producing aldehydes, which comprises reacting an olefinic compound with carbon monoxide and hydrogen in the presence of a Group VIII metal compound, wherein the reaction is carried out in the presence of a bisphosphite compound of the above formula (A).

DETAILED DESCRIPTION OF THE PREFERRED EMBODIMENTS

Now, the present invention will be described in detail with reference to the preferred embodiments.

The novel bisphosphite compound of the present invention is more specifically represented by the following formulae (I) to (III):

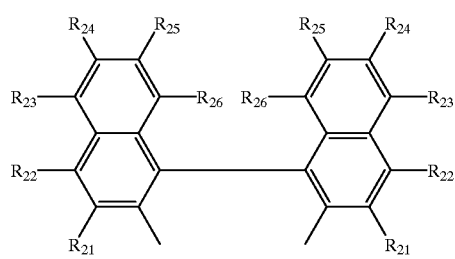
(A-II)

wherein each $R_{21}$ which is independent of the other $R_{21}$, is the same as $R_{11}$ in the formula (A-I), and each of $R_{22}$ to $R_{26}$ which are independent of one another, is the same as $R_{12}$ to $R_{14}$ in the formula (A-I),

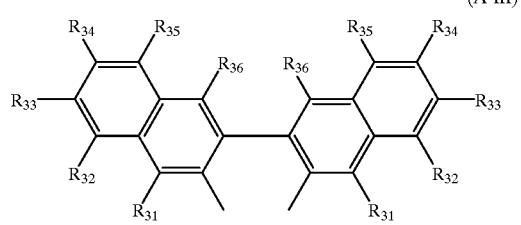
(A-III)

wherein each $R_{31}$ which is independent of the other $R_{31}$, is the same as $R_{11}$ in the formula (A-I), and each of $R_{32}$ to $R_{36}$ which are independent of one another, is the same as $R_{12}$ to $R_{14}$ in the formula (A-I).

In a second aspect, the present invention provides a process for producing the bisphosphite compound of the above formula (A), which comprises a step of contacting a compound of the following formula (B):

MO—Ar—Ar—OM (B)

wherein —Ar—Ar— is a bisarylene group represented by any one of the above formulae (A-I) to (A-III), and M is an alkali metal or an alkaline earth metal, with a phosphorus compound of the following formula (B-I) and/or (B-II):

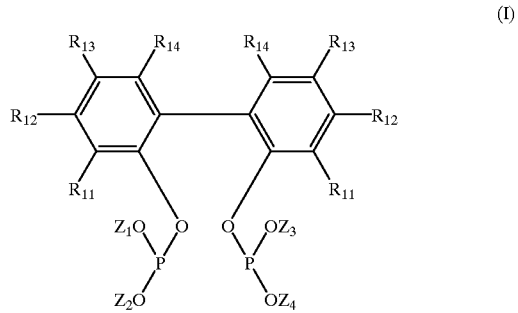
(I)

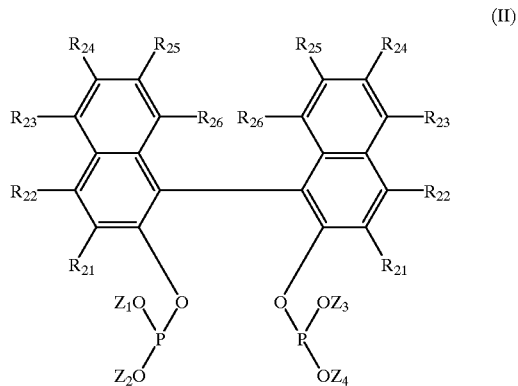
(II)

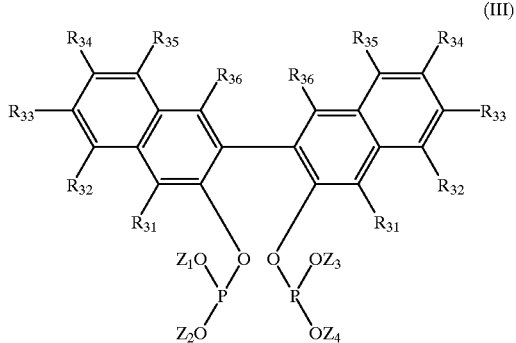

(III)

In the above formulae (I) to (III), each of $R_{11}$, $R_{21}$ and $R_{31}$ represents a $C_{3-20}$ linear or branched alkyl group such as a n-propyl group, an i-propyl group, a s-butyl group, a at-butyl group, an isopentyl group, a neopentyl group, a t-pentyl group or a t-hexyl group, preferably a $C_{4-20}$ alkyl group, more preferably a $C_{4-10}$ alkyl group. Further, preferred is an alkyl group wherein the carbon atom bonded to the aromatic ring is tertiary, such as a t-butyl group, a t-pentyl group or a t-hexyl group. Further, each of $R_{11}$, $R_{21}$ and $R_{31}$ also represents a $C_{6-14}$, preferably $C_{6-10}$, cycloalkyl group such as a cyclohexyl group, a cyclooctyl group or an adamantyl group.

Each of $R_{12}$ to $R_{14}$ of the formula (I), $R_{22}$ to $R_{26}$ of the formula (II) and $R_{32}$ to $R_{36}$ of the formula (III) may be a hydrogen atom, a $C_{1-20}$ linear or cyclic alkyl group such as a methyl group, an ethyl group, a n-propyl group, an i-propyl group, a n-butyl group, a s-butyl group, a t-butyl group, a n-pentyl group, an isopentyl group, a neopentyl group, a t-pentyl group, a t-hexyl group, a cyclohexyl group, a cyclooctyl group or an adamantyl group, an aryl group such as a phenyl group or a naphthyl group, a $C_{1-12}$ alkoxy group such as a methoxy group, an ethoxy group, an isopropoxy group or a t-butoxy group, a dialkylamino group such as a dimethylamino group or a diethylamino group, an aryloxy group such as a phenoxy group or a naphthoxy group, an arylalkyl group such as a benzyl group, an alkylaryl group such as a p-tolyl group or an o-tolyl group, a cycloalkoxy group such as a cyclopentyloxy group, an alkylaryloxy group such as a 2,3-xyxlenoxy group, an arylalkoxy group such as a 2-(2-naphthyl)ethoxy group, a cyano group, a hydroxyl group, or a halogen atom such as fluorine atom, a chlorine atom or a bromine atom. They may be the same or different.

Preferred as the bisarylene group in the formulae (I) to (III) may, for example, be a 3,3'-di-t-butyl-5,5'-dimethyl-1,1'-biphenyl-2,2'-diyl group, a 3,3',5,5'-tetra-t-butyl-1,1'-biphenyl-2,2'-diyl group, a 3,3',5,5'-tetra-t-butyl-6,6'-dimethyl-1,1'-biphenyl-2,2'-diyl group, a 3,3',5,5'-tetra-t-pentyl-1,1'-biphenyl-2,2'-diyl group, a 3,3',5,5'-tetra-t-hexyl-1,1'-biphenyl-2,2'-diyl group, a 3,3'-di-t-butyl-5,5'-dimethoxy-1,1'-biphenyl-2,2'-diyl group, a 3,3'-di-t-butyl-5,5'-diethoxy-1,1'-biphenyl-2,2'-diyl group, a 3,3'-di-t-butyl-5,5'-di-t-butoxy-1,1'-biphenyl-2,2'-diyl group, a 3,3',5,5'-tetra(cyclooctyl)-1,1'-biphenyl-2,2'-diyl group, a 3,3',6,6'-tetra-t-butyl-1,1'-binaphthyl-2,2'-diyl group, or a 1,1',7,7'-tetra-t-butyl-3,3'-binaphthyl-2,2'-diyl group.

In the formulae (I) to (III), each of $Z_1$ to $Z_4$ which may be the same or different, is a $C_{4-20}$ aromatic or heteroaromatic group which may have a substituent, wherein each pair of $Z_1$ and $Z_2$, and $Z_3$ and $Z_4$, are not bonded to each other.

Each of substituents on carbon atoms of an aromatic ring or a heteroaromatic ring adjacent to the carbon atom bonded to the phosphite oxygen atom in each of $Z_1$ to $Z_4$, is selected from the group consisting of $C_{0-2}$ groups such as a methyl group, an ethyl group, a trifluoromethyl group, a cyano group, a nitro group and halogen atoms such as a chlorine atom and a fluorine atom.

Substituents at other positions in each of $Z_1$ to $Z_4$ may, for example, be a $C_{1-12}$, preferably $C_{1-8}$, linear or branched alkyl group such as a methyl group, an ethyl group, a n-propyl group, an i-propyl group, a n-butyl group, a s-butyl group, a t-butyl group, a n-pentyl group, an isopentyl group, a neopentyl group or a t-pentyl group, a $C_{1-12}$, preferably $C_{1-8}$, linear or branched perfluoroalkyl group such as a trifluoromethyl group, a pentafluoroethyl group, a perfluoropropyl group or a perfluorobutyl group, a $C_{1-12}$, preferably $C_{1-8}$, alkoxy group such as a methoxy group or an ethoxy group, a $C_{6-18}$, preferably $C_{6-10}$, aryl group such as a phenyl group, a pentafluorophenyl group or a naphthyl group, a halogen atom, a cyano group, a nitro group, a hydroxyl group, an amino group, an acyl group, a carbonyloxy group, an oxycarbonyl group, an iminocarbonyl group, a sulfonyl group, a sulfinyl group, a silyl group or a thionyl group. From 1 to 5 such substituents may be substituted on each of $Z_1$ to $Z_4$.

Preferred as an aromatic group for $Z_1$ to $Z_4$ may, for example, be a phenyl group, a 1-naphthyl group, a 2-naphthyl group, a p-trifluoromethylphenyl group, a 2-ethylphenyl group, a 2-methylphenyl group, a 3-methylphenyl group, a 4-methylphenyl group, a 2,3-dimethylphenyl group, a 2,4-dimethylphenyl group, a 2,5-dimethylphenyl group, a 3,4-dimethylphenyl group, a 3,5-dimethylphenyl group, a 2-chlorophenyl group, a 3-chlorophenyl group, a 4-chlorophenyl group, a 2,3-dichlorophenyl group, a 2,4-dichlorophenyl group, a 2,5-dichlorophenyl group, a 3,4-dichlorophenyl group, a 3,5-dichlorophenyl group, a 2-methoxyphenyl group, a 3-methoxyphenyl group, a 4-methoxyphenyl group, a 2,3-dimethoxyphenyl group, a 3,4-dimethoxyphenyl group, a 3,5-dimethoxyphenyl group, a 4-cyanophenyl group, a 4-nitrophenyl group, a 4-phenylphenyl group, a 5,6,7,8-tetrahydro-1-naphthyl group, a 5,6,7,8-tetrahydro-2-naphthyl group, a 2-methyl-1-naphthyl group, a 4-chloro-1-naphthyl group, a 2-nitro-1-naphthyl group, or a 7-methoxy-2-naphthyl group.

Preferred as a heteroaromatic group for $Z_1$ to $Z_4$ may, for example, be a 2-pyridyl group, a 3-pyridyl group, a 4-pyridyl group, a 4-methyl-2-pyridyl group, a 6-methyl-2-pyridyl group, a 3-nitro-2-pyridyl group, a 2-pyrazyl group, a 4-pyrimidyl group, a 4-methyl-2-pyrimidyl group, a 4-benzofuryl group, a 5-benzofuryl group, a 5-benzothienyl group, a 2-quinolyl group, a 4-quinolyl group, a 6-quinolyl group, a 8-quinolyl group, a 5-nitro-8-quinolyl group, a 1-isoquinolyl group, a 3-isoquinolyl group, a 5-isoquinolyl group, a 2-quinoxalyl group, a 8-quinaldyl group, a 4-quinazolyl group, a 1-methyl-2-benzimidazolyl group, a 2-benzothiazolyl group, an N-methyl-2-carbazolyl group, a 2-benzofuranyl group, an N-methyl-4-indolyl group, an N-methyl-5-indolyl group, or a 4-methoxy-9-acridinyl group.

Now, examples of the bisphosphite compounds of the above formulae (I) to (III) will be shown below. In the following formulae, the following symbols have the following meanings.

Me or ——: methyl group
⁄: ethyl group
—⟨: t-butyl group
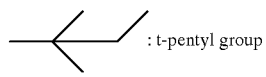: t-pentyl group
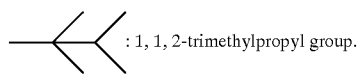: 1, 1, 2-trimethylpropyl group.
(1)
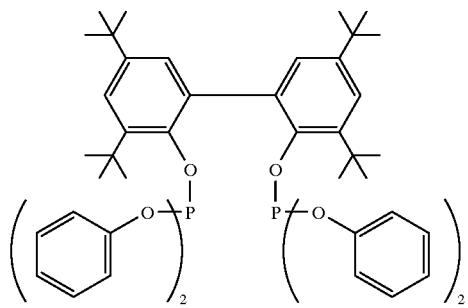
(2)
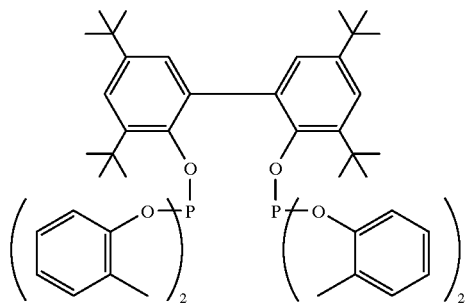
(3)
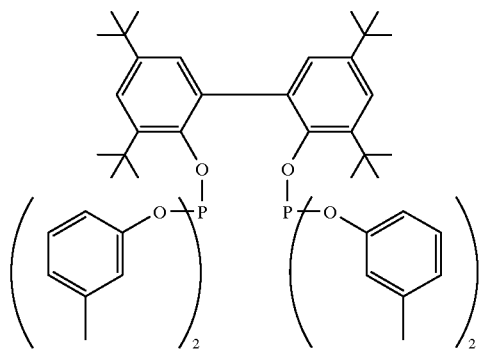
(4)
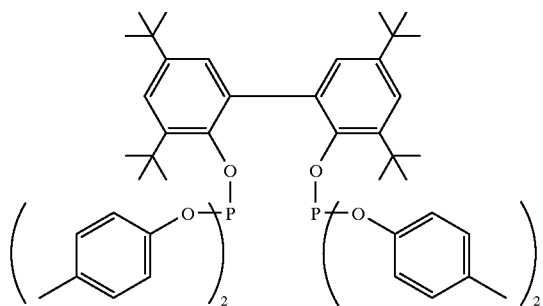

-continued
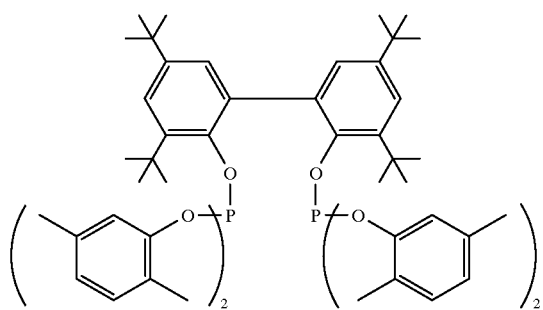
(5)
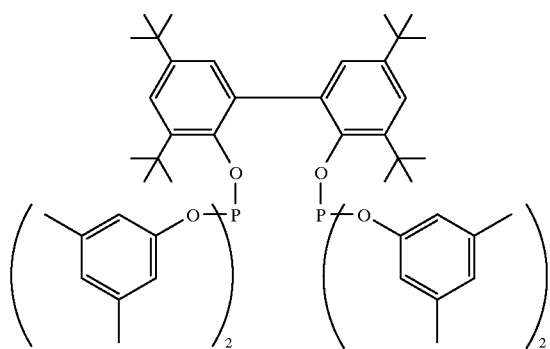
(6)
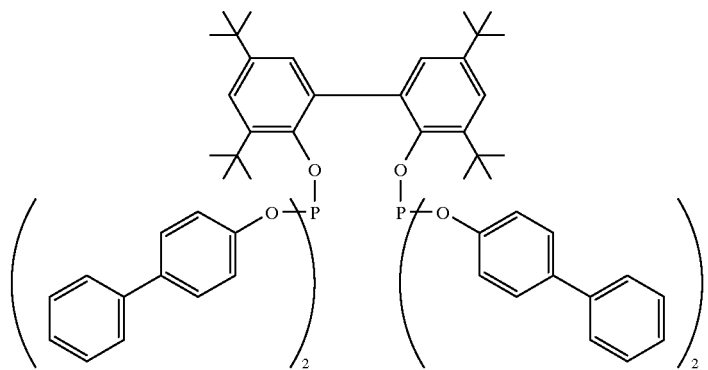
(7)
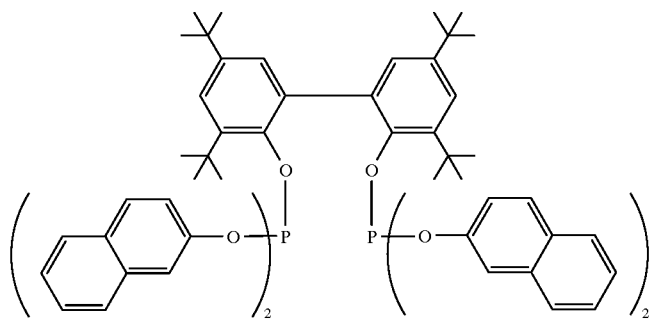
(8)

(9)
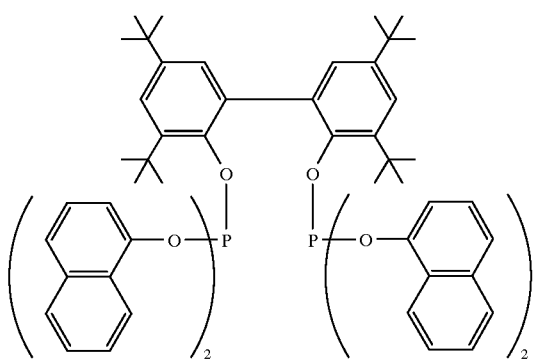
(10)
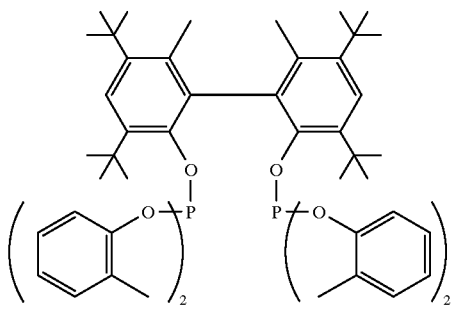
(11)
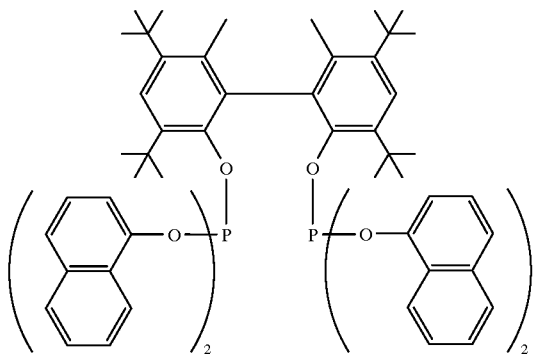
(12)
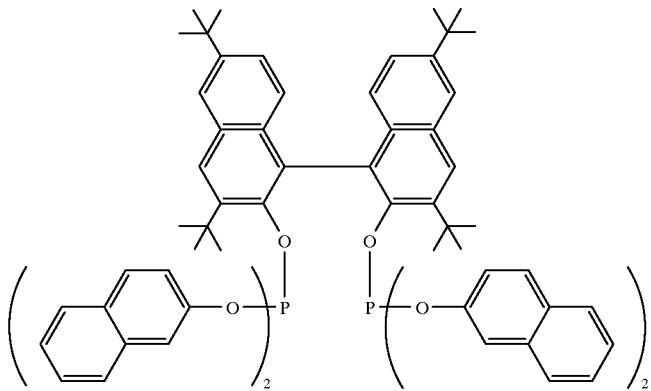

-continued
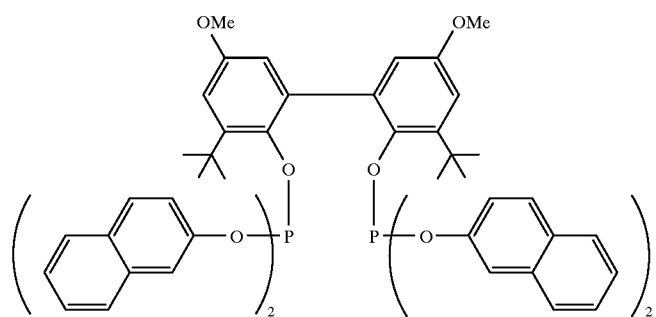
(13)
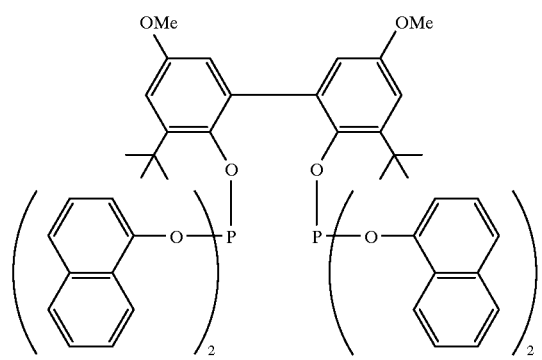
(14)
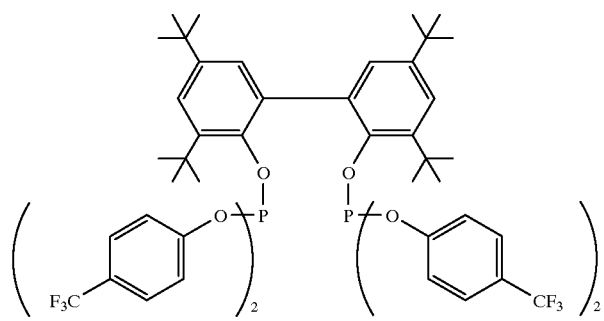
(15)
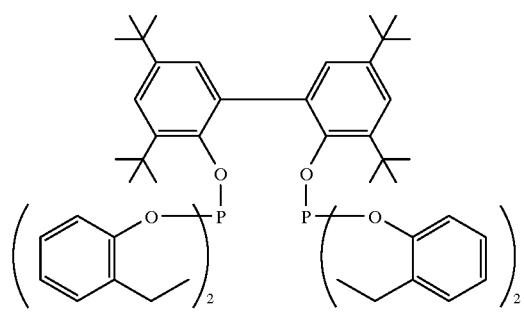
(16)

-continued
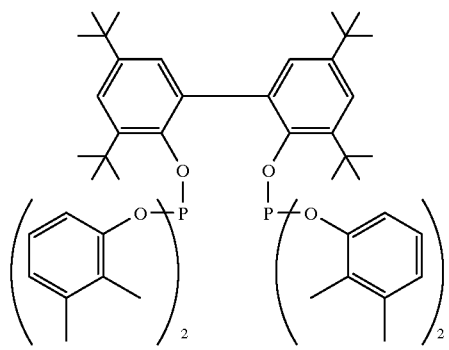
(17)
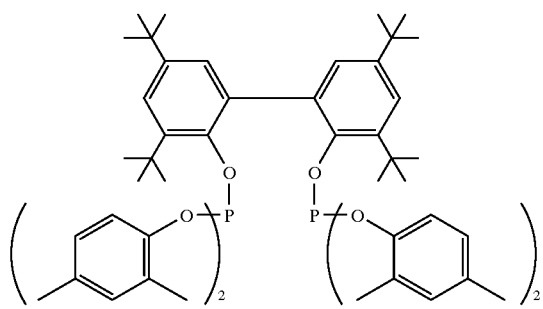
(18)
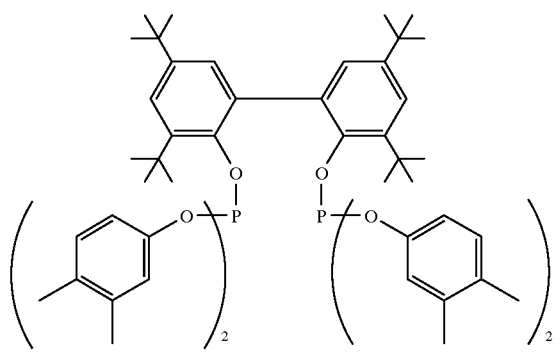
(19)
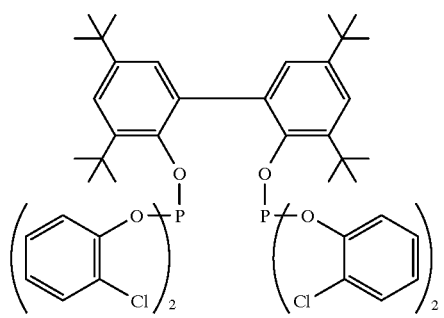
(20)

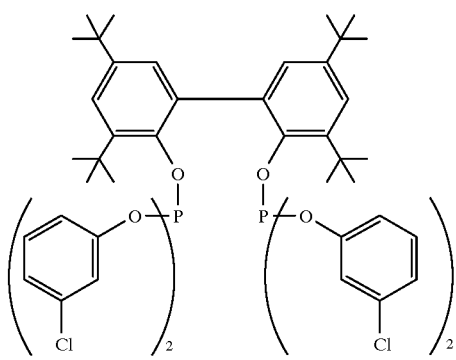
(21)
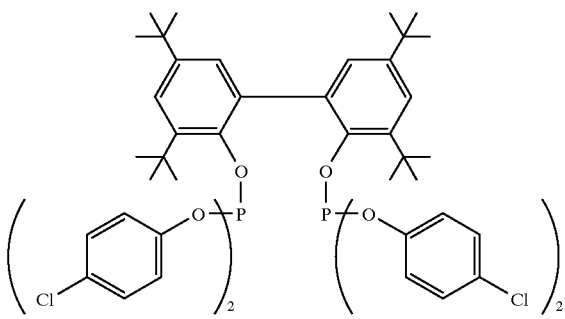
(22)
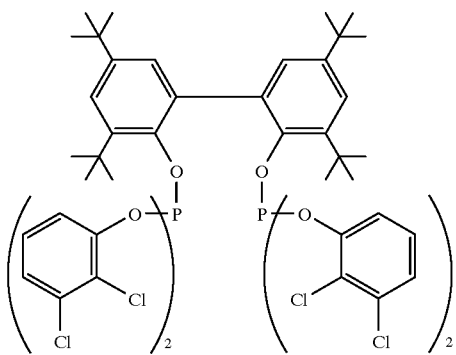
(23)
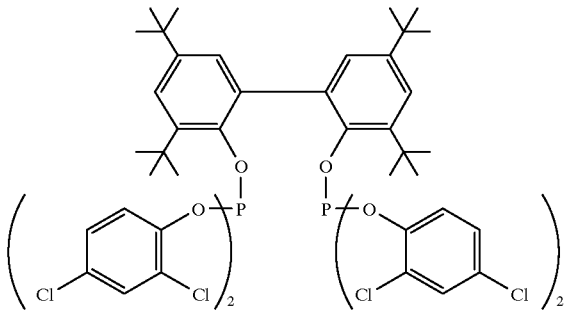
(24)

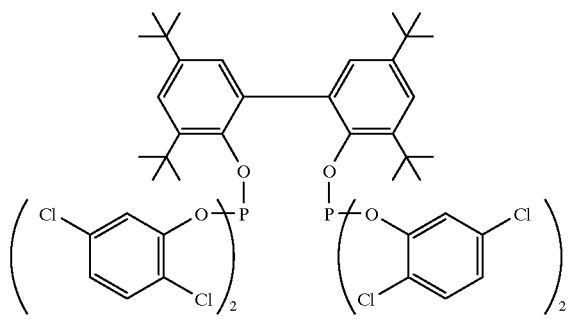
(25)
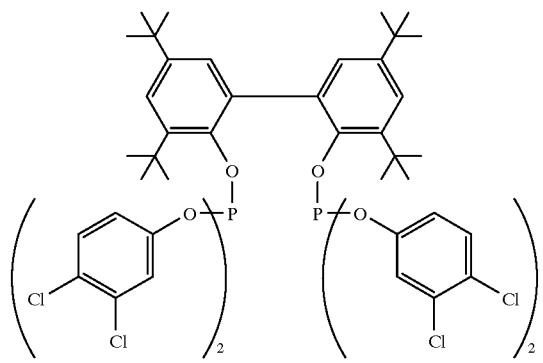
(26)
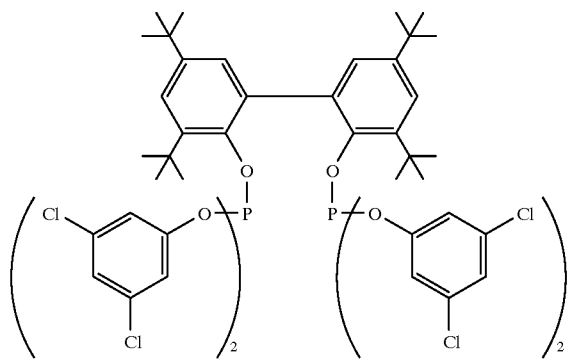
(27)
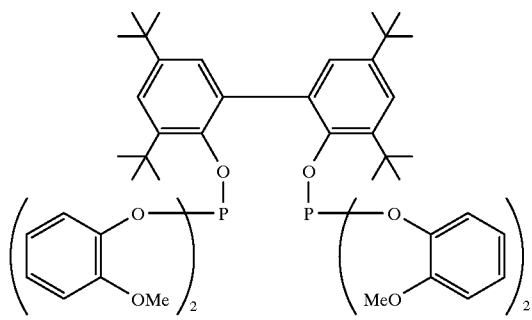
(28)

-continued
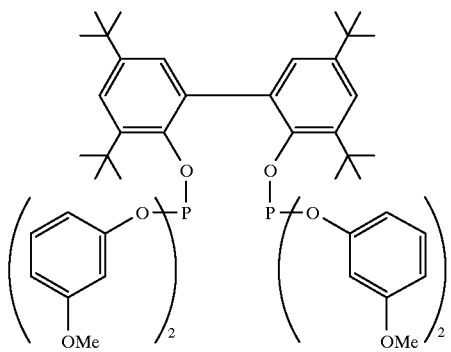
(29)
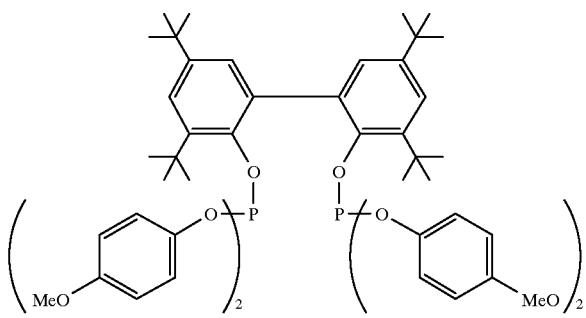
(30)
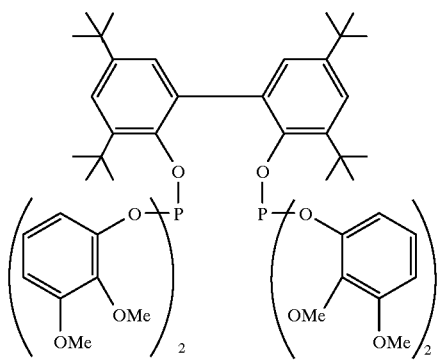
(31)
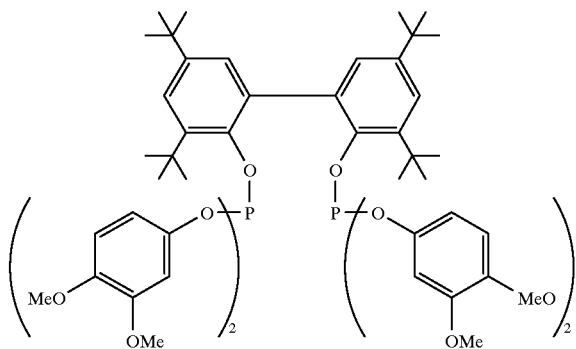
(32)

-continued
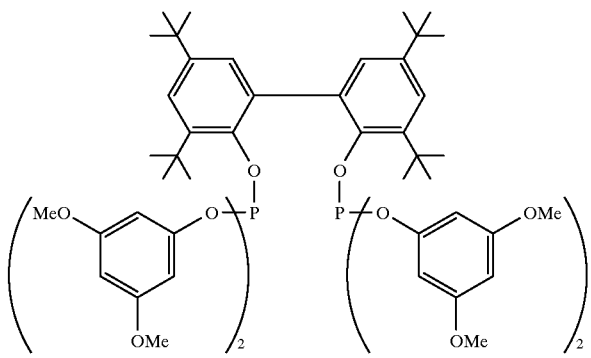
(33)
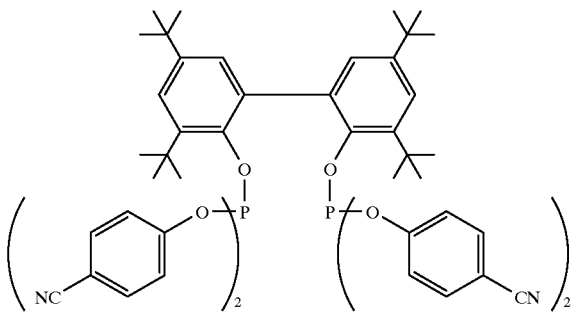
(34)
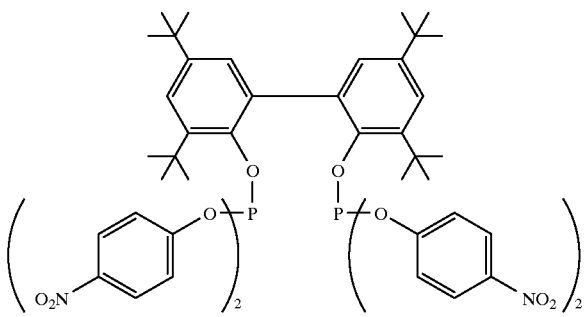
(35)
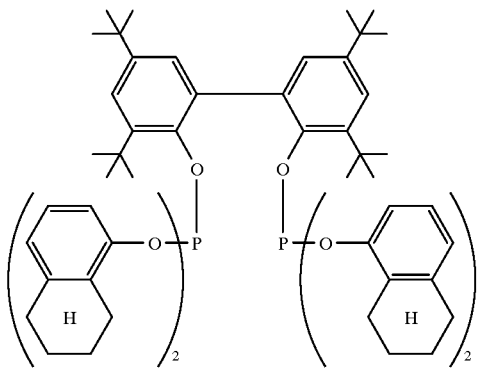
(36)

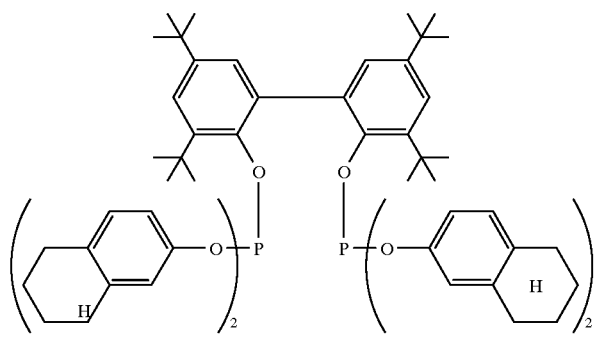
(37)
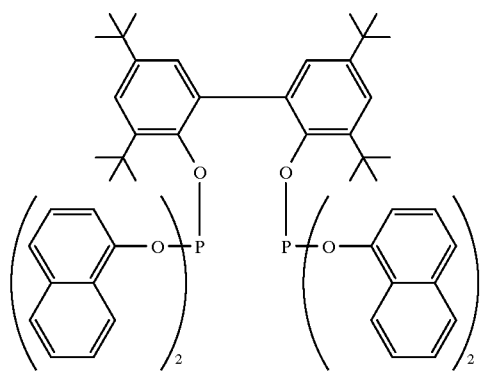
(38)
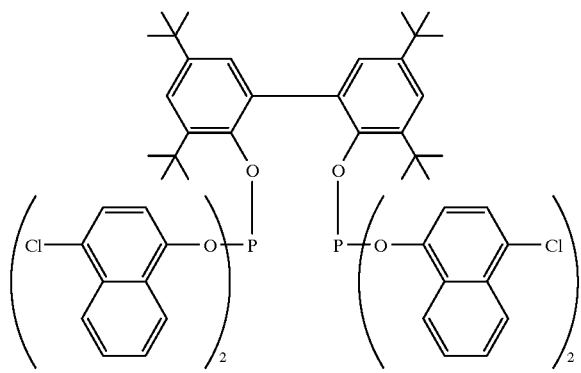
(39)
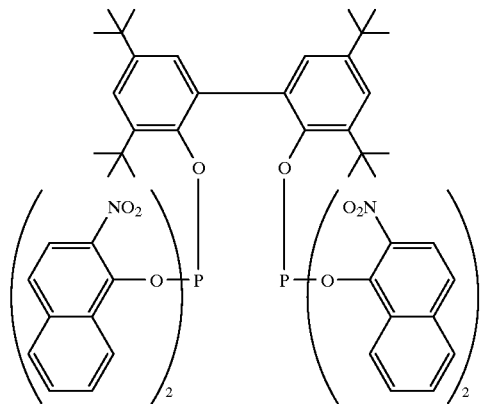
(40)

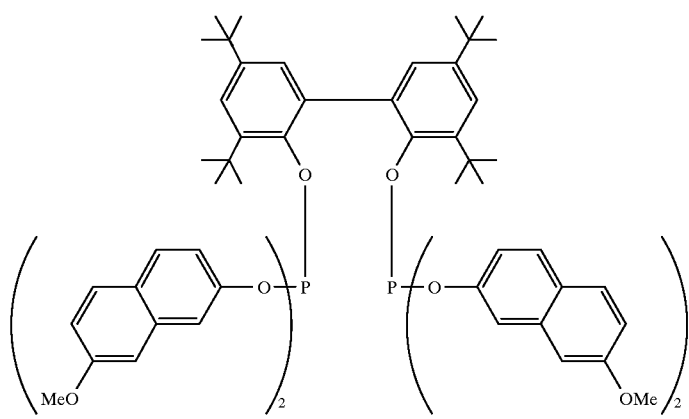
(41)
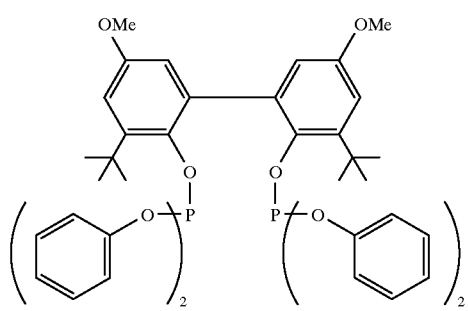
(42)
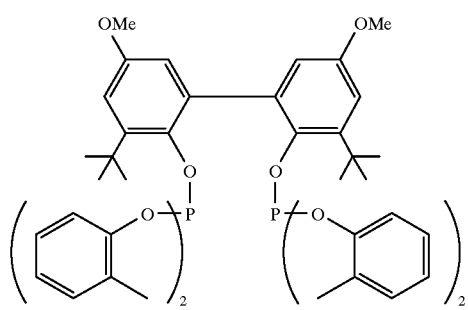
(43)
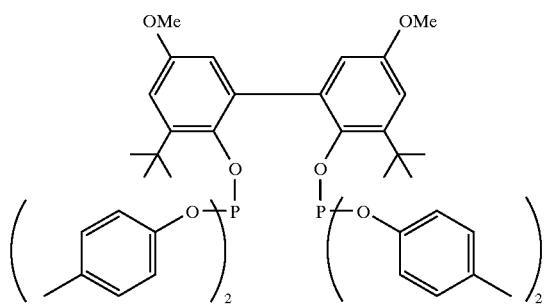
(44)

(45)
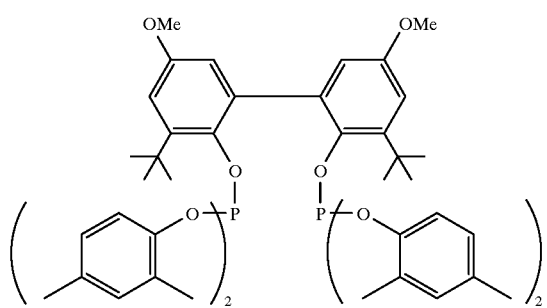
(46)
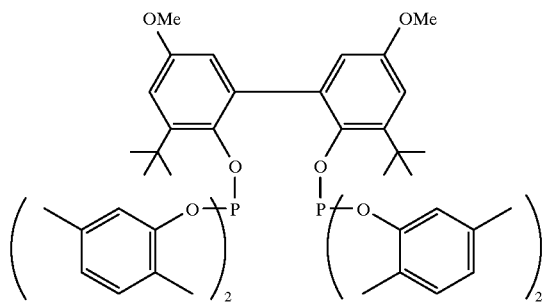
(47)
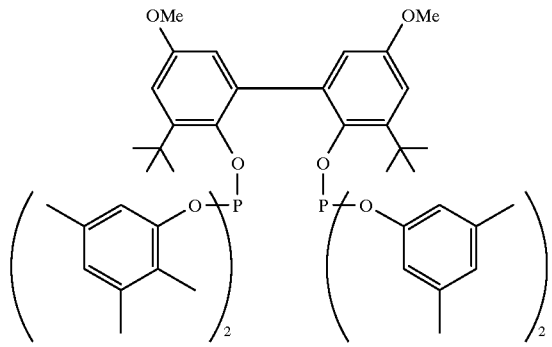
(48)
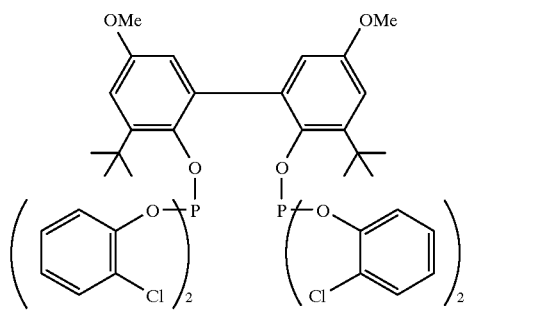
(49)
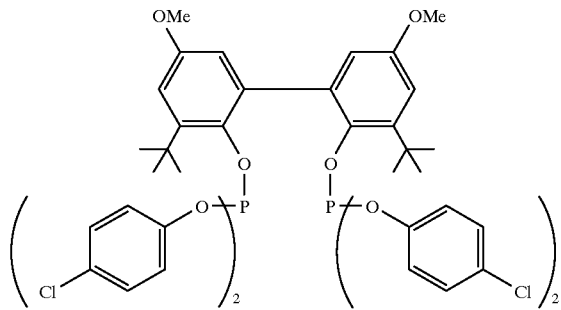

-continued
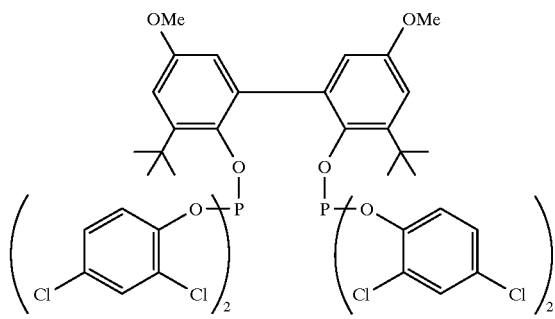
(50)
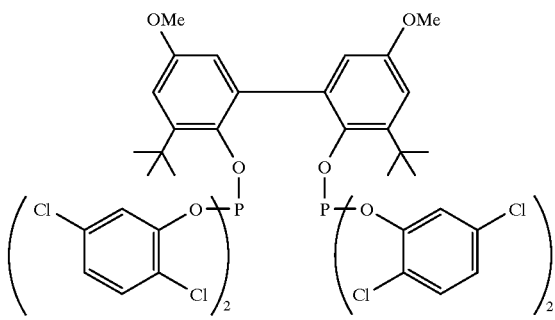
(51)
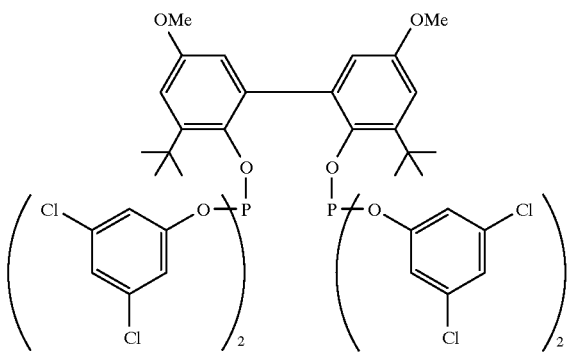
(52)
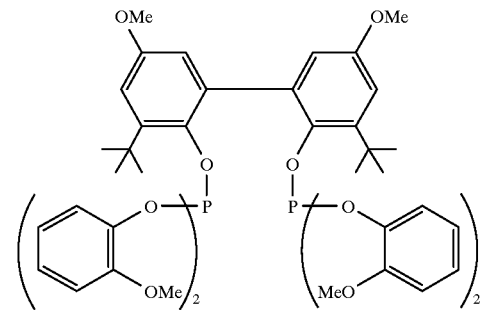
(53)

-continued
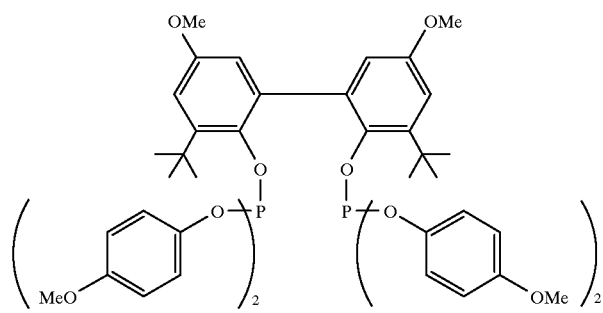
(54)
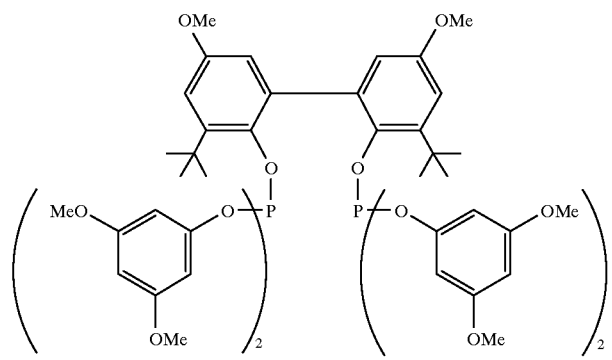
(55)
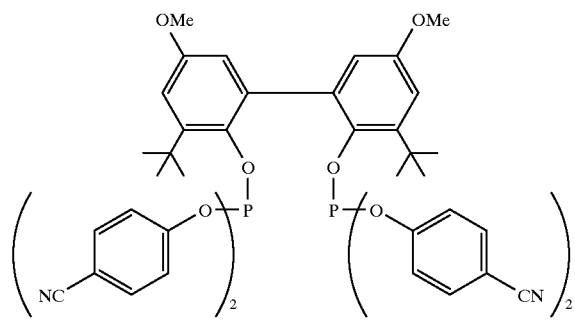
(56)
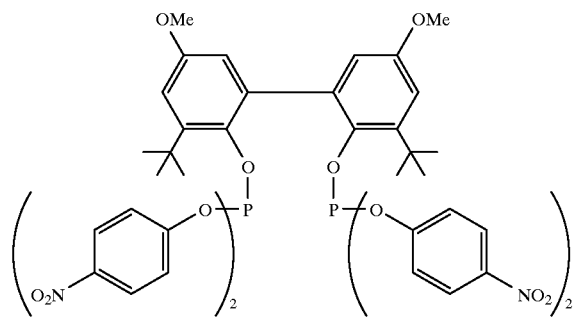
(57)

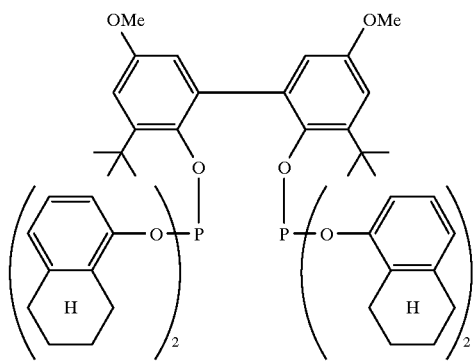
(58)
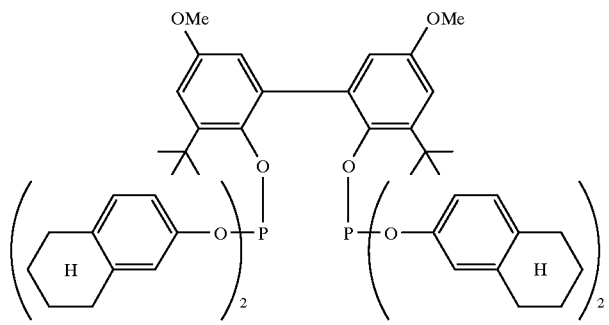
(59)
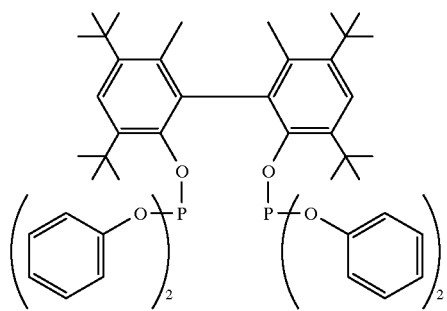
(60)
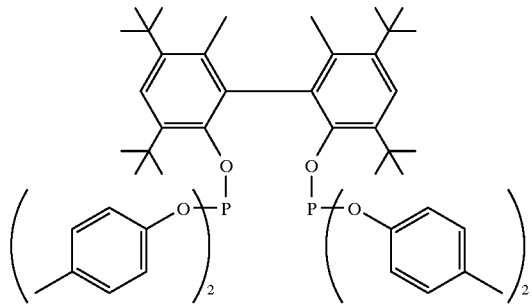
(61)

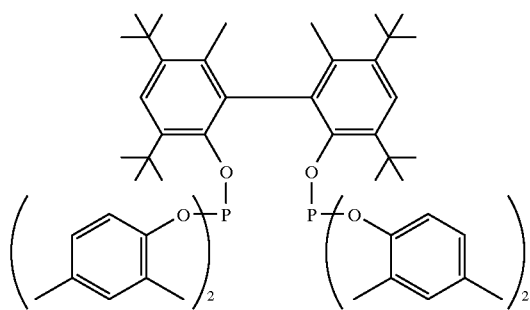
(62)
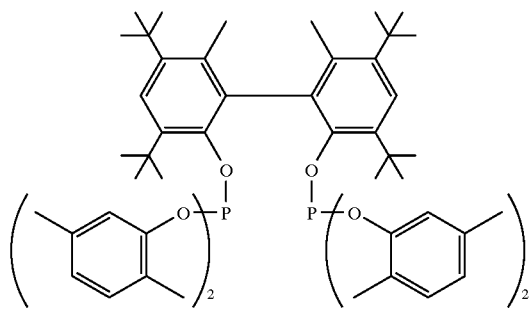
(63)
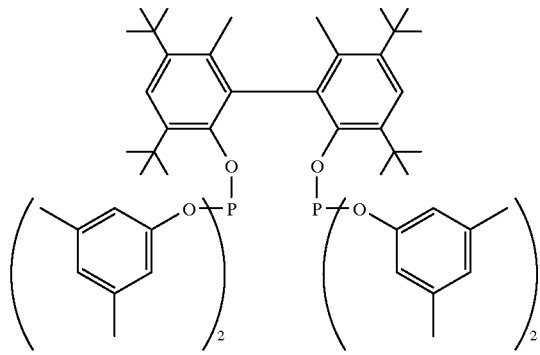
(64)
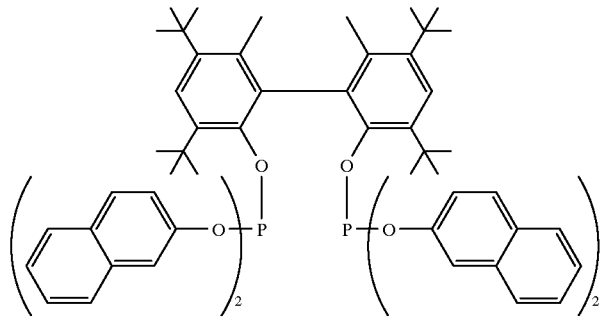
(65)

-continued
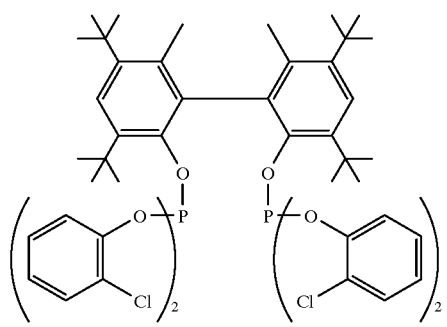
(66)
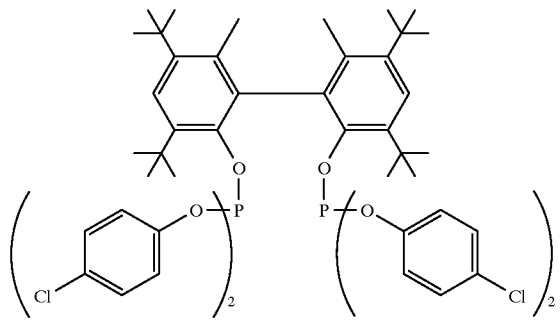
(67)
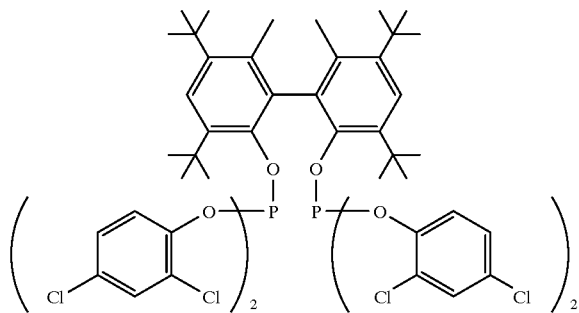
(68)
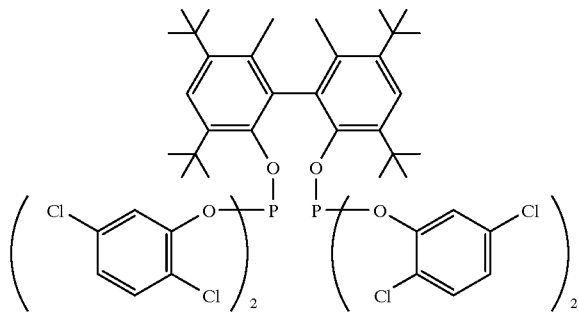
(69)

-continued
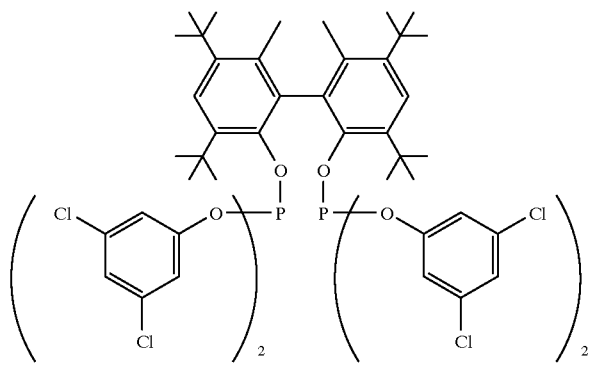
(70)
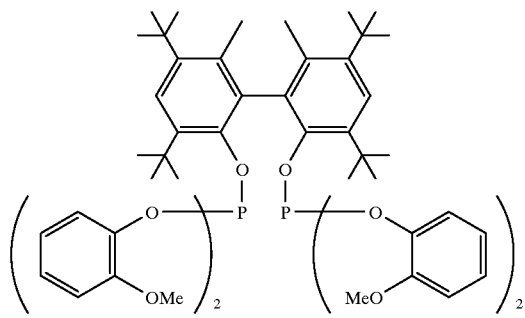
(71)
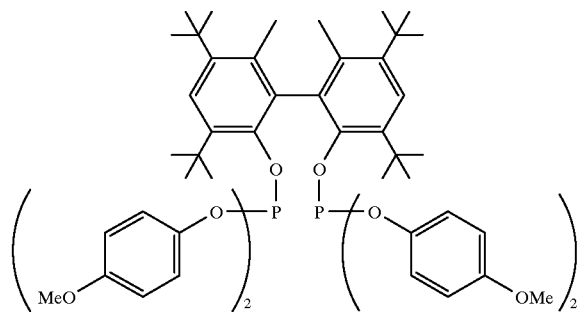
(72)
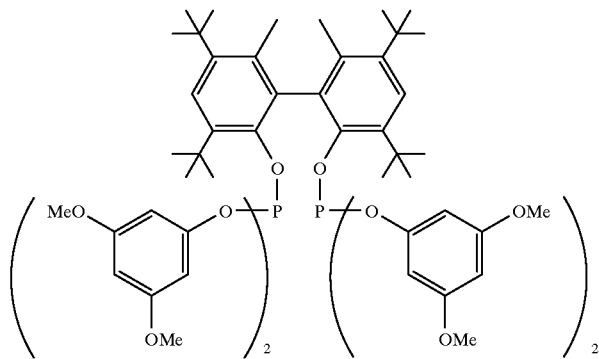
(73)

(74)
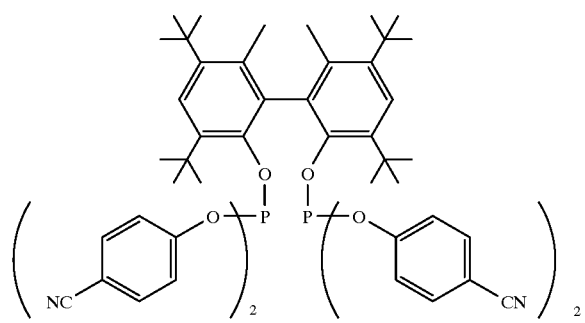
(75)
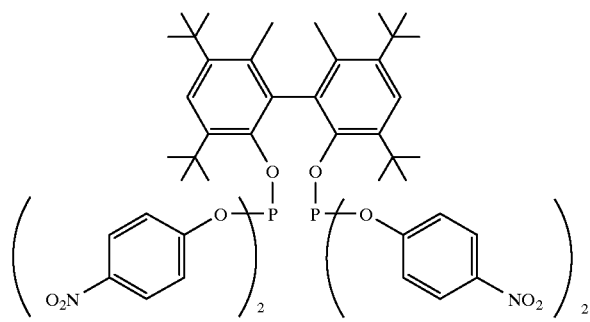
(76)
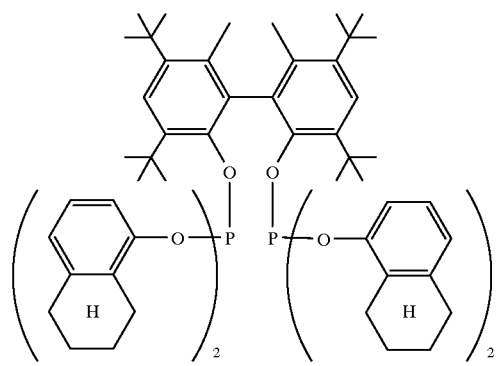
(77)
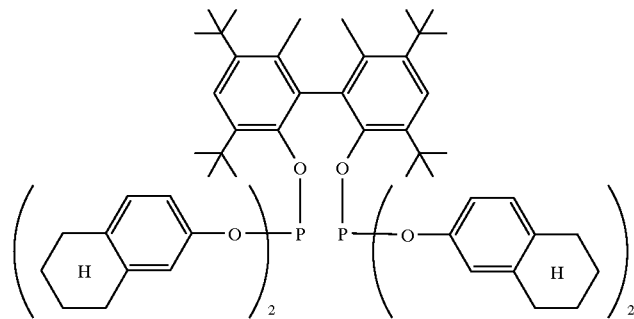

-continued
(78)
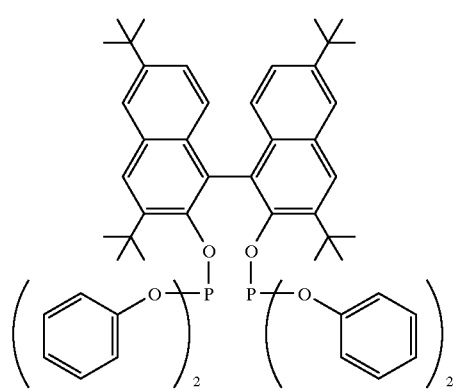
(79)
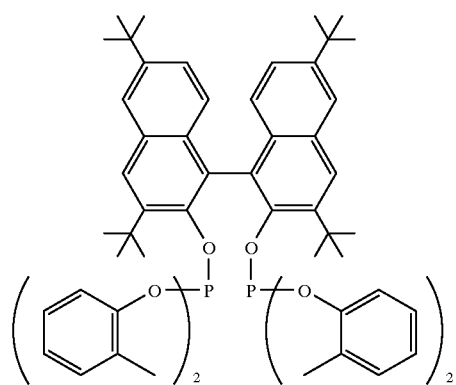
(80)
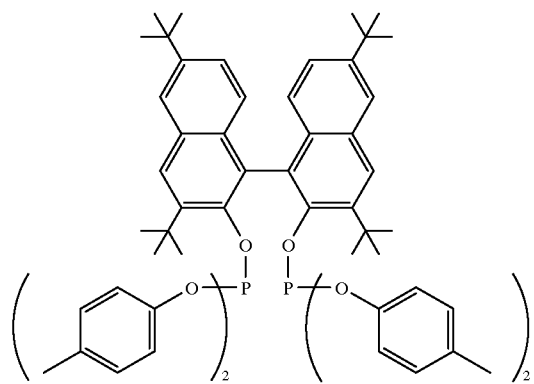
(81)
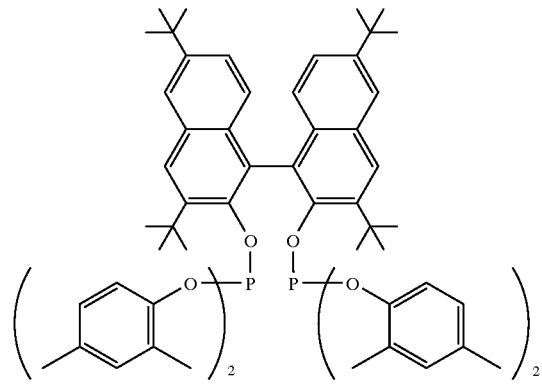

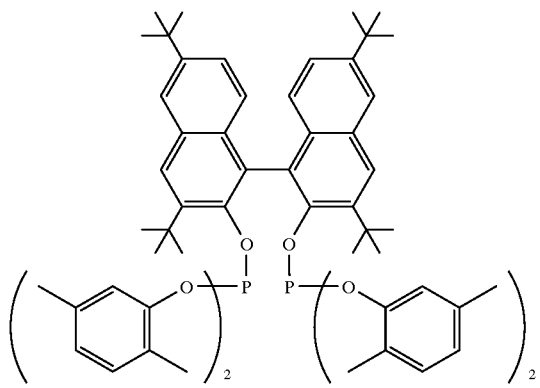
(82)
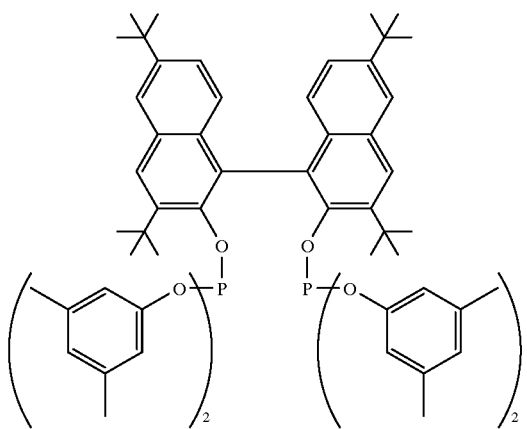
(83)
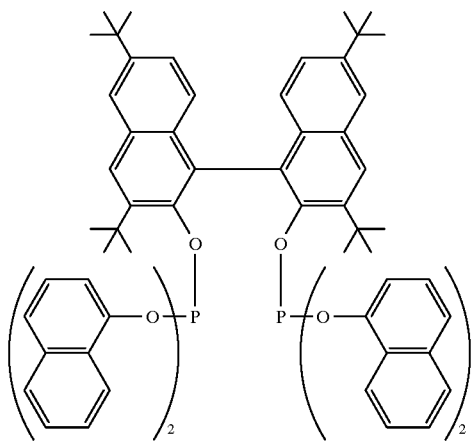
(84)

(85)
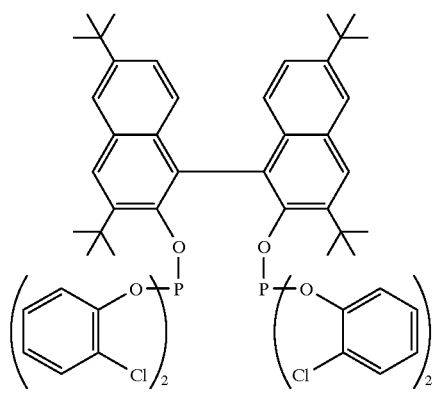
(86)
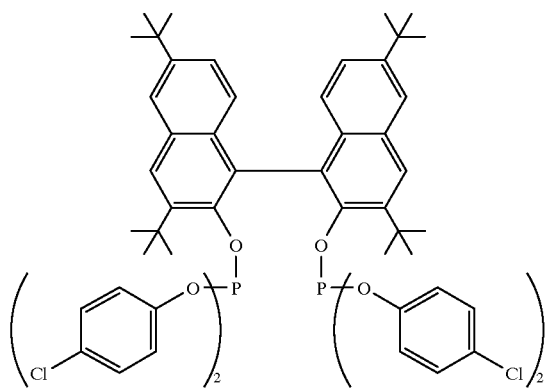
(87)
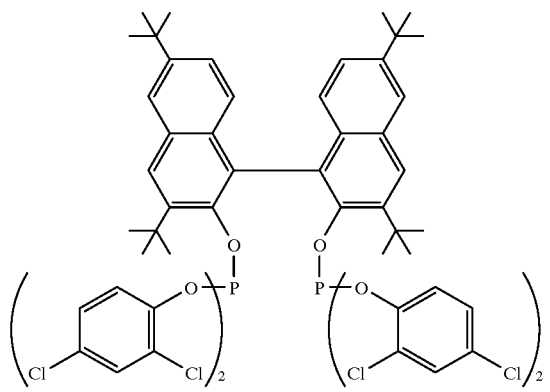
(88)
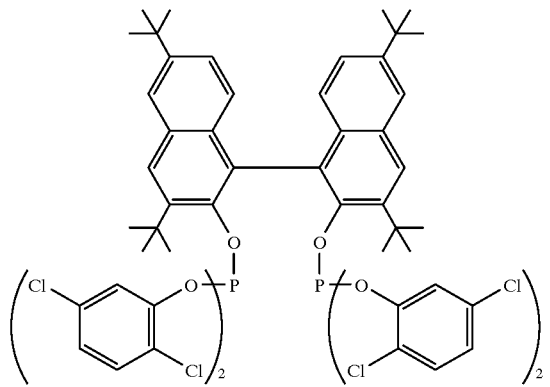

-continued
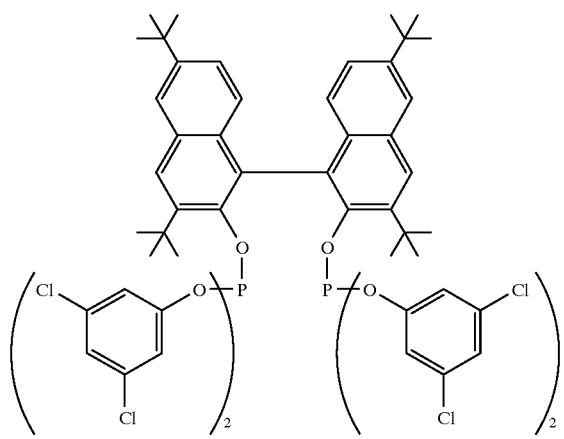
(89)
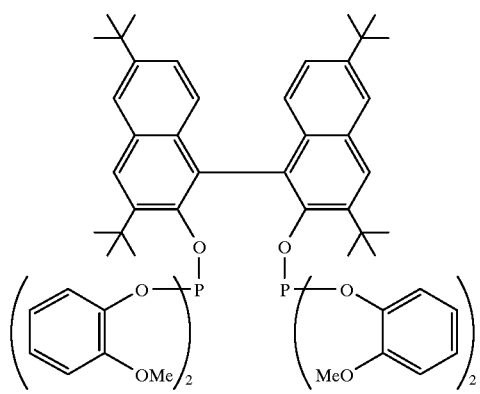
(90)
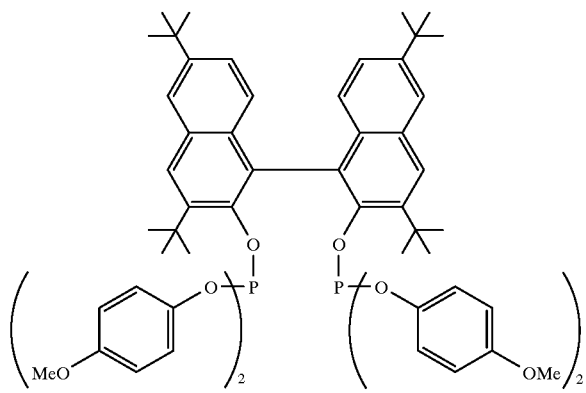
(91)

(92)
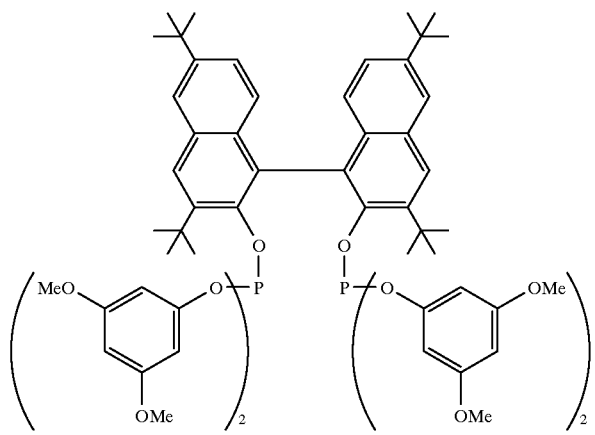
(93)
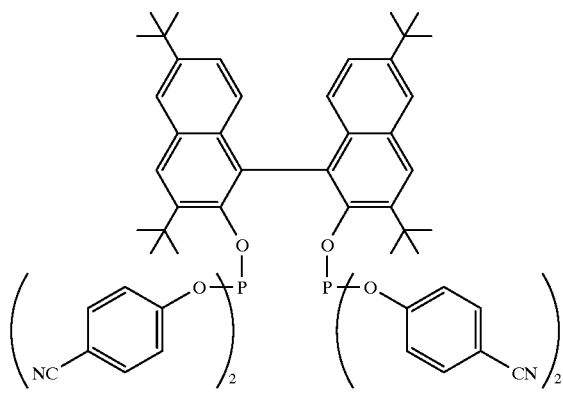
(94)
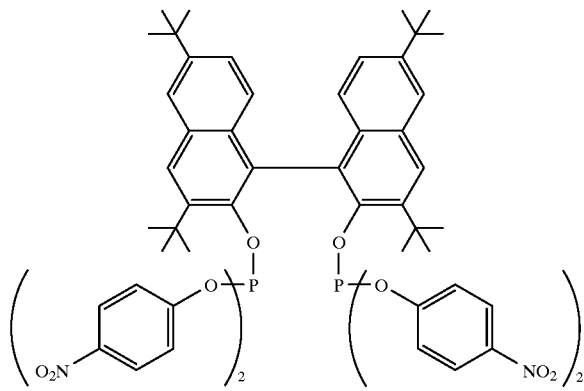

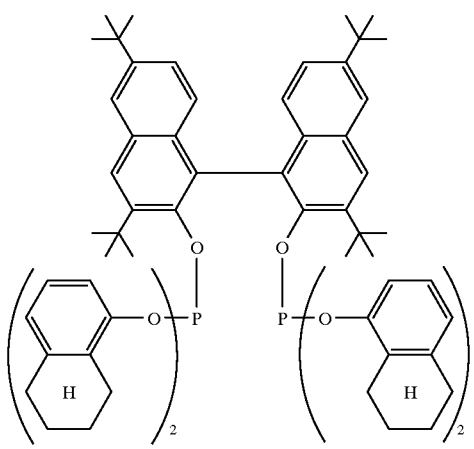
(95)
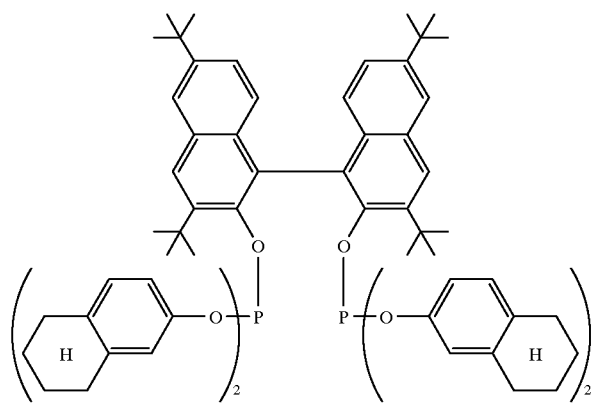
(96)
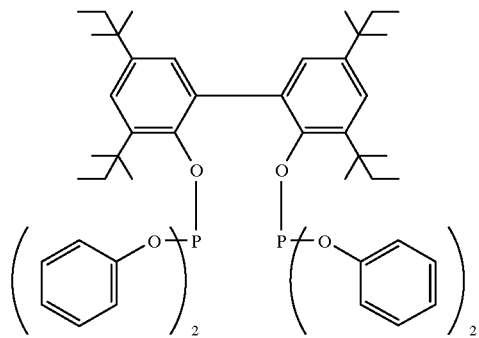
(97)
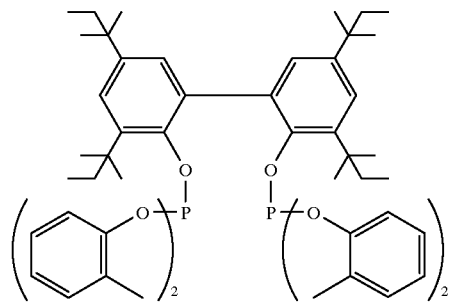
(98)

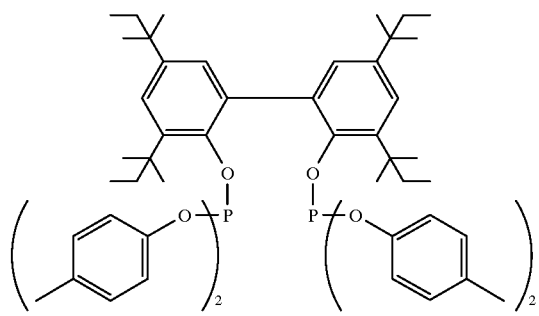
(99)
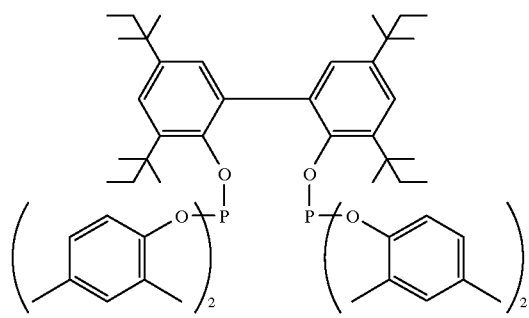
(100)
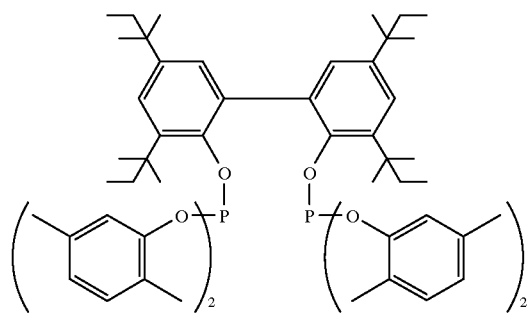
(101)
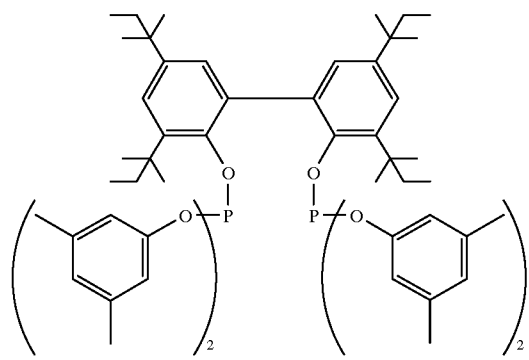
(102)

-continued
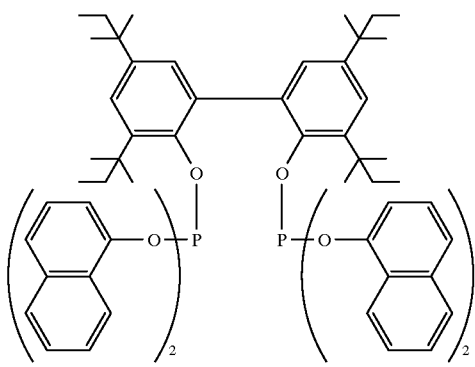
(103)
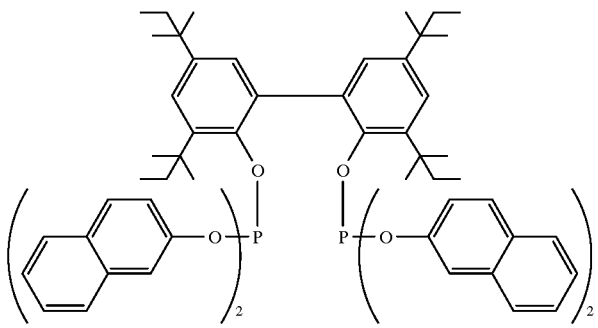
(104)
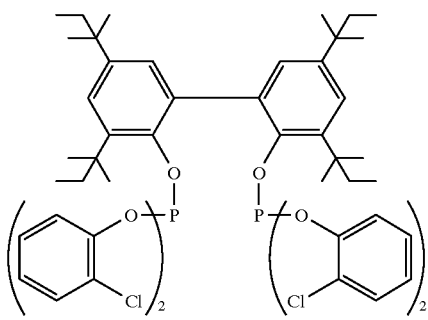
(105)
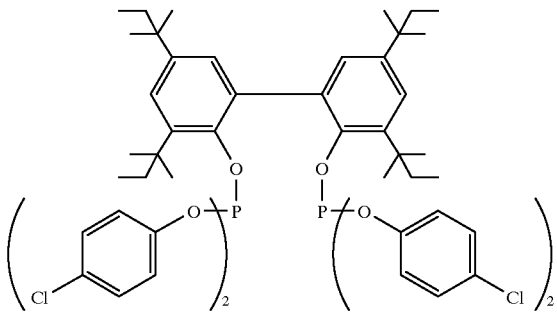
(106)

(107)
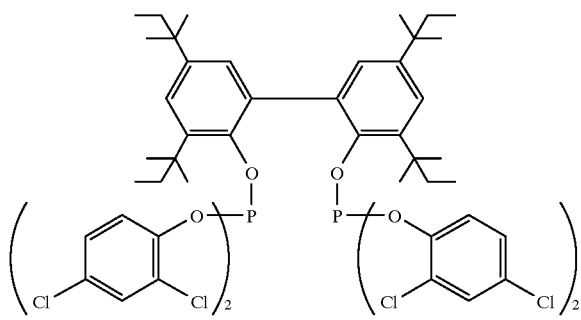
(108)
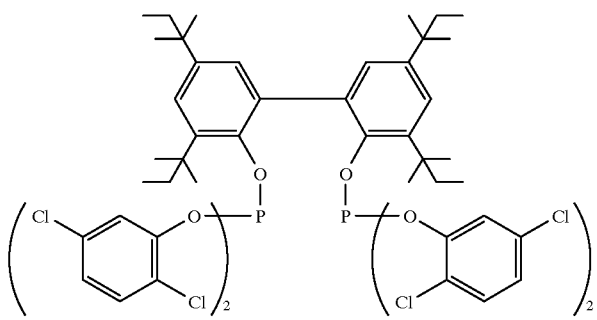
(109)
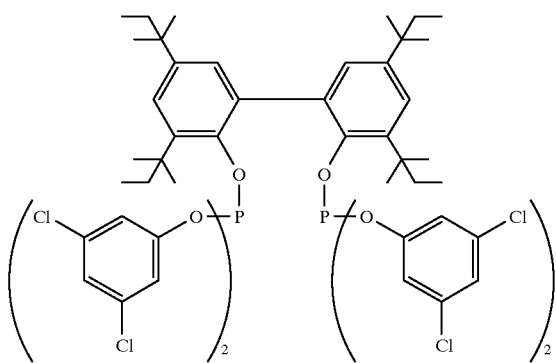
(110)
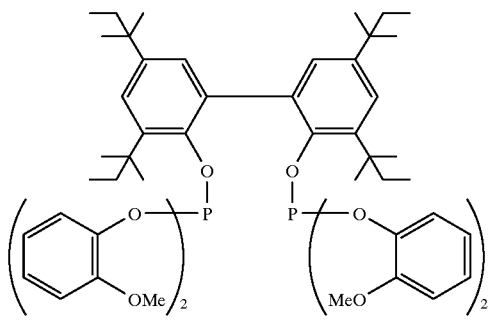

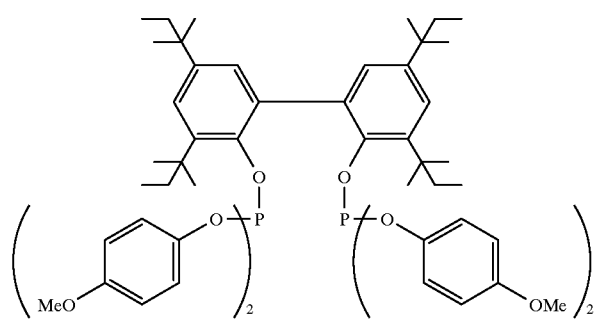
(111)
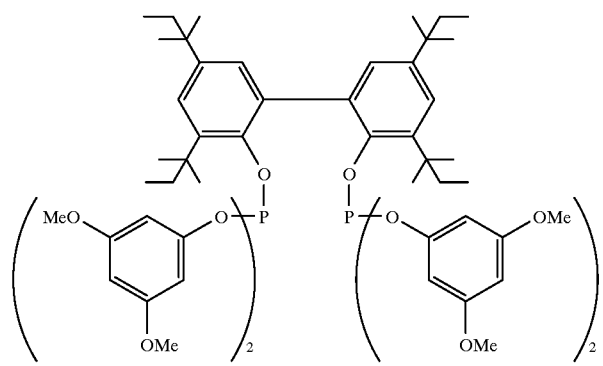
(112)
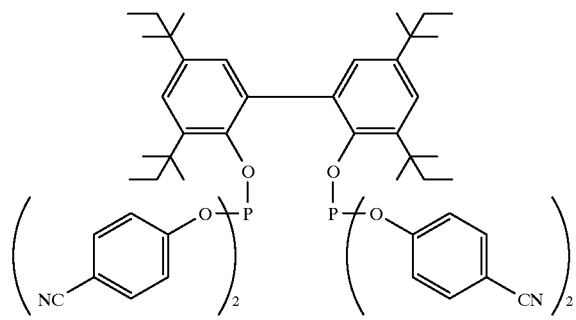
(113)
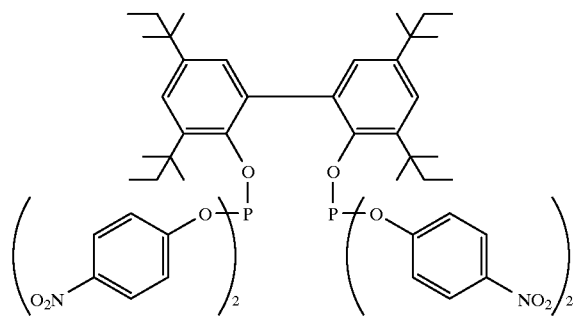
(114)

-continued
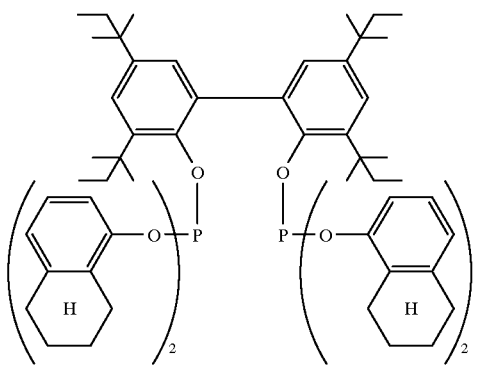
(115)
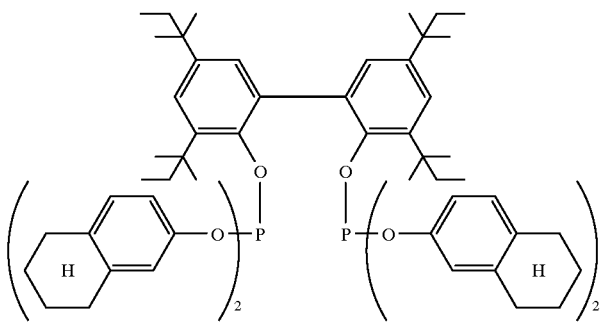
(116)
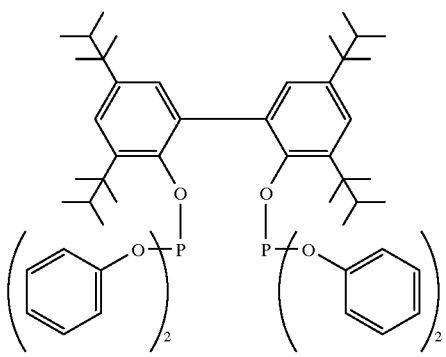
(117)
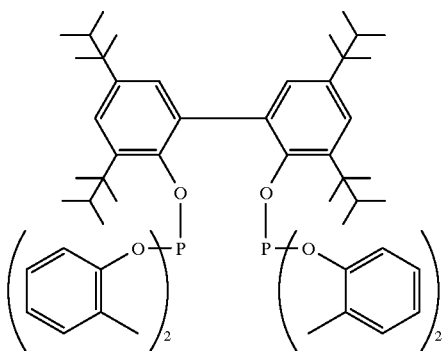
(118)

-continued
(119)
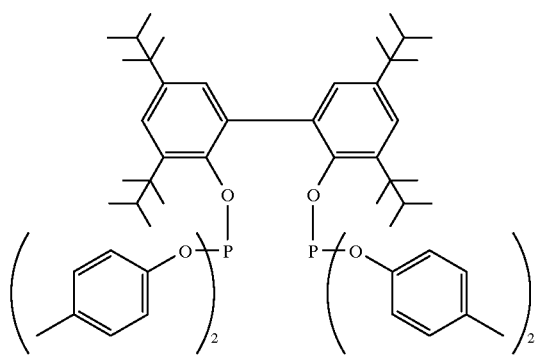
(120)
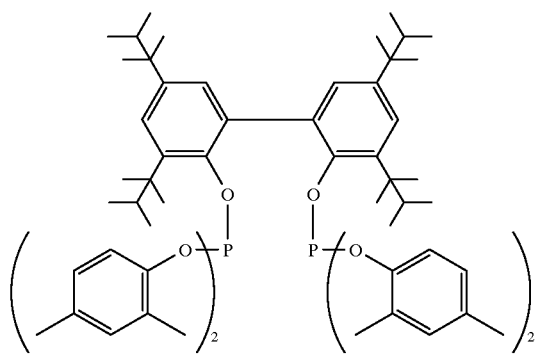
(121)
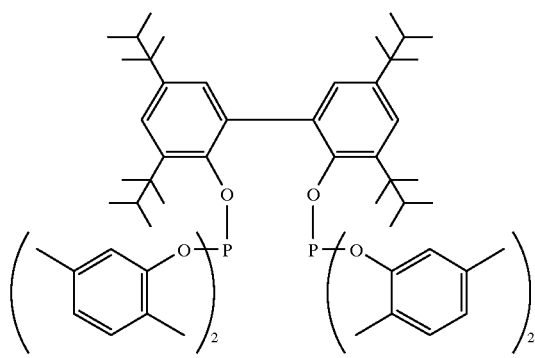
(122)
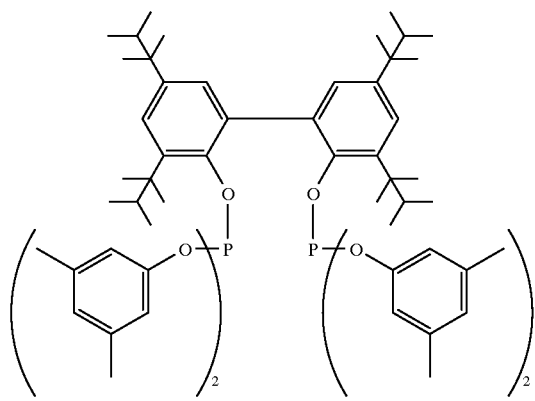

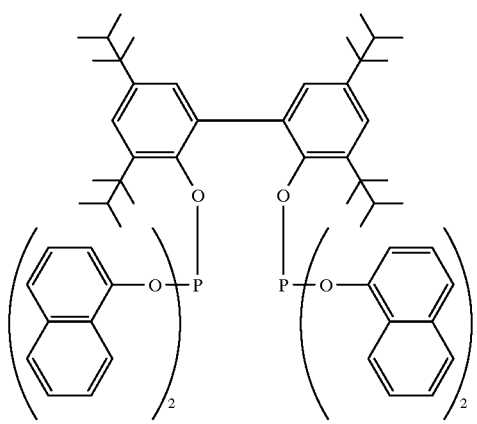
(123)
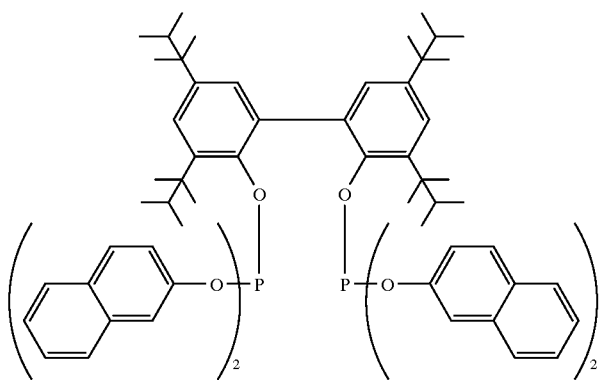
(124)
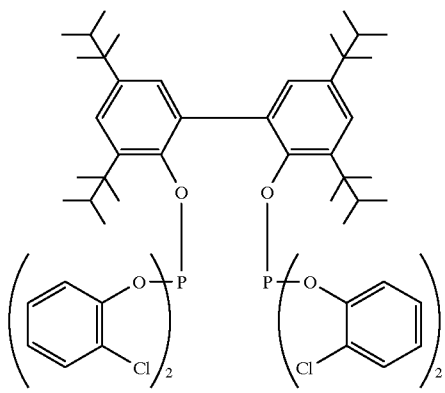
(125)
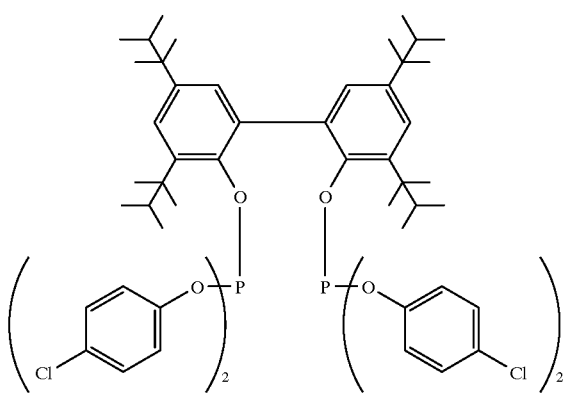
(126)

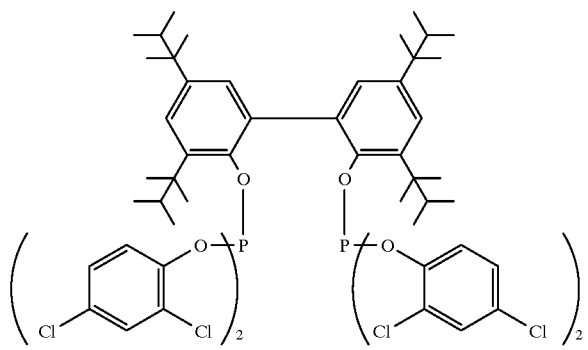
(127)
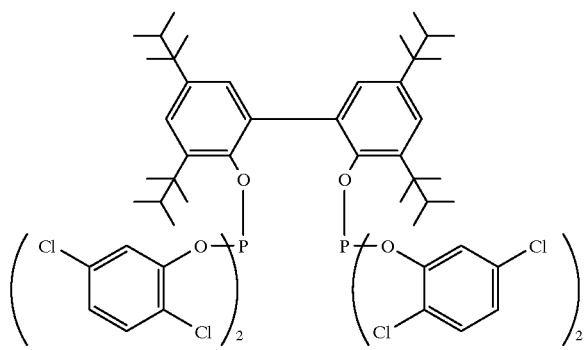
(128)
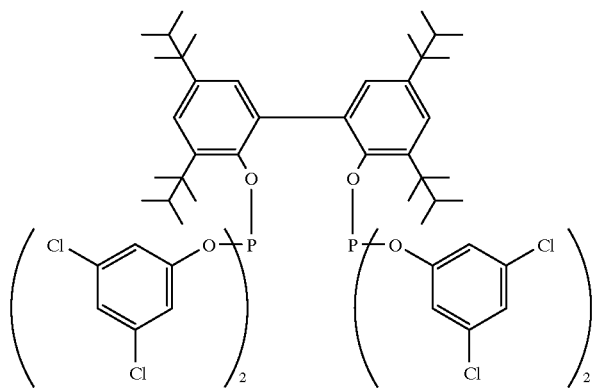
(129)
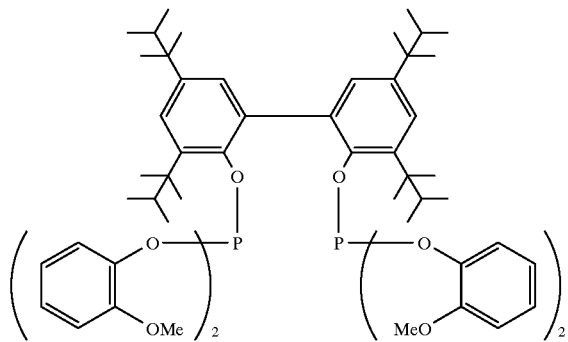
(130)

(131)
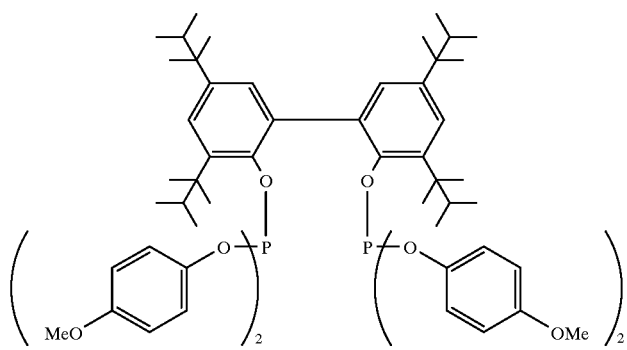
(132)
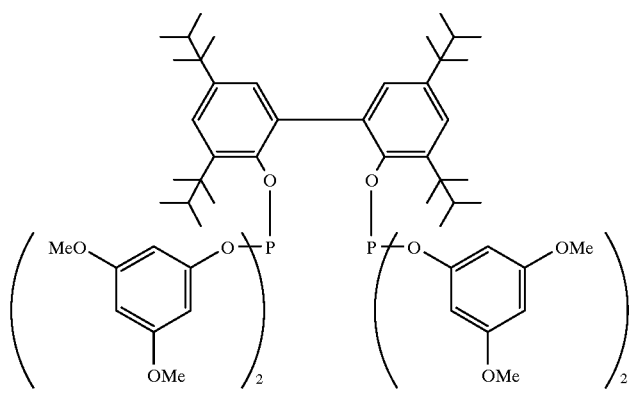
(133)
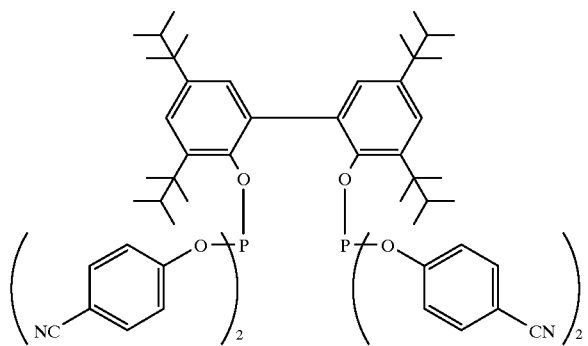
(134)
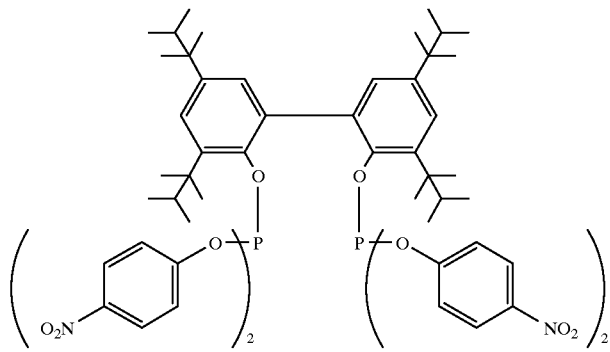

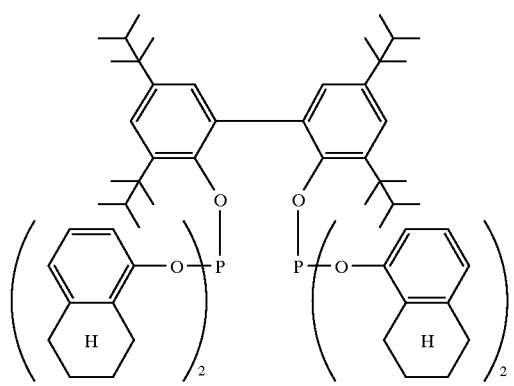
(135)
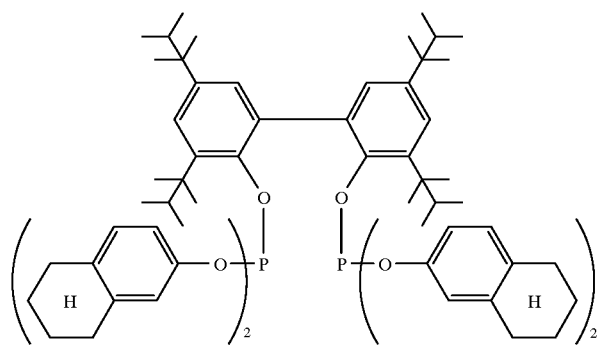
(136)
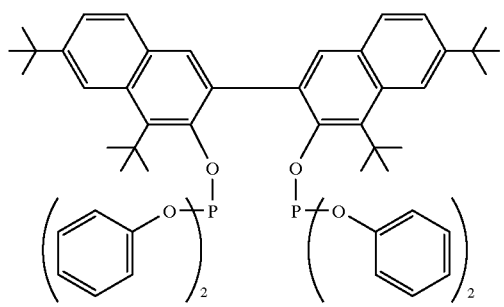
(137)
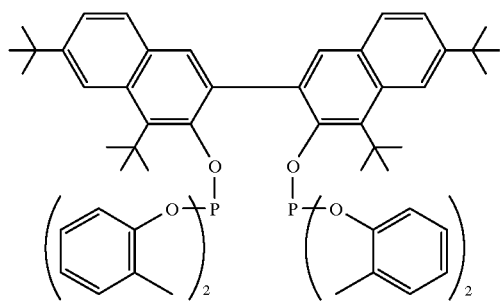
(138)
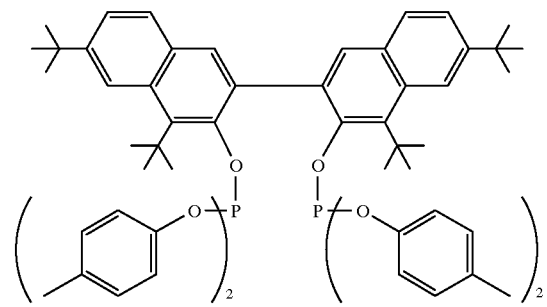
(139)

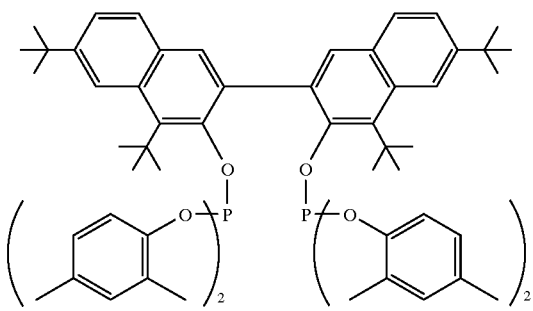
(140)
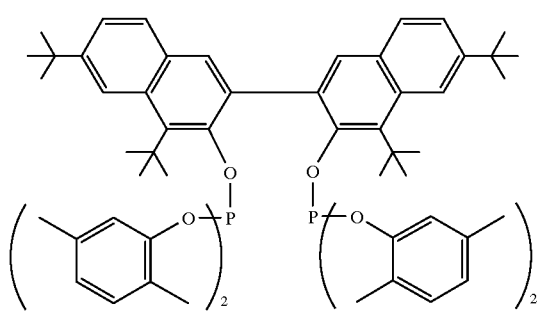
(141)
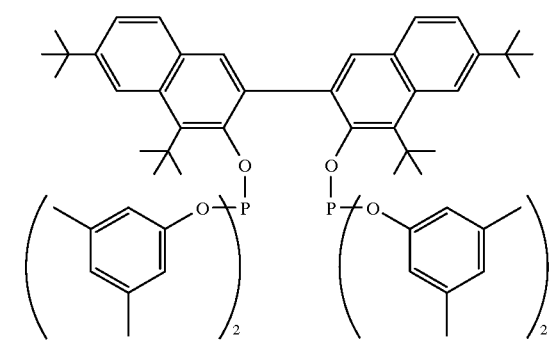
(142)
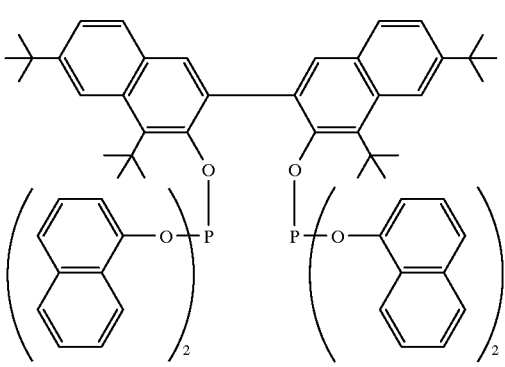
(143)

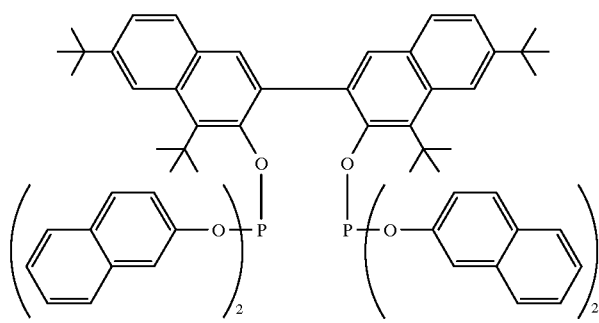
(144)
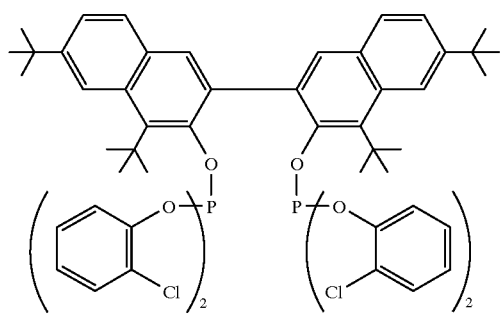
(145)
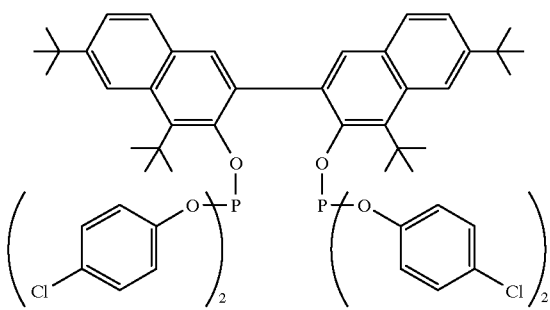
(146)
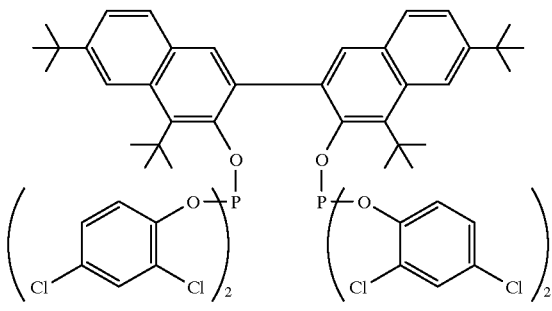
(147)
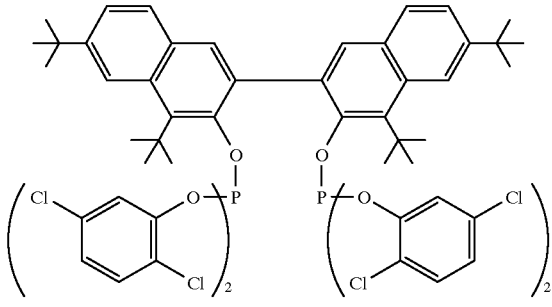
(148)

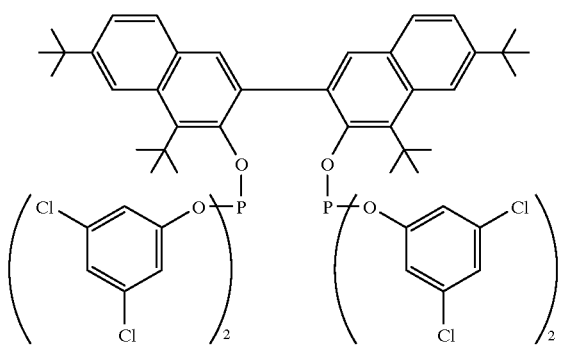
(149)
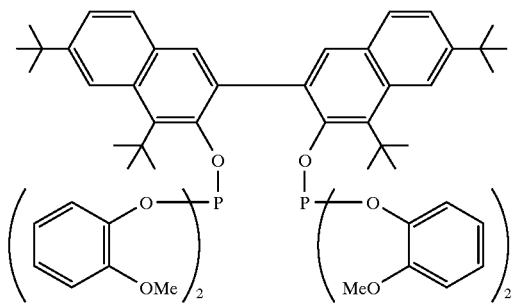
(150)
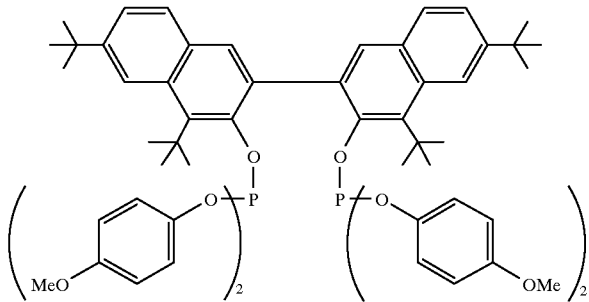
(151)
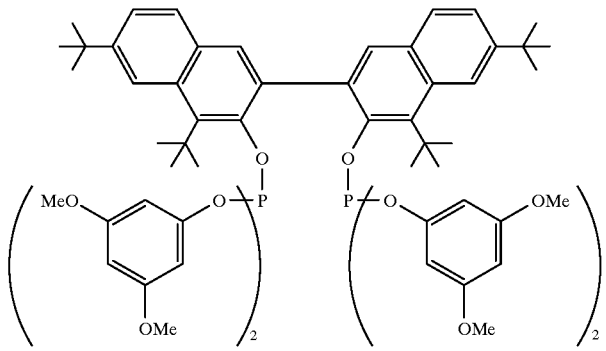
(152)

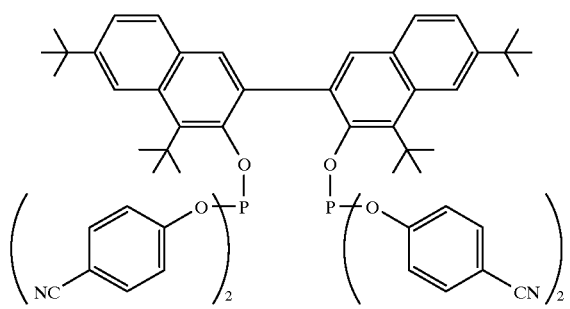
(153)
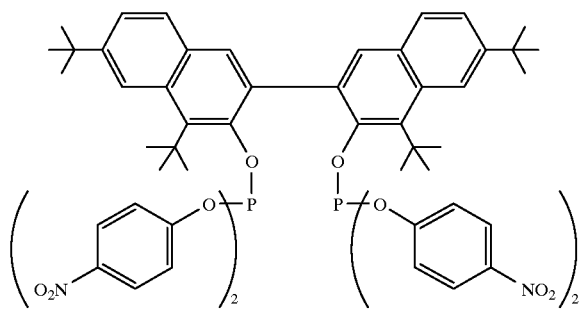
(154)
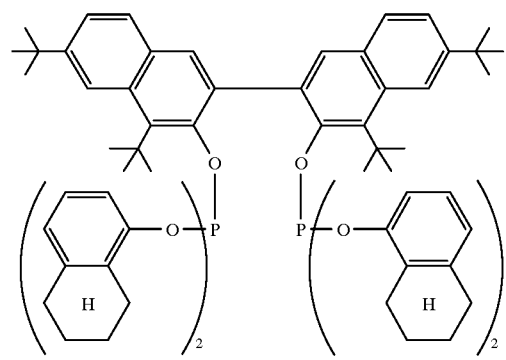
(155)
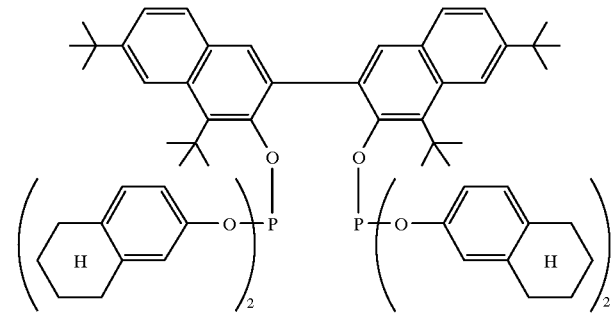
(156)

-continued
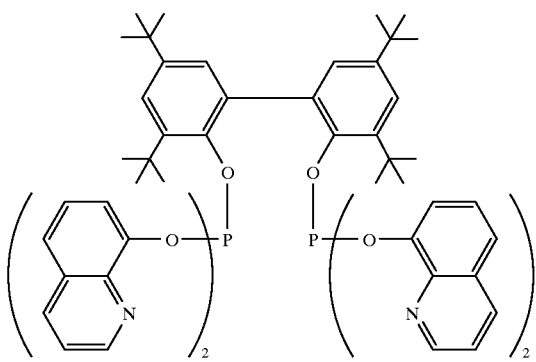
(157)
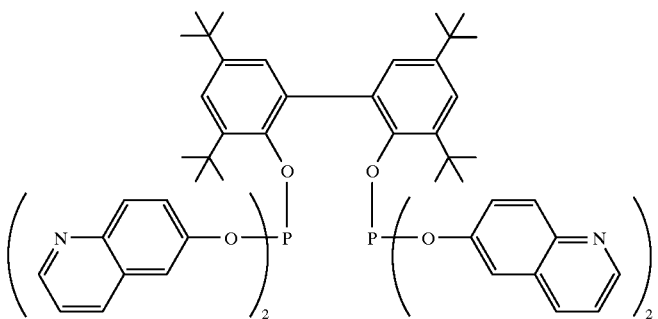
(158)
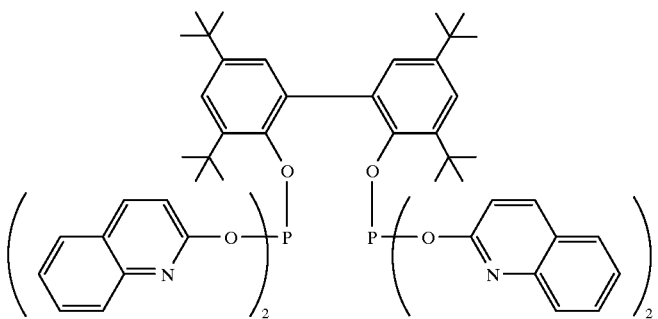
(159)
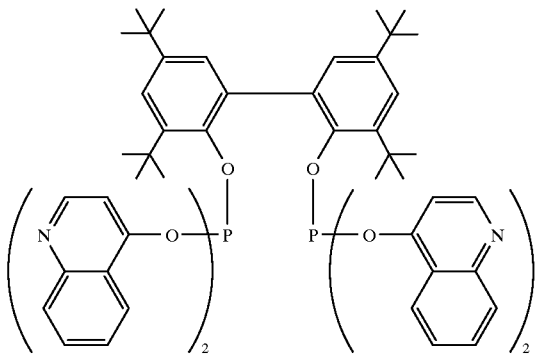
(160)

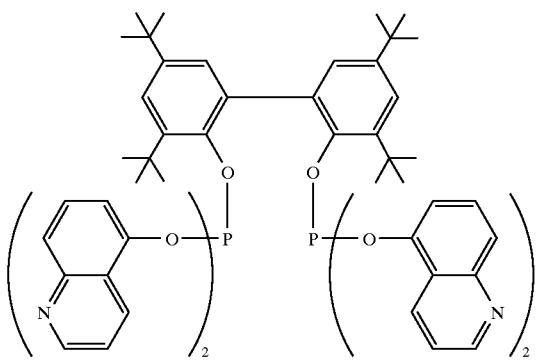
(161)
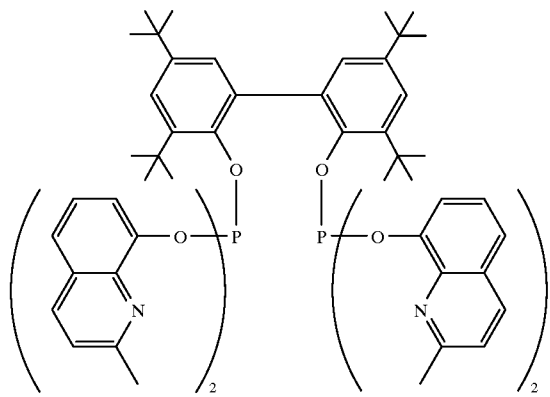
(162)
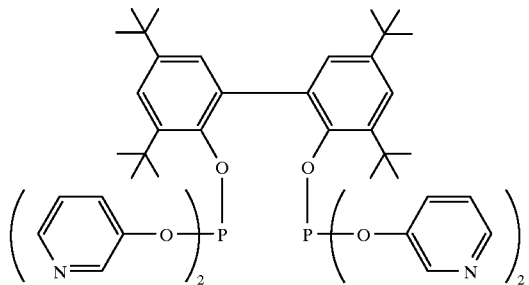
(163)
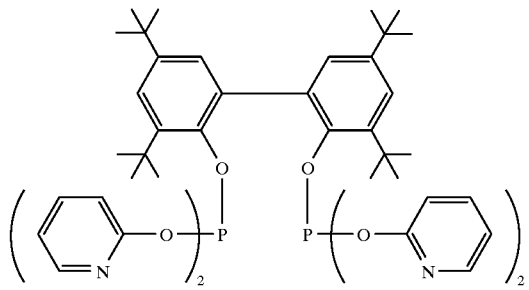
(164)

-continued
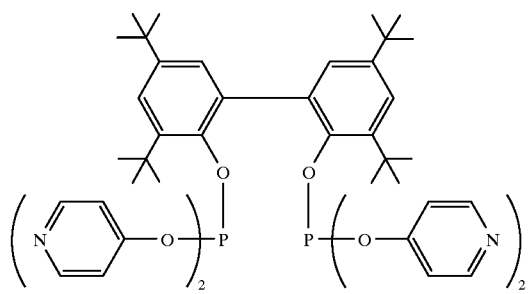
(165)
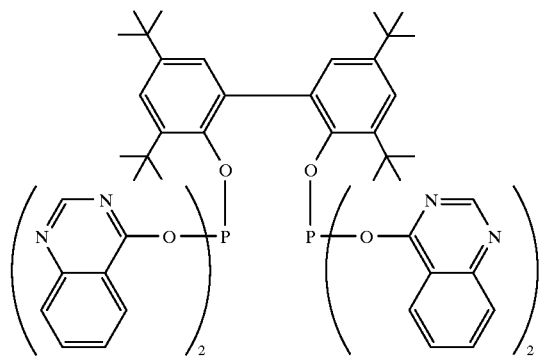
(166)
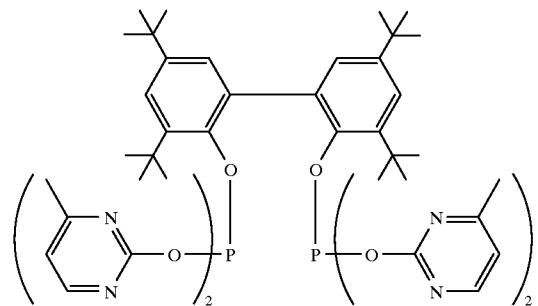
(167)
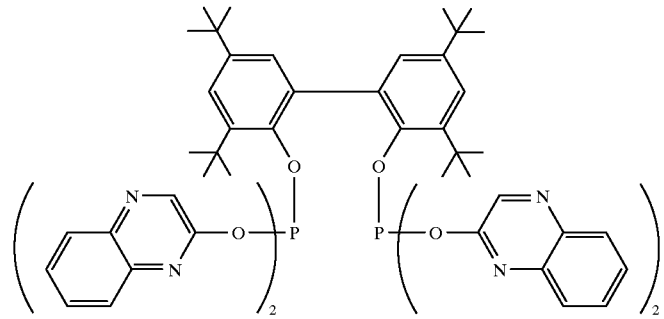
(168)

-continued
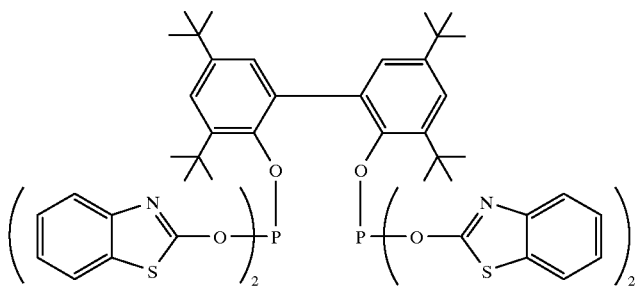
(169)
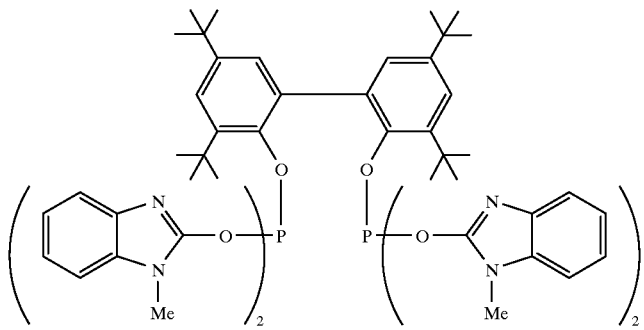
(170)
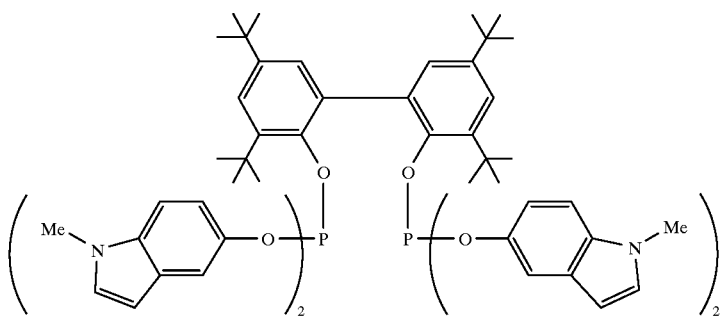
(171)
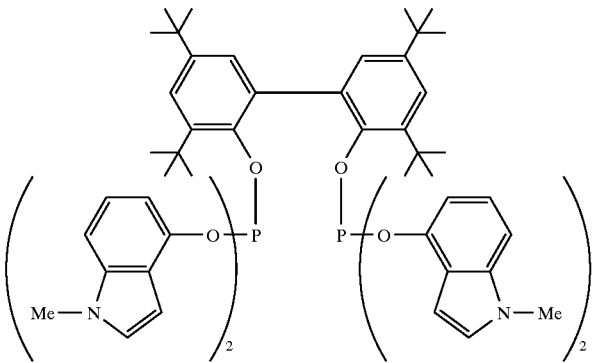
(172)

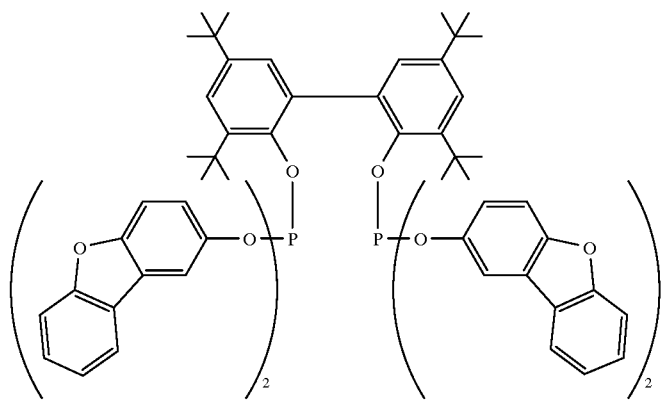
(173)
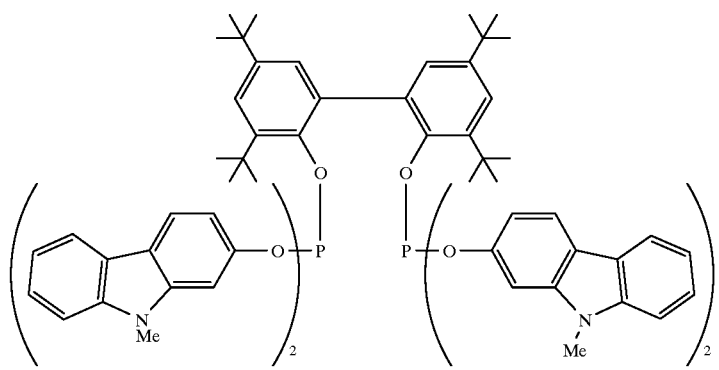
(174)
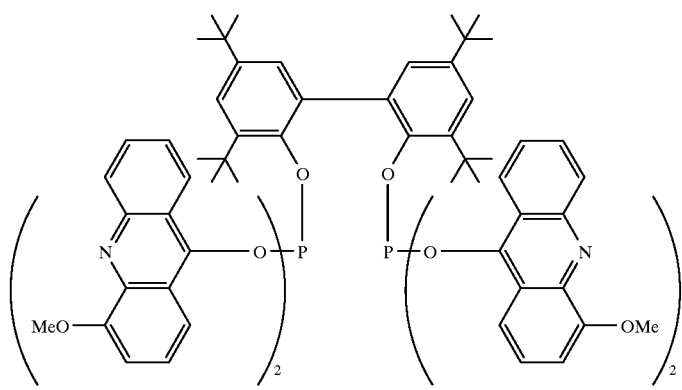
(175)
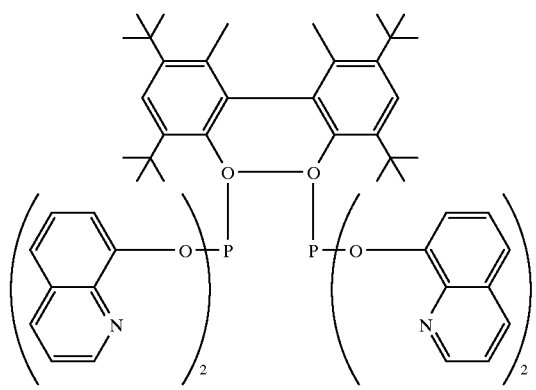
(176)

(177)
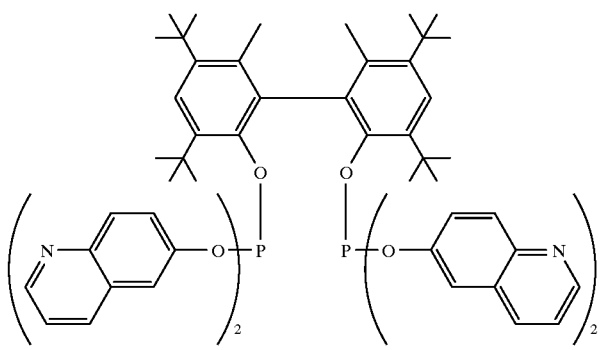
(178)
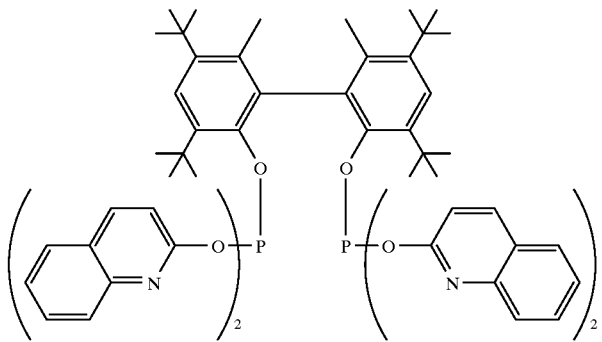
(179)
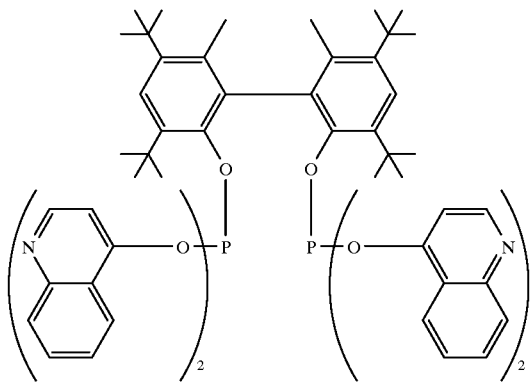
(180)
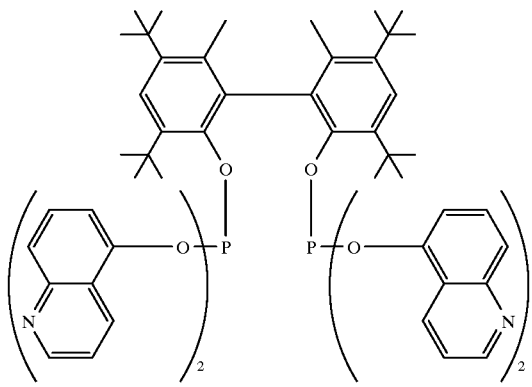

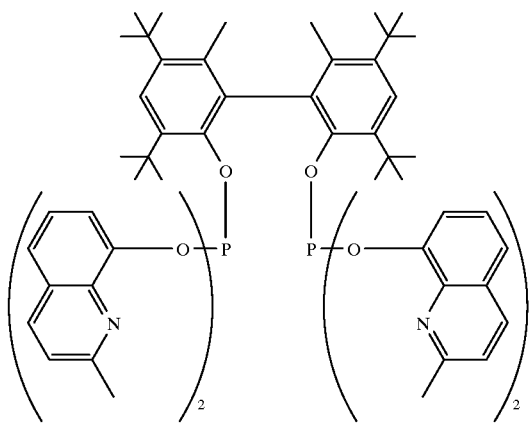
(181)
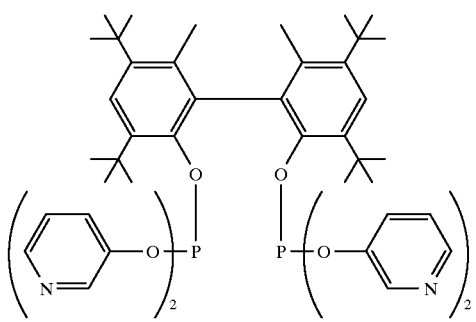
(182)
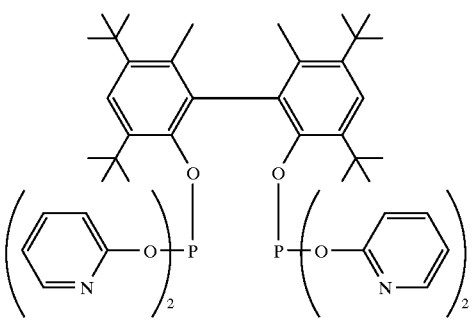
(183)
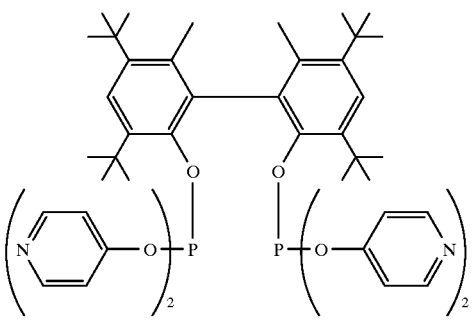
(184)

(185)
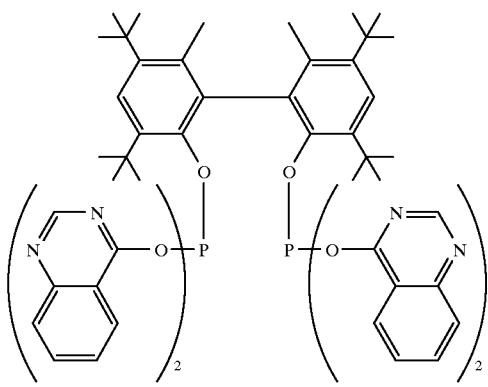
(186)
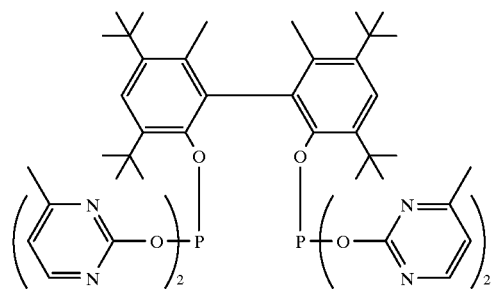
(187)
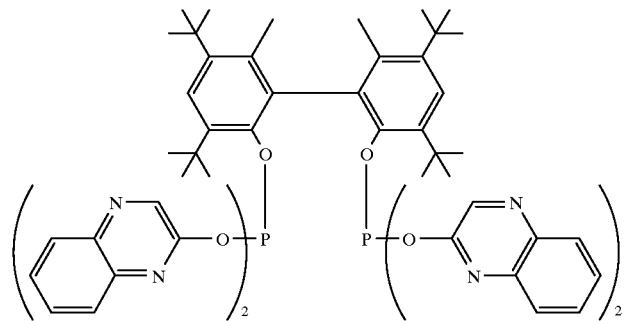
(188)
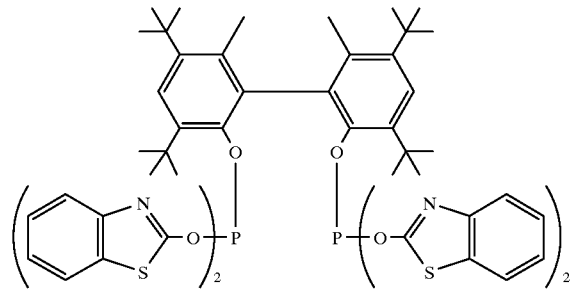

-continued
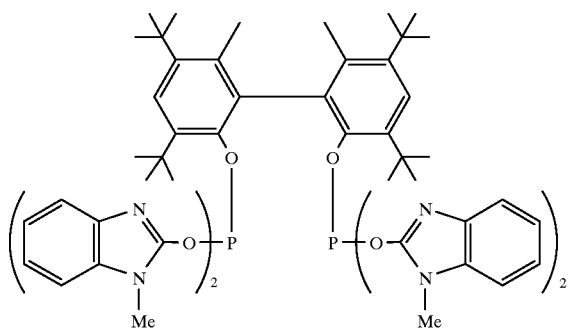
(189)
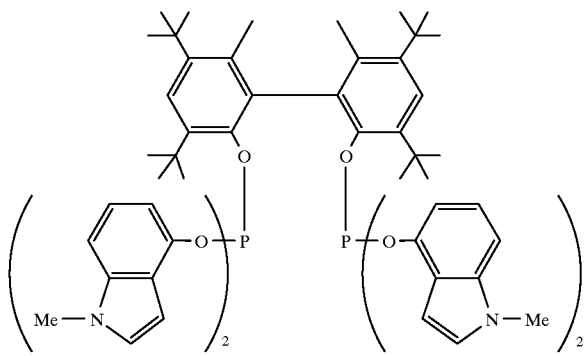
(190)
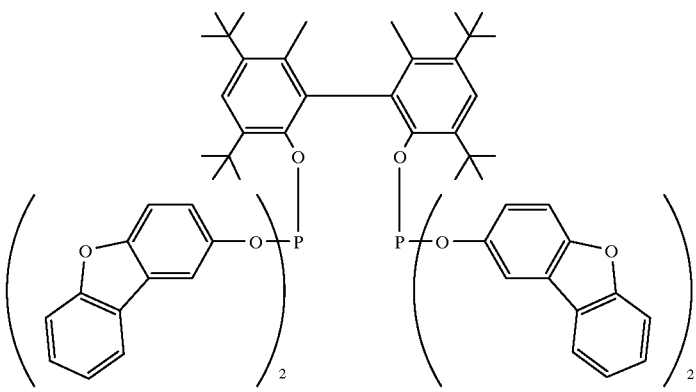
(191)
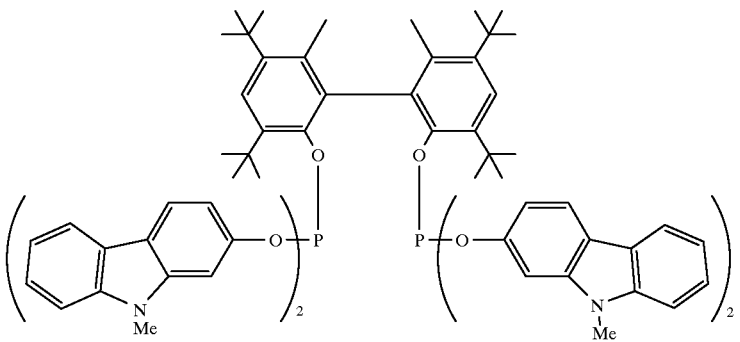
(192)

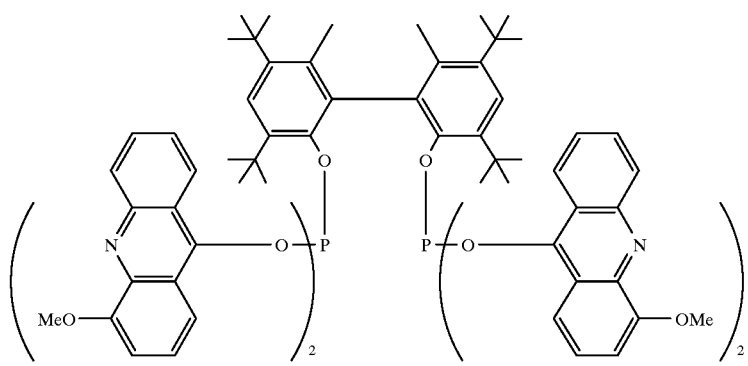
(193)
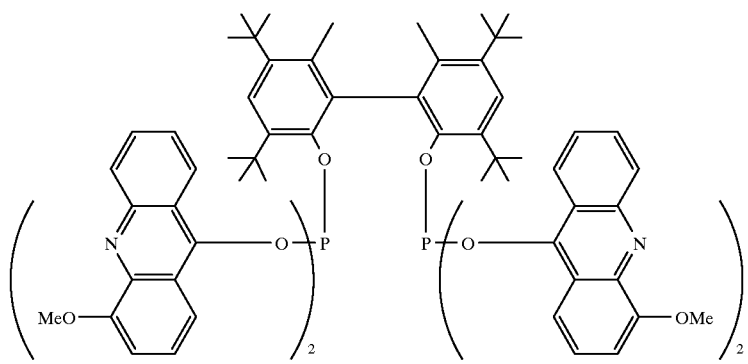
(194)
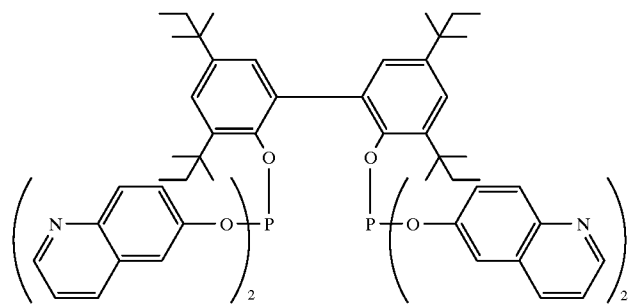
(195)
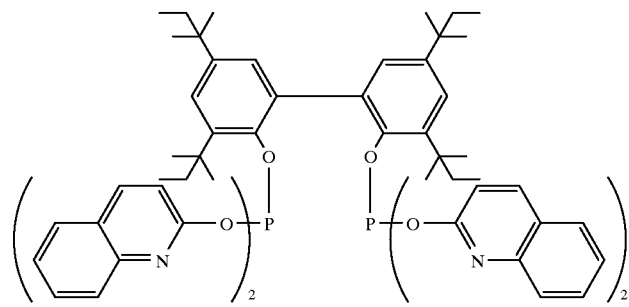
(196)

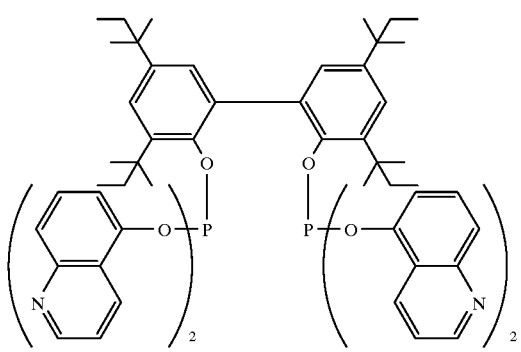
(197)
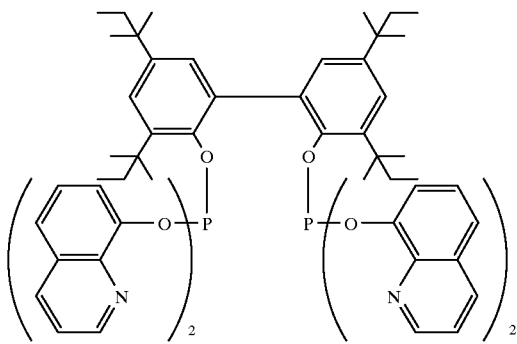
(198)
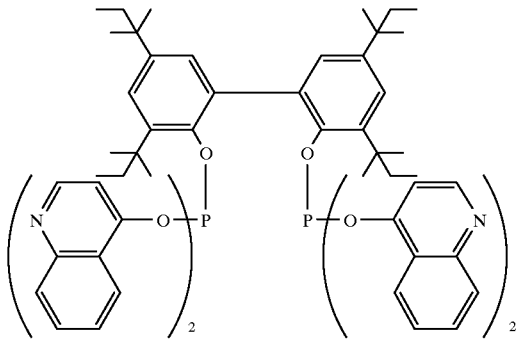
(199)
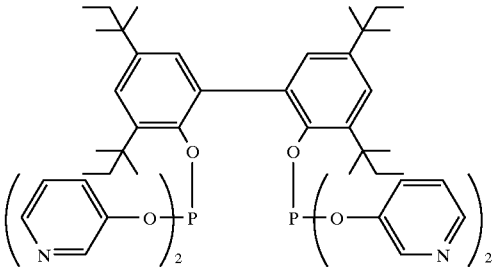
(200)
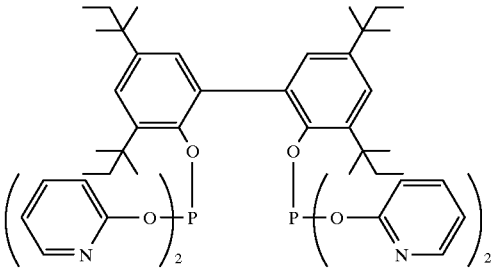
(201)

-continued
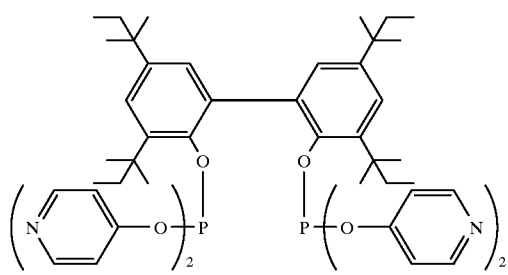
(202)
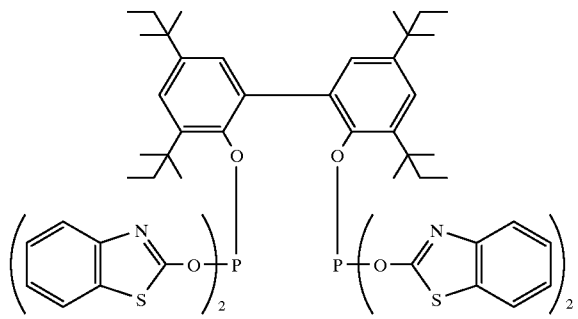
(203)
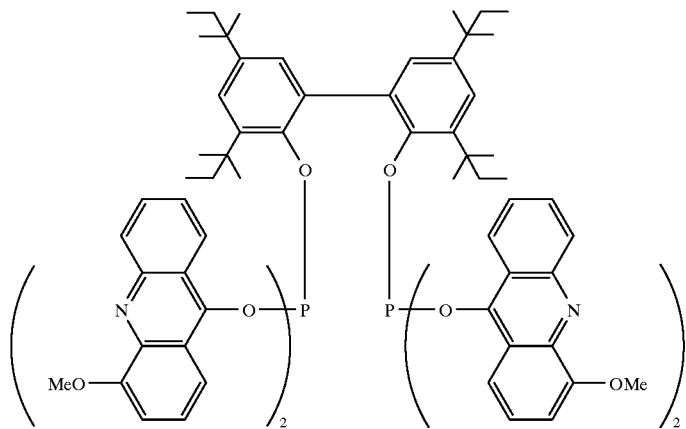
(204)
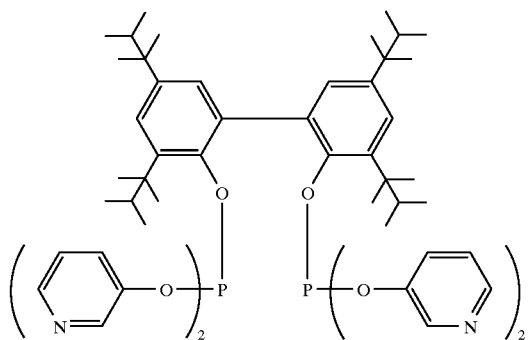
(205)

(206)
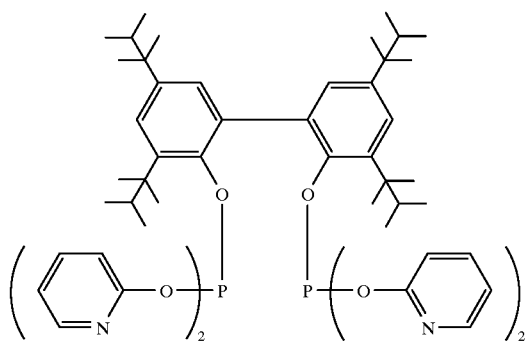
(207)
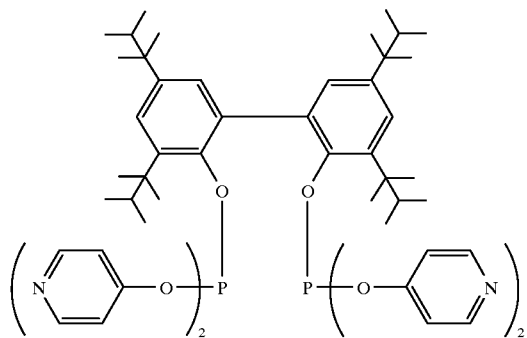
(208)
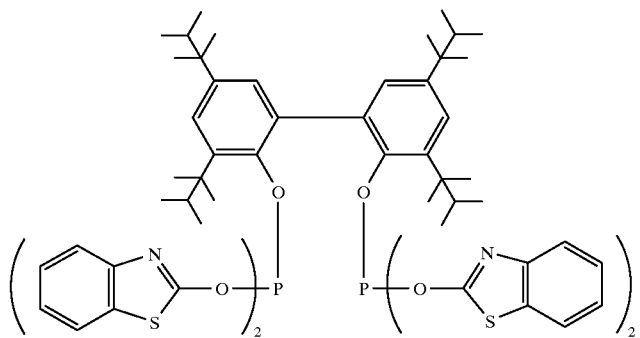
(209)
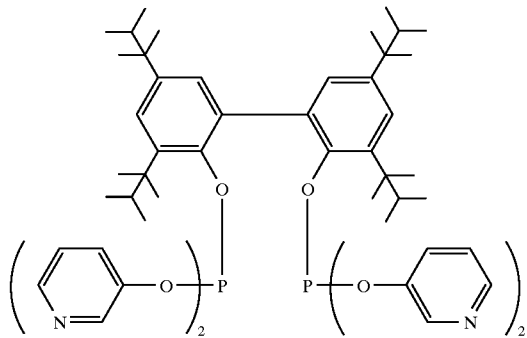

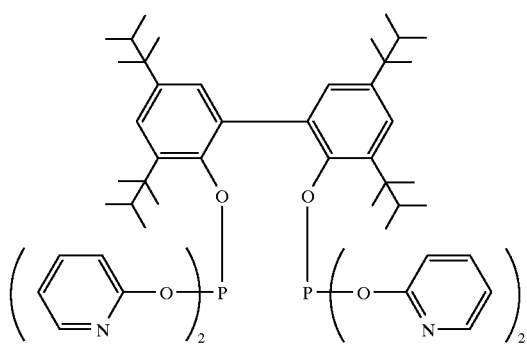
(210)
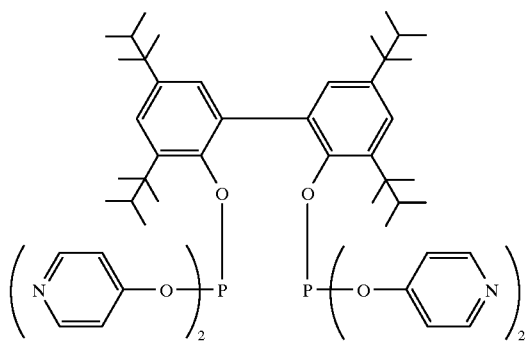
(211)
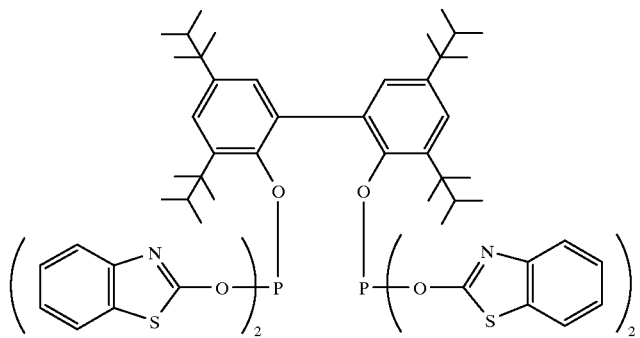
(212)
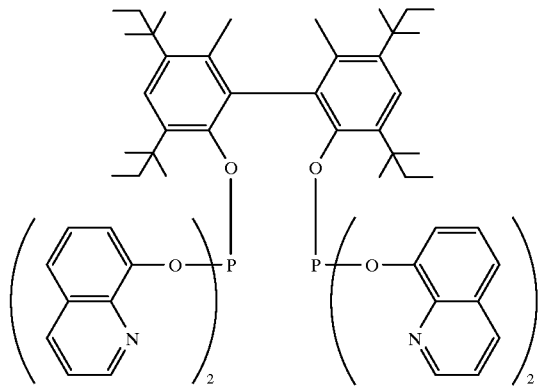
(213)

-continued
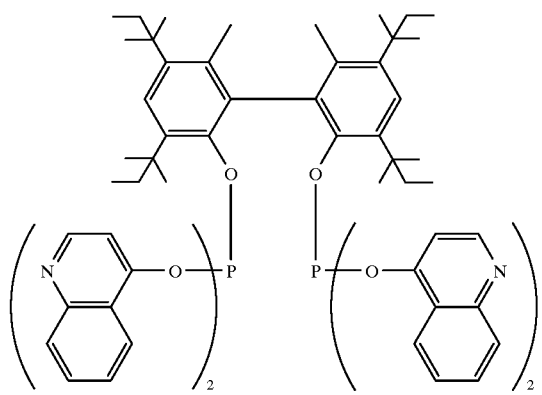
(214)
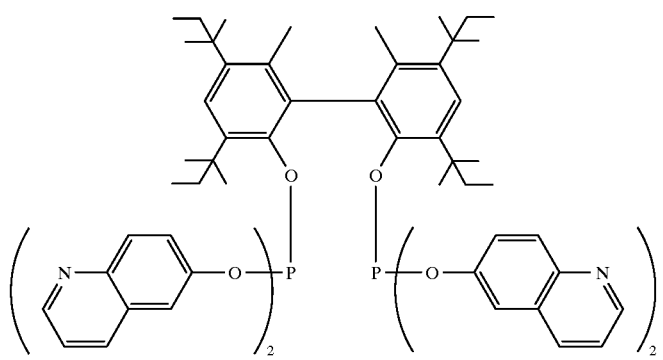
(215)
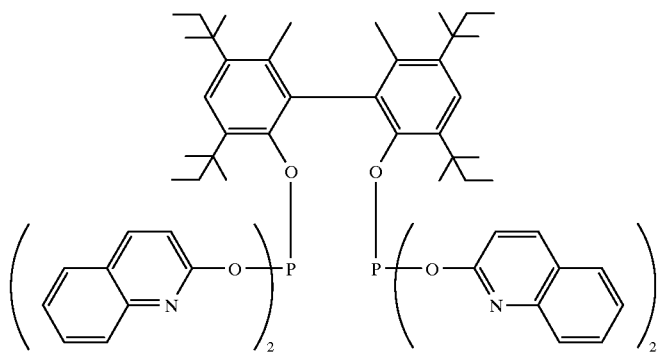
(216)
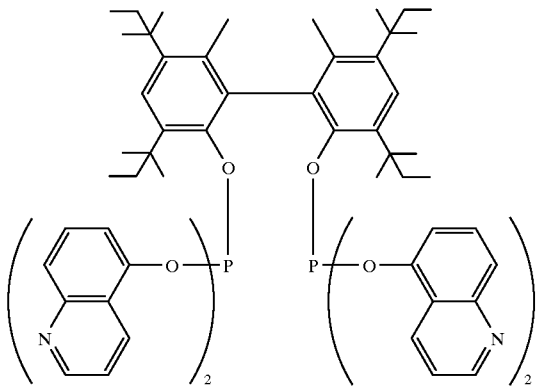
(217)

(218)
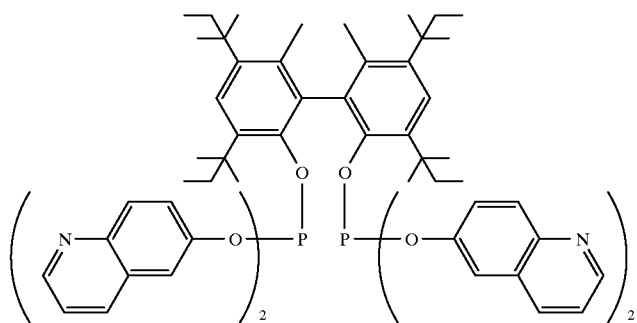
(219)
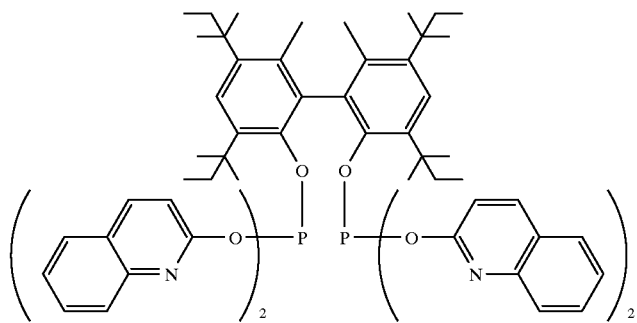
(220)
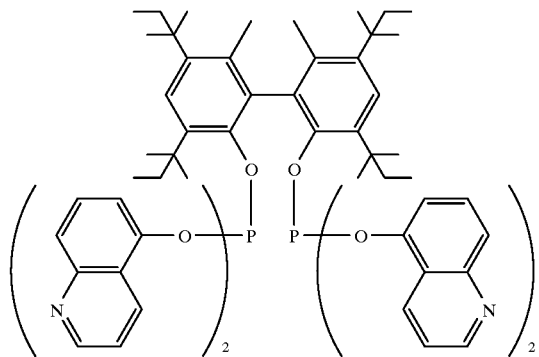
(221)
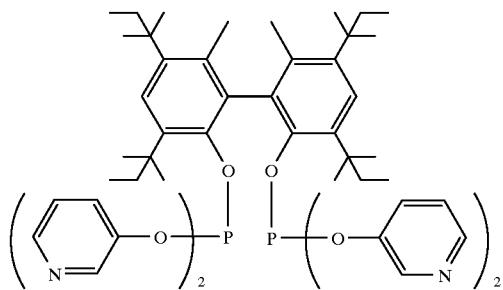

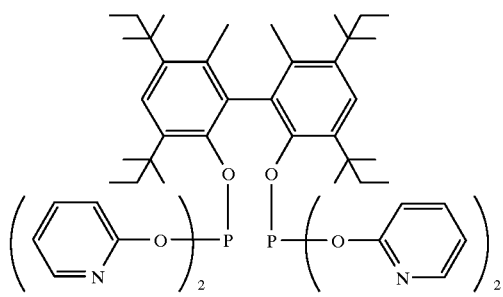
(222)
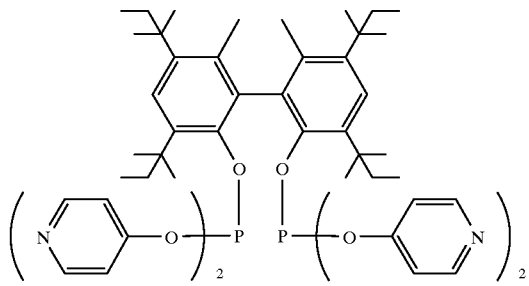
(223)
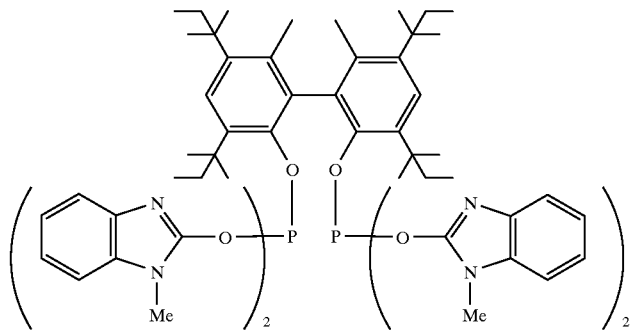
(224)
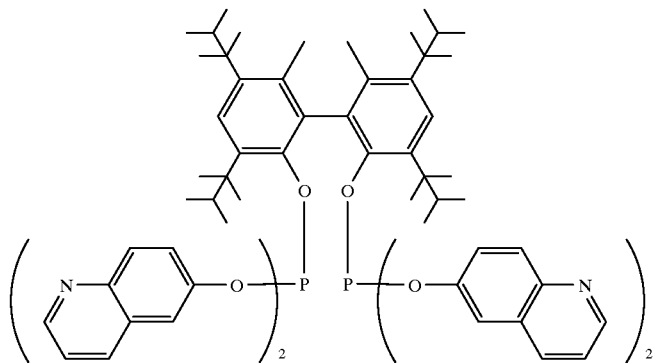
(225)

-continued
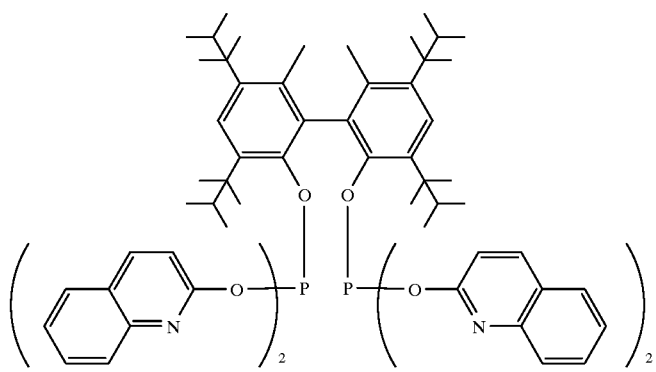
(226)
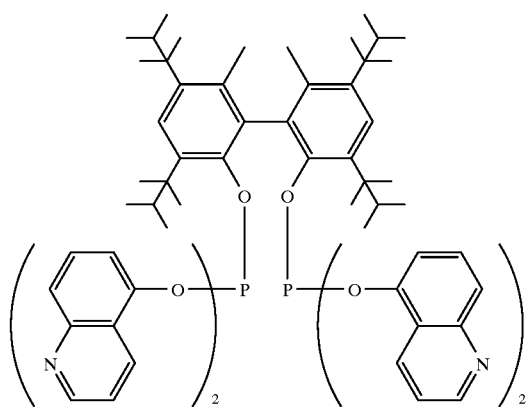
(227)
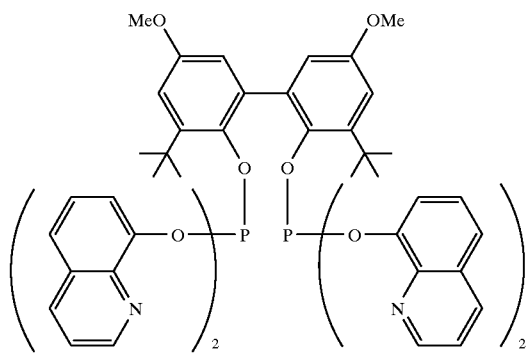
(228)
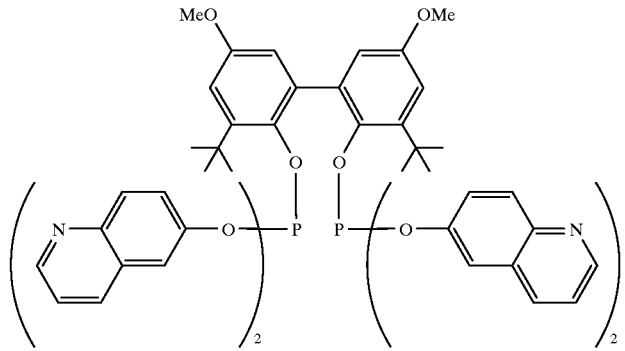
(229)

-continued
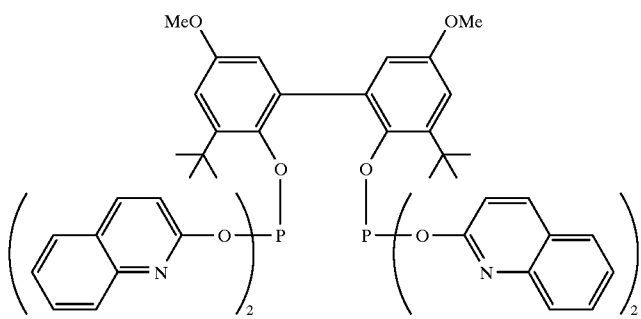
(230)
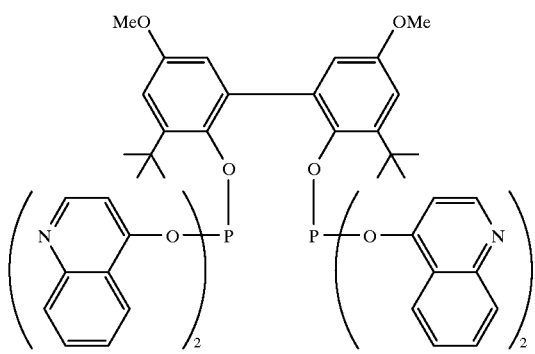
(231)
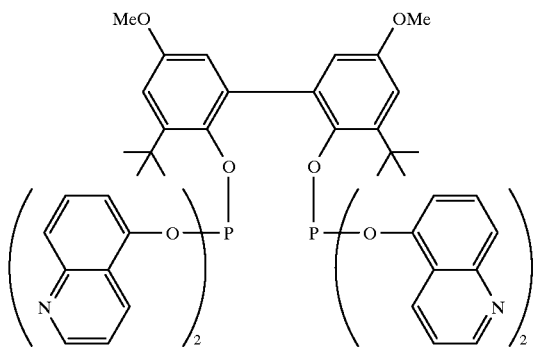
(232)
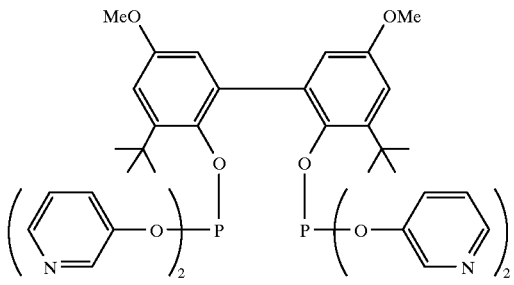
(233)
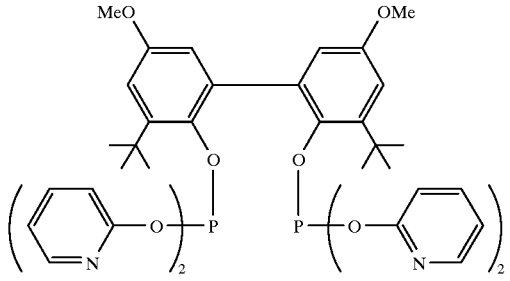
(234)

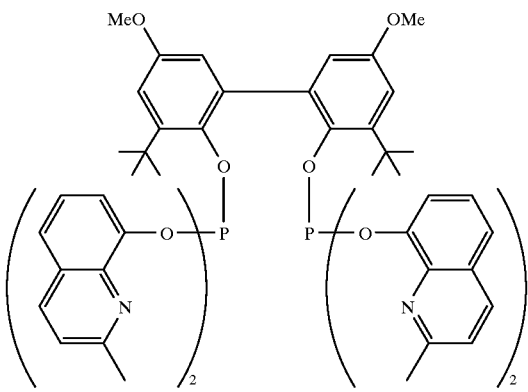
(235)
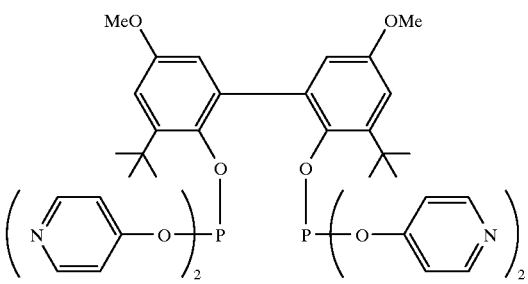
(236)
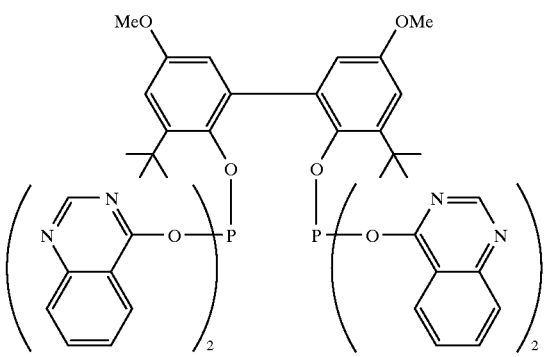
(237)
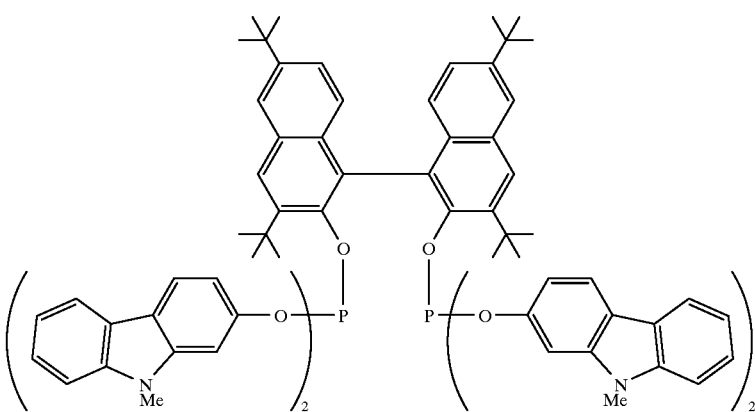
(238)

-continued
(239)
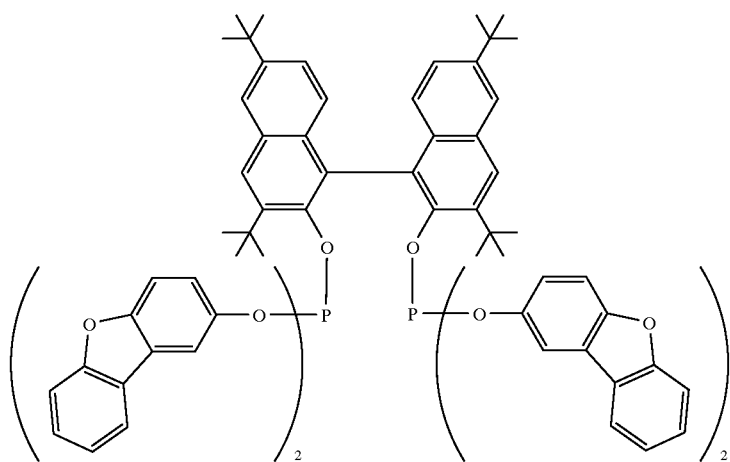
(240)
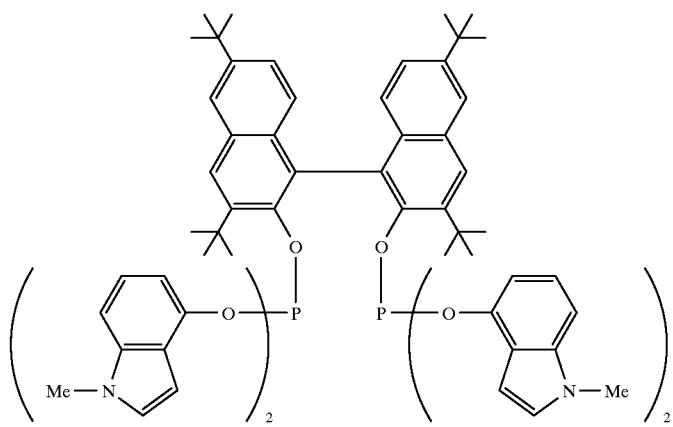
(241)
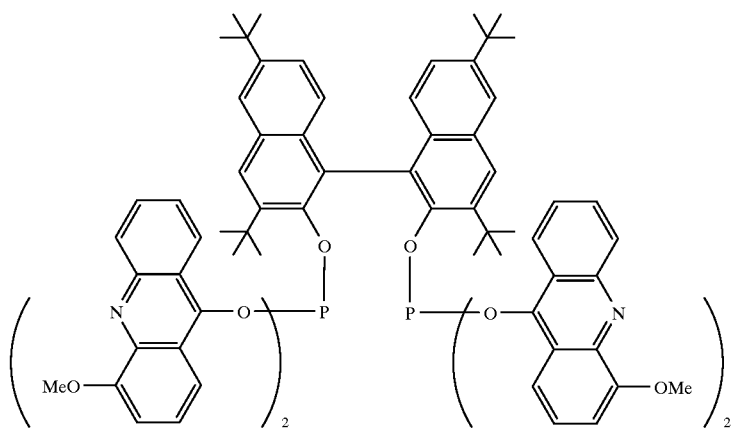

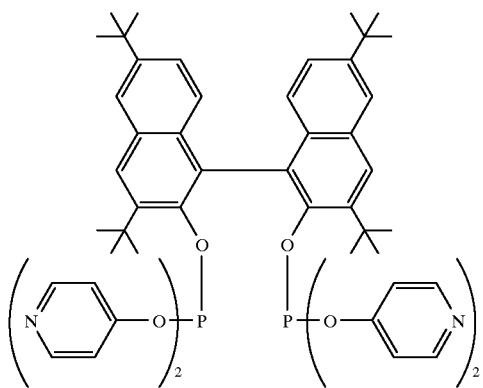
(242)
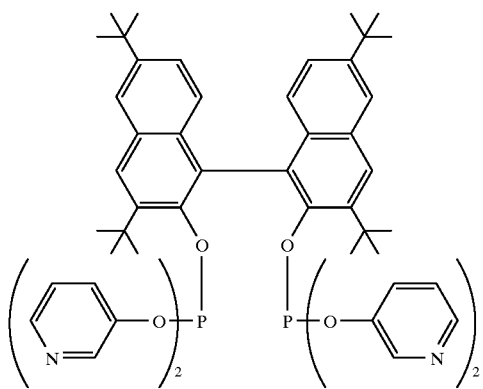
(243)
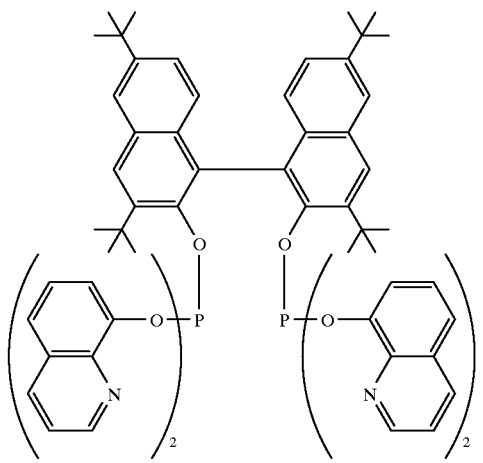
(244)

-continued
(245)
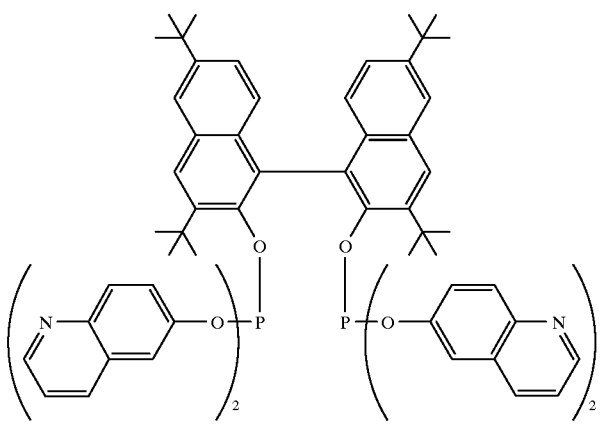
(246)
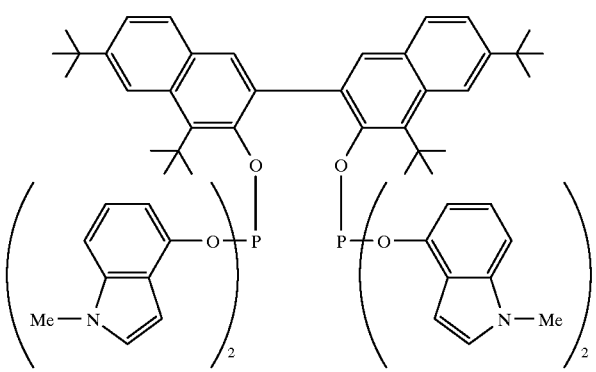
(247)
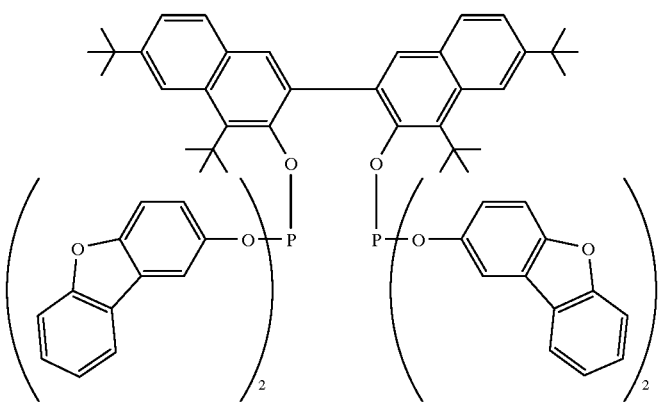
(248)
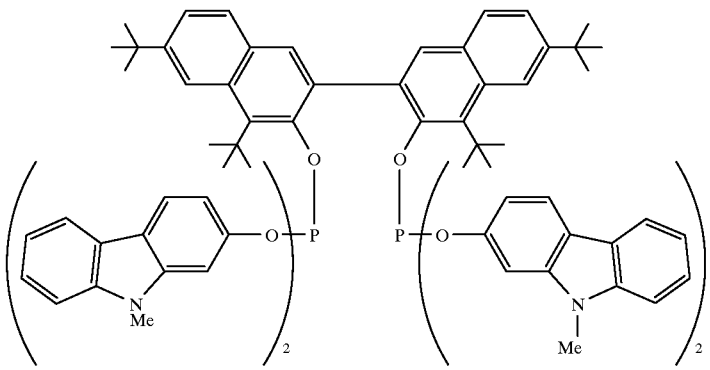

(249)
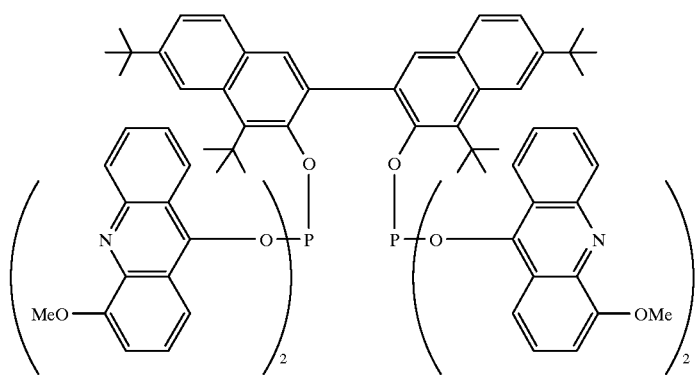
(250)
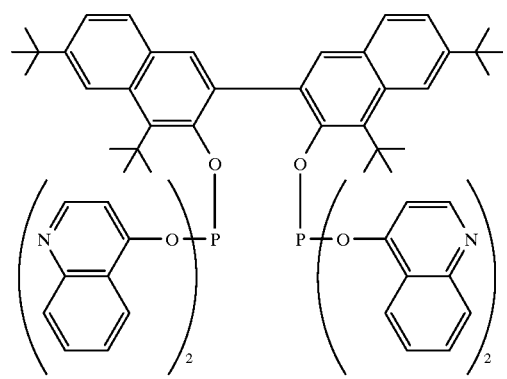
(251)
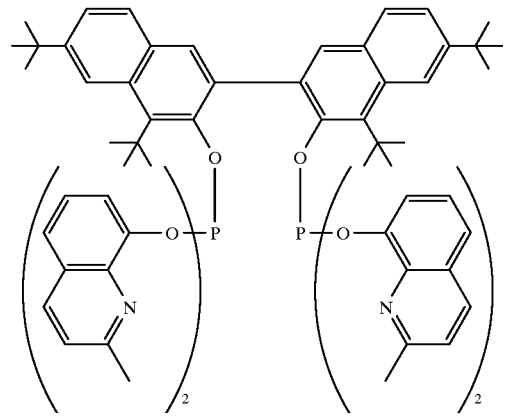
(252)
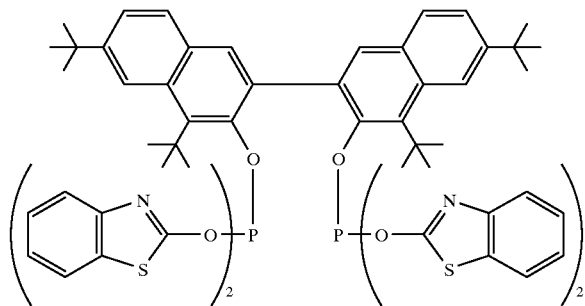

(253)

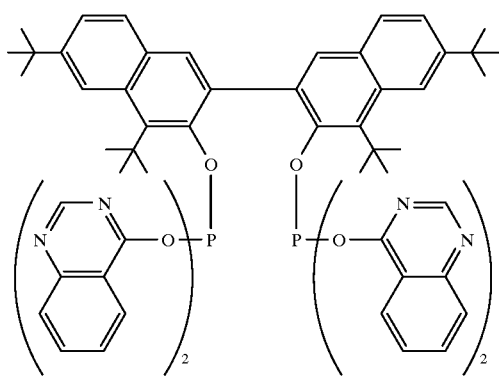

The bisphosphite compound of the above formula (I), (II) or (III) can be prepared by contacting an alkali metal salt or an alkaline earth metal salt of 1,1'-biphenyl-2,2'-diol, 1,1'-binaphthyl-2,2'-diol or 3,3'-binaphthyl-2,2'-diol, each having substituents, represented by the following formula (I-1), (II-1) or (III-1) (in the formula (I-1), (II-1) or (III-1), $R_{11}$ to $R_{14}$, $R_{21}$ to $R_{26}$ or $R_{31}$ to $R_{36}$ are the same as $R_{11}$ to $R_{14}$, $R_{21}$ to $R_{26}$ or $R_{31}$ to $R_{36}$ in the formula (I), (II) or (III), respectively) with a phosphorus compound of the following formula (B-I) and/or (B-II) (wherein $Z_1$ to $Z_4$ are the same as $Z_1$ to $Z_4$ in the formula (A)).

(I-1)

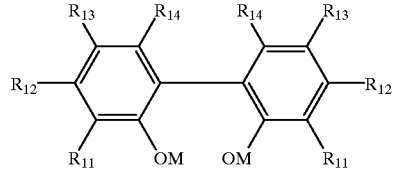

(II-1)

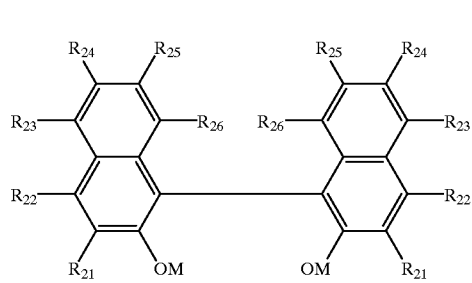

Specific examples of the alcohol component of the diol metal salt represented by each of the above formulae (I-1), (II-1) and (III-1) include 2,2'-biphenyldiol, 3,3'-dimethoxy-5,5'-dimethyl-2,2'-biphenyldiol, 3,3',5,5'-tetramethyl-2,2'-biphenyldiol, 3,3'-di-t-butyl-5,5'-dimethyl-2,2'-biphenyldiol, 3,3', 5,5'-tetra-t-butyl-2,2'-biphenyldiol, 3,3',5,5'-tetra-t-butyl-6,6'-dimethyl-2,2'-biphenyldiol, 3,3',5,5'-tetra-t-pentyl-2,2'-biphenyldiol, 3,3',5,5'-tetra-t-hexyl-2,2'-biphenyldiol, 3,3 1-di-t-butyl-5,5'-dimethoxy-2,2'-biphenyldiol, 3,3'-di-t-butyl-5,5'-diethoxy-2,2'-biphenyldiol, 3,3'-di-t-butyl-5,5'-di-t-butoxy-2,2'-biphenyldiol, 3,3',5,5'-tetracyclooctyl-2,2'-biphenyldiol, 1,1'-binaphthyl-2,2'-diol, 3,3'-binaphthyl-2,2'-diol, 3,3',6,6'-tetra-t-butyl-1,1'-binaphthyl-2,2'-diol, and 1,1',7,7'-tetra-t-butyl-3,3'-binaphthyl-2,2'-diol.

The bisarylene diol salt represented by the above formula (I-1), (II-1) or (III-1) can be synthesized by reacting 1,1'-biphenyl-2,2'-diol, 1,1'-binaphthyl-2,2'-diol or 3,3'-binaphthyl-2,2'-diol, each having the respective substituents, represented by the following formula (I-2), (II-2) or (III-2) (wherein $R_{11}$ to $R_{14}$, $R_{21}$ to $R_{26}$ or $R_{31}$ to $R_{36}$ are the same as $R_{11}$ to $R_{14}$, $R_{21}$ to $R_{26}$ or $R_{31}$ to $R_{36}$ in the formula (I), (II) or (III), respectively) with an alkali metal compound such as n-BuLi, Na, NaH or KH, or an alkaline earth metal compound such as methyl magnesium bromide or ethyl magnesium bromide in a solvent, preferably in an atmosphere of inert gas such as nitrogen.

(I-2)

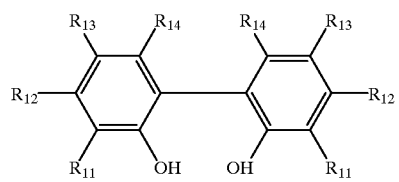

(II-2)

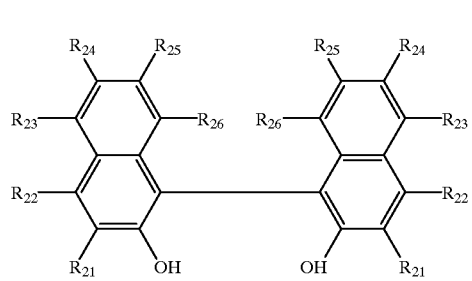

(III-2)

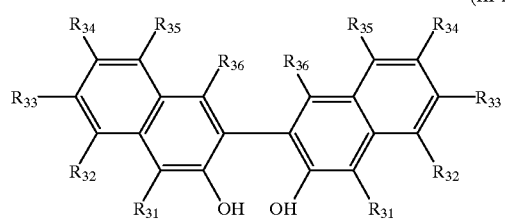

The amount of the above metal compound is usually sufficient at a level of 2 mols per mol of the bisarylene diol of the formula (I-2), (II-2) or (III-2). However, if desired, a larger amount may be employed. As the solvent, an ether such as tetrahydrofuran or diethyl ether, a hydrocarbon such as hexane or toluene, a nitrogen-containing compound such as pyridine, triethylamine or N,N,N',N'- tetramethylethylenediamine or a mixture thereof, may suitably be used. The reaction temperature can be suitably selected within a range of from −70° C. to the boiling point of the solvent, preferably from −70° C. to 20° C. A method may also be employed wherein at the initial stage of the reaction, a low temperature such as from −30° C. to 10° C. is employed, and then the temperature is gradually raised to the boiling point of the solvent. From the viewpoint of the reaction operation, it is preferred to carry out the reaction by using n-BuLi or NaH as the metal compound and tetrahydrofuran as the solvent. The reaction time can be selected usually within a range of from 1 minute to 48 hours, preferably from 10 minutes to 4 hours.

The compound of the formula (I-1), (II-1) or (III-1) may be used for the subsequent step without purification i.e. in the form of the reaction solution. However, it may be subjected to pretreatment such as washing with a poor solvent or isolation by recrystallization.

The phosphorus compound represented by the formula (B-I) or (B-II) can be synthesized usually by reacting phosphorus trichloride ($PCl_3$) with a phenol or a hydroxyheteroaromatic compound represented by $Z_1$—OH, $Z_2$—OH, $Z_3$—OH or $Z_4$—OH, wherein $Z_1$ to $Z_4$ are the same as $Z_1$ to $Z_4$ in the formula (A), in the presence or absence of a base, preferably in an atmosphere of inert gas such as nitrogen, in a solvent or without using a solvent. A phosphorus compound wherein $Z_1$ and $Z_2$, or $Z_3$ and $Z_4$, are the same, is preferred, since such a compound can readily be synthesized. Accordingly, more preferred is a case where $Z_1$ and $Z_2$ and $Z_3$ and $Z_4$, are respectively the same. Most preferred is a case wherein $Z_1$, $Z_2$, $Z_3$ and $Z_4$, are all the same.

The base to be used for producing the above phosphorus compound may, for example, be a nitrogen-containing base such as pyridine, triethylamine or diethylamine, or an inorganic base such as sodium carbonate or potassium carbonate. From the viewpoint of the reaction operation efficiency, a nitrogen-containing base is preferably employed. The amount of the base is usually 2 mols per mol of $PCl_3$. If the amount of the base is too large or too small, the amount of unnecessary by-products, such as phosphites such as $P(OZ_1)_2(OZ_2)$, $P(OZ_1)(OZ_2)_2$, $P(OZ_1)_3$ and $P(OZ_2)_3$ or dichloro compounds such as $Cl_2P(OZ_1)$, increases, such being undesirable.

The reaction temperature can be optionally selected. However, when a nitrogen-containing base is used as the base, it is preferred to carry out the reaction at a temperature of from 0 to 5° C. The reaction time can be selected within a range of from 1 minute to 48 hours. However, a reaction time of from 5 minutes to 10 hours is preferred.

When the reaction is carried out in the presence of a base, a salt of the base with hydrogen chloride produced as a by-product, as the reaction proceeds, will usually be present as solid in the reaction solution, but such a salt can be removed from the reaction system by a method such as filtration, preferably, in an atmosphere of inert gas such as nitrogen. When the reaction is carried out in the absence of a base, hydrogen chloride produced as a by-product can be removed from the reaction system, for example, by bubbling inert gas such as nitrogen gas or argon gas in the reaction system.

The chlorodiaryloxyphosphine of the formula (B-I) or (B-II) may sometimes be obtained as a mixture with a above-mentioned unnecessary phosphites and dichloro compounds, and may be used for the next step without separating it from such by-products. As a method for separating the phosphorus compound of the formula (B-I) or (B-II) from these by-products, distillation or a method of recrystallization employing an aliphatic hydrocarbon solvent such as hexane or heptane, may be mentioned.

A mixture of phosphites such as $P(OZ_1)_3$, monochloro compounds such as $ClP(OZ_1)_2$, dichloro compounds such as $Cl_2P(OZ_1)$, and $PCl_3$ may be obtained during the synthesis of the phosphorus compound represented by the formula (B-I) or (B-II). In such a case, a method of disproportionation may be employed wherein the temperature of the reaction solution is kept at or below the boiling point of the solvent optionally in the presence of a catalyst described below, because the yield of the desired monochloro compounds may increase by a disproportionation. Further, monochloro compounds such as $ClP(OZ_1)_2$ may be synthesized by mixing $PCl_3$ and $P(OZ_1)_3$, preferably with the molar ratio of $PCl_3/P(OZ_1)_3=0.5$, with or without heating of the reaction solution, where $\epsilon$-caprolactam may be used as a catalyst. As the disproportionation catalyst, acid amide disclosed in JP-A-52-42822, phosphonium salt disclosed in JP-A-52-42823, phosphine, or phosphine oxide disclosed in JP-A-53-23930 may also be employed.

The bisphosphite compound of the formula (I), (II) or (III) can be synthesized by contacting a compound of the formula (I-1), (II-1) or (III-1) with a compound of the formula (B-I), and/or (B-II) in a solvent or in the absence of a solvent at a temperature of at most 20° C. for at least 1 minute. The contact is preferably carried out in an atmosphere of inert gas such as nitrogen, and the desired bisphosphite compound can be synthesized by a method wherein a compound of the formula (I-1), (II-1) or (III-1) is mixed with the compound of the formula (B-I) and/or (B-II), preferably at a temperature of at most 0° C., more preferably at most −30° C., most preferably at most −50° C., the temperature is maintained at that level for at least 1 minute, preferably from 3 minutes to 60 minutes, and then the temperature is gradually raised. The temperature raising rate can be suitably selected within a range of from 0.1° C./min to 20° C./min. However, a temperature raising rate of from 0.5° C./min to 10° C./min is preferred. The solvent for the reaction may, for example, be an ether such as tetrahydrofuran, diethyl ether or dioxane, a hydrocarbon such as hexane or toluene, a nitrogen-containing compound such as pyridine, triethylamine or N,N,N',N'-tetramethylethylenediamine, or a mixture thereof. The amount of the solvent is preferably the minimum amount required for dissolving the desired product, but may be larger than the minimum amount.

As a method for purifying the bisphosphite compound of the formula (I), (II) or (III), a method by column chromatography, a method by suspension washing or a method by recrystallization may, for example, be mentioned.

As the method by column chromatography, a method wherein silica gel, alumina oxide or the like is used as the packing material, may be mentioned. The developing solution for the column may, for example, be an ether such as tetrahydrofuran or dioxane, an aliphatic hydrocarbon such as hexane or heptane, an aromatic hydrocarbon such as toluene or xylene, a halogenated hydrocarbon such as chloroform or dichloromethane, an ester such as ethyl acetate or methyl acetate. Such a solution may be composed of a single solvent or a mixture of two or more solvents, so that it is suitable for purification of the desired product.

As the purification method by suspension washing, a method may be mentioned wherein after completion of the reaction for synthesis of a bisphosphite, a metal chloride (MCl) produced as a by-product is removed from the reaction solution by filtration or by a polar solvent such as water, then the solution is evaporated to dryness, and the residue is stirred in a solvent, e.g. an aliphatic hydrocarbon such as acetonitrile, hexane or heptane, a ketone such as acetone or diethyl ketone or an alcohol such as methanol or ethanol, so that the unnecessary by-products are dissolved in the solvent without dissolving the desired product in the solvent, whereby the desired product can be purified.

As the purification by recrystallization, a method may be mentioned wherein after completion of the reaction for the synthesis of a bisphosphite, a metal chloride produced as a by-product, is removed from the reaction solution by filtration or by a polar solvent such as water, then the solution is evaporated to dryness, the residue is dissolved in a solvent of the minimum amount required for dissolving the residue, followed by cooling, or after dissolving the residue in a solvent capable of dissolving it, a solvent in which the desired bisphosphite compound is insoluble or hardly soluble, is added, followed by cooling, if necessary, to precipitate a solid, which is then separated by a method such as filtration and further washed with a solvent in which the solid is insoluble. The solvent in which the bisphosphite compound is soluble, may, for example, be an aromatic hydrocarbon such as benzene, toluene or xylene, or an ether such as tetrahydrofuran or dioxane, and the solvent in which it is hardly soluble, may, for example, be an aliphatic hydrocarbon such as hexane or heptane, a ketone such as acetone or diethyl ketone, or an alcohol such as methanol or ethanol, in addition to acetonitrile.

The synthetic method employing the compound of the formula (B) is effective in a case where sterically bulky substituents such as t-butyl groups are present on carbon atoms adjacent to the carbon atom bonded to the oxygen atom in the bisarylene group in the above formula (A), and it is particularly effective in a case where the two oxygen atoms bonded to the bisarylene group of the formula (I), (II) or (III) are spatially close to each other, and sterically bulky substituents such as t-butyl groups are substituted on carbon atoms adjacent to the carbon atom bonded to the oxygen atoms in the bisarylene group.

In the present invention, it is possible to simultaneously satisfy a high reaction rate and excellent selectivity for the desired product by carrying out the hydroformylation reaction by means of the above-mentioned novel bisphosphite compound.

The olefinic compound to be used as the starting material in the hydroformylation reaction of the present invention, is not particularly limited, so long as it is an organic compound having at least one olefinic double bond in its molecule. Specifically, it may, for example, be ethylene, propylene, butene, butadiene, pentene, hexene, hexadiene, octene, octadiene, decene, hexadecene, octadecene, eicosene, docosene, styrene, α-methylstyrene, cyclohexene, a lower olefin mixture such as a propylene/butene mixture, a 1-butene/2-butene/isobutylene mixture or a 1-butene/2-butene/isobutylene/butadiene mixture, an olefinic hydrocarbon such as a mixture of olefin oligomer isomers such as dimer to tetramer of a lower olefin such as propylene, n-butene or isobutylene, or a polar group-substituted olefin such as acrylonitrile, allyl alcohol, 1-hydroxy-2,7-octadiene, 3-hydroxy-1,7-octadiene, oleyl alcohol, 1-methoxy-2,7-octadiene, methyl acrylate, methyl methacrylate or methyl oleate.

The Group VIII metal compound as the catalyst or its precursor for the hydroformylation reaction, may, for example, be a hydride, a halide, an organic salt, an inorganic salt, an oxide, a carbonyl compound, an amine compound, an olefine-coordinated compound, a phosphine-coordinated compound or a phosphite-coordinated compound of a Group VIII metal. For example, it may be a ruthenium compound such as ruthenium trichloride, tetraamminehydroxychlororuthenium chloride or dichlorotris(triphenylphosphine) ruthenium, a palladium compound such as palladium acetate or palladium chloride, an osmium compound such as osmium trichloride, an iridium compound such as iridium trichloride or iridium carbonyl, a platinum compound such as platinic acid, sodium hexachloroplatinate or potassium platinate, or a cobalt compound such as dicobalt octacarbonyl or cobalt stearate, or a rhodium compound such as rhodium trichloride, rhodium nitrate, rhodium acetate, $Rh(acac)(CO)_2$, $[Rh(OAc)(COD)]_2$, $Rh_4(CO)_{12}$, $Rh_6(CO)_{16}$, $HRh(CO)(PPh_3)_3$, $[Rh(OAc)(CO)_2]_2$, $[Rh(\mu\text{-}S(t\text{-}Bu))(CO)_2]_2$ or $[RhCl(COD)]_2$ wherein acac represents an acetylacetonate group, Ac an acetyl group, COD 1,5-cyclooctadiene, Ph a phenyl group and t-Bu a t-butyl group. However, the Group VIII metal compound is not limited to such specific examples.

In the process of the present invention, the bisphosphite compound may be used as preliminarily permitted to form a complex with the above Group VIII metal compound. The Group VIII metal complex containing the bisphosphite compound can readily be prepared by a conventional method for forming a complex from a Group VIII metal compound and the bisphosphite compound. In some cases, the Group VIII metal compound and the bisphosphite compound may be supplied to the hydroformylation reaction zone to form the complex there.

The amount of the Group VIII metal compound is not particularly limited, and there is a limit from the viewpoint of the catalytic activity and the economical feasibility. It is usually selected so that the concentration in the hydroformylation reaction zone is within a range of from 0.05 mg to 5 g, preferably from 0.5 mg to 1 g, per l of the solvent for the reaction or the olefinic compound, as calculated as the metal.

The amount of the bisphosphite compound of the present invention is not particularly limited, and it is suitably set so that good results are obtainable with respect to the catalytic activity and the selectivity. It is selected usually within a range of from about 0.001 to 500 mols, preferably from 0.1 to 100 mols, per mol of the Group VIII metal.

Use of a solvent for the reaction is not essential for the hydroformylation reaction. However, a solvent inert to the hydroformylation reaction may be used as the case required. Specific examples of preferred solvents include aromatic hydrocarbon compounds such as toluene, xylene and dodecylbenzene, ketones such as acetone, diethyl ketone and methyl ethyl ketone, ethers such as tetrahydrofurane and dioxane, esters such as ethyl acetate and di-n-octyl-phthalate, high boiling components produced as by-products during the hydroformylation reaction, such as condensation products of aldehyde, and the olefinic compound as the material for the reaction.

The reaction conditions for the hydroformylation in the present invention may be the same as commonly employed theretofore. Namely, the reaction temperature is selected usually within a range of from 15 to 200° C., preferably from 50 to 150° C., and the CO partial pressure and the $H_2$ partial pressure are selected usually within a range of from 0.001 to 200 atm, preferably from 0.1 to 100 atm, more preferably from 1 to 50 atm. The molar ratio of hydrogen to carbon monoxide ($H_2/CO$) is selected usually within a range of from 10/1 to 1/10, preferably from 1/1 to 1/6. The hydroformylation reaction system may be a continuous system, or a batch system which may be conducted, for example, in an agitation type reactor or a bubbling column type reactor.

In a hydroformylation reaction system where the novel bisphosphite compound of the formula (I), (II) or (III) of the present invention is employed, after separating the formed aldehyde by a method such as distillation, a recovered solution containing the Group VIII metal and the bisphosphite compound may be used to further conduct the hydroformylation reaction of an olefinic compound. Further, in a case where the olefinic compound is continuously converted to aldehyde, a part or whole of the resulting aldehyde is separated, and the residual liquid may be continuously recycled to the hydroformylation reactor.

Now, the present invention will be described in further detail with reference to Examples. However, it should be understood that the present invention is by no means restricted by such specific Examples.

Preparation of Bisphosphite Compounds

EXAMPLE 1

A toluene (about 200 ml) solution of phenol (6.36 g, 67.6 mmol) and pyridine (5.35 g, 67.6 mmol) was dropwise added to a toluene (about 400 ml) solution of phosphorus trichloride (4.64 g, 33.8 mmol) in a nitrogen atmosphere at 0° C. over a period of about 2.5 hours with stirring. Then, by-product solid pyridine hydrochloride was filtered off, and then the filtrate was concentrated to about 50 ml by distilling of the solvent, to obtain a toluene solution containing $ClP(OPh)_2$. On the other hand, n-butyl lithium (20.1 ml, 33.8 mmol) dissolved in hexane, was dropwise added to a tetrahydrofuran (about 50 ml) solution of 3,3',5,5'-tetra-t-butyl-2,2'-biphenyldiol (6.94 g, 16.9 mmol) in a nitrogen atmosphere at 0° C., followed by boiling and refluxing for about 1 hour, to obtain a dilithium salt of 3,3',5,5'-tetra-t-butyl-2,2'-biphenyldiol. Then, the dilithium salt of 3,3',5,5'-tetra-t-butyl-2,2'-biphenyldiol dissolved in tetrahydrofuran, was dropwise added to the previous toluene solution containing $ClP(OPh)_2$ in a nitrogen atmosphere at –70° C. over a period of 30 minutes with stirring. After the dropwise addition, the reaction solution was returned to 0° C. at a temperature raising rate of about 1.2° C./min. Then, by-product solid LiCl was filtered off, and the filtrate was subjected to vacuum distillation to obtain the residual liquid. This liquid was subjected to silica gel column chromatography (developer: toluene/hexane=about 1/5) to obtain a solution containing bisphosphite (1) only, and the solvent was distilled off under reduced pressure to obtain 3.06 g (yield: 21.5%) as a colorless solid powder.

EXAMPLE 2

3.88 g (yield: 27.2%) of bisphosphite (2) was obtained as a white solid powder in the same manner as in Example 1 except that 2-methylphenol (6.87 g, 59.9 mmol) was used instead of phenol (6.36 g, 67.6 mmol), phosphorus trichloride was 4.36 g (31.8 mmol), pyridine was 5.02 g (59.9 mmol), 3,3',5,5'-tetra-t-butyl-2,2'-biphenyldiol was 6.52 g (15.9 mmol), n-butyl lithium dissolved in hexane was 18.8 ml (31.8 mmol), and the mixing ratio of the developer for the silica gel column chromatography was changed to toluene/hexane=about 1/10.

EXAMPLE 3

1.96 g (yield: 12.5%) of bisphosphite (3) was obtained as a colorless oily liquid in the same manner as in Example 1 except that 3-methylphenol (7.54 g, 69.7 mmol) was used instead of phenol (6.36 g, 67.6 mmol), phosphorus trichloride was 4.79 g (34.9 mmol), pyridine was 5.51 g (71.8 mmol), 3,3',5,5'-tetra-t-butyl-2,2'-biphenyldiol was 7.16 g (17.4 mmol), n-butyl lithium dissolved in hexane was 20.6 ml (34.9 mmol), and the mixing ratio of the developer for the silica gel column chromatography was changed to toluene/hexane=about 1/4.

EXAMPLE 4

2.04 g (yield: 14.5%) of bisphosphite (4) was obtained as a colorless oily liquid in the same manner as in Example 1 except that 4-methylphenol (6.76 g, 62.6 mmol) was used instead of phenol (6.36 g, 67.6 mmol), phosphorus trichloride was 4.30 g (31.3 mmol), pyridine was 4.95 g (62.6 mmol), 3,3',5,5'-tetra-t-butyl-2,2'-biphenyldiol was 6.42 g (15.6 mmol), n-butyl lithium dissolved in hexane was 18.5 ml (31.3 mmol), and the mixing ratio of the developer for the silica gel column chromatography was changed to toluene/hexane=about 1/4.

EXAMPLE 5

1.80 g (yield: 10.5%) of bisphosphite (5) was obtained as a white solid powder in the same manner as in Example 1 except that 2,5-dimethylphenol (8.77 g, 71.8 mmol) was used instead of phenol (6.36 g, 67.6 mmol), phosphorus trichloride was 4.93 g (35.9 mmol), pyridine was 5.68 g (71.8 mmol), 3,3',5,5'-tetra-t-butyl-2,2'-biphenyldiol was 7.37 g (18.0 mmol), and n-butyl lithium dissolved in hexane was 21.2 ml (35.9 mmol).

EXAMPLE 6

4.24 g (yield: 20.8%) of bisphosphite (6) was obtained as a white solid powder in the same manner as in Example 1 except that 3,5-dimethylphenol (8.81 g, 72.1 mmol) was used instead of phenol (6.36 g, 67.6 mmol), phosphorus trichloride was 4.95 g (36.1 mmol), pyridine was 5.71 g (72.1 mmol), 3,3',5,5'-tetra-t-butyl-2,2'-biphenyldiol was 7.40 g (18.0 mmol), n-butyl lithium dissolved in hexane was 21.3 ml (36.1 mmol), and the mixing ratio of the developer for the silica gel column chromatography was changed to toluene/hexane=about 1/4.

EXAMPLE 7

2.16 g (yield: 12.0%) of bisphosphite (7) was obtained as a white solid powder in the same manner as in Example 1 except that 4-phenylphenol (10.80 g, 63.4 mmol) was used instead of phenol (6.36 g, 67.6 mmol), phosphorus trichloride was 4.36 g (31.7 mmol), pyridine was 5.02 g (63.4 mmol), 3,3',5,5'-tetra-t-butyl-2,2'-biphenyldiol was 6.51 g (15.9 mmol), n-butyl lithium dissolved in hexane was 18.8 ml (31.7 mmol), and the mixing ratio of the developer for the silica gel column chromatography was changed to toluene/hexane=about 1/3.

EXAMPLE 8

2.50 g (yield: 14.6%) of bisphosphite (8) was obtained as a white solid powder in the same manner as in Example 1 except that 2-naphthol (9.44 g, 65.5 mmol) was used instead of phenol (6.36 g, 67.6 mmol), phosphorus trichloride was 4.50 g (32.8 mmol), pyridine was 5.18 g (65.5 mmol), 3,3',5,5'-tetra-t-butyl-2,2'-biphenyldiol was 6.73 g (16.4 mmol), and n-butyl lithium dissolved in hexane was 19.4 ml (21.8 mmol).

EXAMPLE 9

6.90 g (yield: 37.2%) of bisphosphite (9) was obtained as a white solid powder in the same manner as in Example 1 except that 1-naphthol (10.26 g, 71.1 mmol) was used instead of phenol (6.36 g, 67.6 mmol), phosphorus trichloride was 4.88 g (35.6 mmol), pyridine was 5.63 g (71.1 mmol), 3,3',5,5'-tetra-t-butyl-2,2'-biphenyldiol was 7.30 g (17.8 mmol), and n-butyl lithium dissolved in hexane was 21.0 ml (35.6 mmol).

EXAMPLE 10

0.9 g (yield: 12.1%) of bisphosphite (10) was obtained as a white solid powder in the same manner as in Example 1 except that 2-methylphenol (3.47 g, 32.0 mmol) and 3,3',5,5'-tetra-t-butyl-6,6'-dimethyl-2,2'-biphenyldiol (3.51 g, 8.0 mmol) were used instead of phenol (6.36 g, 67.6 mmol) and 3,3',5,5'-tetra-t-butyl-2,2'-biphenyldiol (6.94 g, 16.9 mmol), phosphorus trichloride was 2.20 g (16.0 mmol), pyridine was 2.53 g (32.0 mmol), n-butyl lithium dissolved in hexane was 9.5 ml (16.0 mmol), and the mixing ratio of the developer for the silica gel column chromatography was changed to toluene/hexane=about 1/10.

EXAMPLE 11

6.3 g (yield: 36.9%) of bisphosphite (11) was obtained as a white solid powder in the same manner as in Example 1 except that 1-naphthol (9.18 g, 63.6 mmol) and 3,3',5,5'-tetra-t-butyl-6,6'-dimethyl-2,2'-biphenyldiol (6.98 g, 15.9 mmol) were used instead of phenol (6.36 g, 67.6 mmol) and 3,3',5,5'-tetra-t-butyl-2,2'-biphenyldiol (6.94 g, 16.9 mmol), phosphorus trichloride was 4.37 g (31.8 mmol), pyridine was 5.03 g (63.6 mmol), and n-butyl lithium dissolved in hexane was 18.8 ml (31.8 mmol).

EXAMPLE 12

A toluene (about 340 ml) solution of 2-naphthol (25.00 g, 173.5 mmol) and pyridine (13.72 g, 173.5 mmol) was dropwise added to a toluene (about 170 ml) solution of phosphorus trichloride (11.92 g, 86.8 mmol) in a nitrogen atmosphere at 0° C. over a period of about 1.0 hour with stirring. Then, by-product solid pyridine hydrochloride was filtered off. Then, the solvent was distilled off, and the residue was dried under reduced pressure to obtain a white solid (30 g). This solid was dissolved under heating in 300 ml of hexane, followed by cooling to room temperature to purify chloro-di-2-naphthyloxy phosphine (purity: 98.8%, 16.9 g). On the other hand, n-butyl lithium dissolved in hexane (21.9 ml, 37.0 mmol) was dropwise added to a tetrahydrofuran (100 ml) solution of 3,3 ,6,6'-tetra-t-butyl-1,1'-binaphthyl-2,2'-diol (9.00 g, 17.6 mmol) in a nitrogen atmosphere at room temperature, followed by boiling and refluxing for about 12 hours. Then, the mixture was left to cool to room temperature. Then, the supernatant was discarded, and the precipitate was washed three times with tetrahydrofuran and dried under reduced pressure to obtain a dilithium salt of 3,3',6,6'-tetra-t-butyl-1,1'-binaphthyl-2,2'-diol as a slightly yellow solid. Then, the dilithium salt of 3,3',6,6'-tetra-t-butyl-1,1'-binaphthyl-2,2'-diol (2.11 g, 4.04 mmol) dissolved in N,N,N',N'-tetramethylethylenediamine (16 ml), was dropwise added to the previous tetrahydrofuran solution (16 ml) of chloro-di-2-naphthyloxy-phosphine (2.70 g, 7.65 mmol) in a nitrogen atmosphere at −78° C. over a period of about 60 minutes with stirring. After the dropwise addition, the reaction solution was returned to 15° C. at a temperature raising rate of about 1.2° C./min. Then, the filtrate was subjected to vacuum distillation to obtain a residual liquid. This liquid was subjected to silica gel column chromatography (developer: toluene/hexane=about 1/9) to obtain a solution containing bisphosphite (12) only, and the solvent was distilled off under reduced pressure to obtain 0.57 g (yield: 12.3%) of a white solid powder.

EXAMPLE 13

1.30 g (yield: 10.2%) of bisphosphite (13) was obtained as a white solid powder in the same manner as in Example 1 except that 2-naphthol (10.60 g, 73.5 mmol) and 3,31,-di-t-butyl-5,5'-dimethoxy-2,2'-biphenyldiol (4.66 g, 13.0 mmol) were used instead of phenol (6.36 g, 67.6 mmol) and 3,3',5,5'-tetra-t-butyl-2,2'-biphenyldiol (6.94 g, 16.9 mmol), phosphorus trichloride was 5.10 g (37.1 mmol), pyridine was 5.80 g (73.3 mmol), n-butyl lithium dissolved in hexane was 15.4 ml (26.0 mmol), and the mixing ratio of the developer for the silica gel column chromatography was changed to chloroform/hexane=about

EXAMPLE 14

2.44 g (yield: 16.5%) of bisphosphite (14) was obtained as a white solid powder in the same manner as in Example 1 except that 1-naphthol (8.61 g, 59.8 mmol) and 3,3',-di-t-butyl-5,5'-dimethoxy-2,2'-biphenyldiol (5.35 g, 14.9 mmol) were used instead of phenol (6.36 g, 67.6 mmol) and 3,3',5,5'-tetra-t-butyl-2,2'-biphenyldiol (6.94 g, 16.9 mmol), phosphorus trichloride was 4.10 g (29.9 mmol), pyridine was 4.72 g (59.8 mmol), n-butyl lithium dissolved in hexane was 17.7 ml (29.9 mmol), and instead of purification by silica gel column chromatography (developer; toluene/hexane=about 1/5), washing with water, suspension washing with methanol, filtering off the solvent and then vacuum drying were carried out.

The bisphosphite compounds obtained in Examples 1 to 14 were confirmed to have the following structures (1) to (14) by $^{31}$P-NMR, $^{1}$H-NMR (Unity 300 Model, manufactured by Valian Company) and the elemental analysis. The analytical values are summarized in Tables 1 and 2.

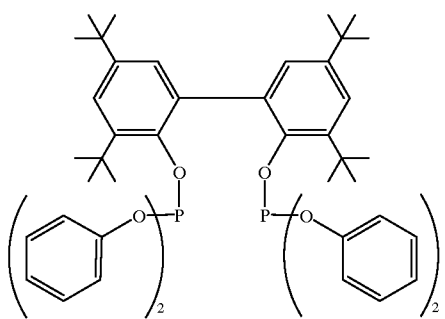
(1)
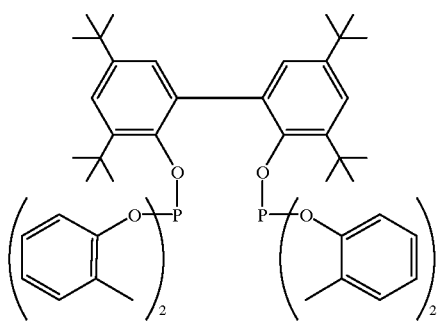
(2)
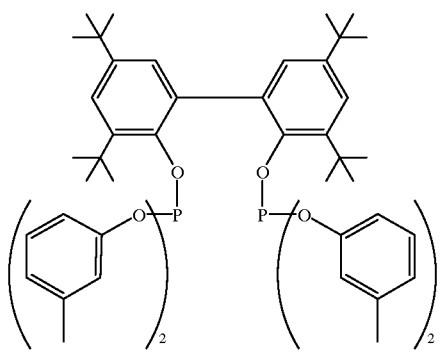
(3)
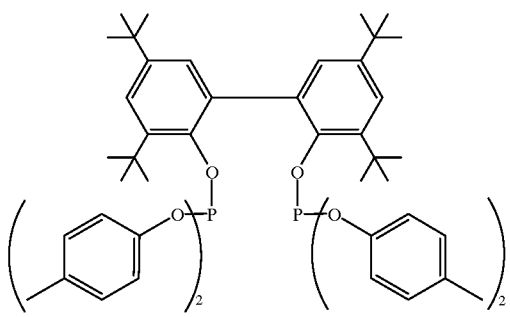
(4)

-continued
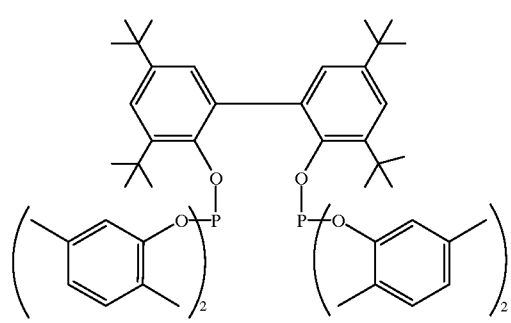
(5)
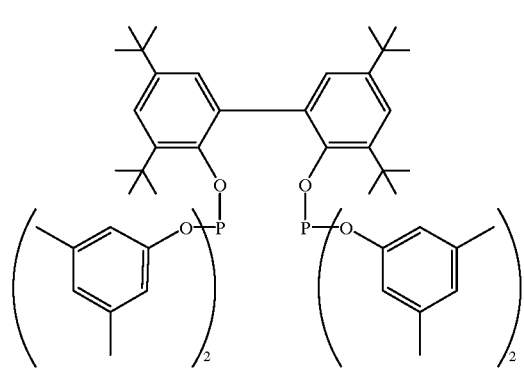
(6)
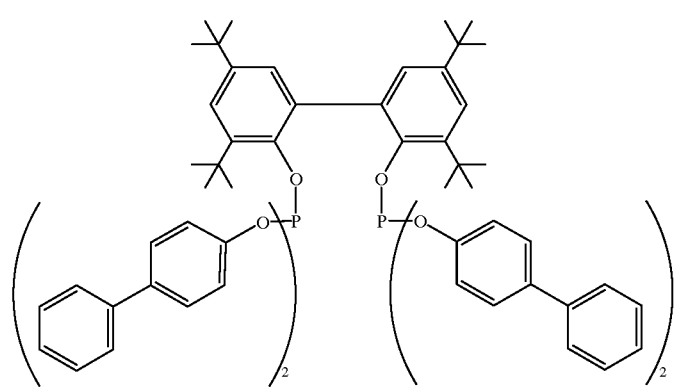
(7)
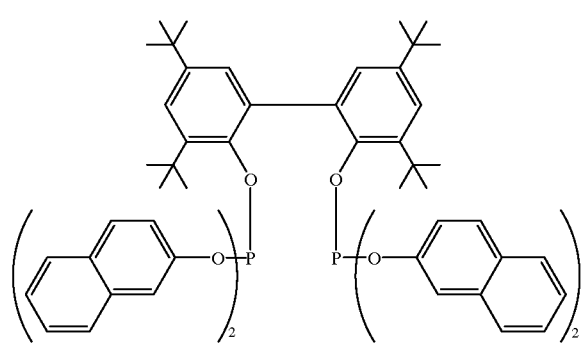
(8)

-continued
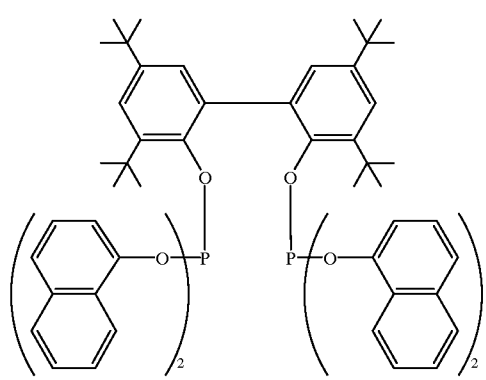
(9)
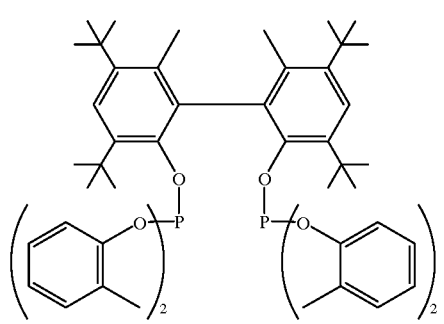
(10)
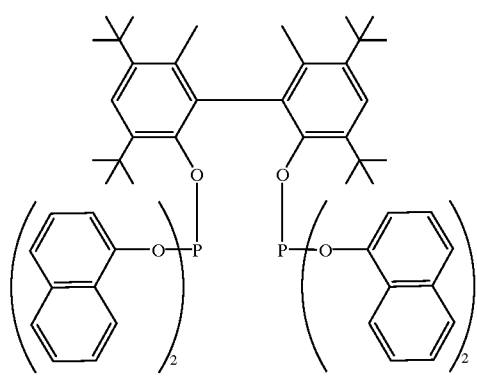
(11)
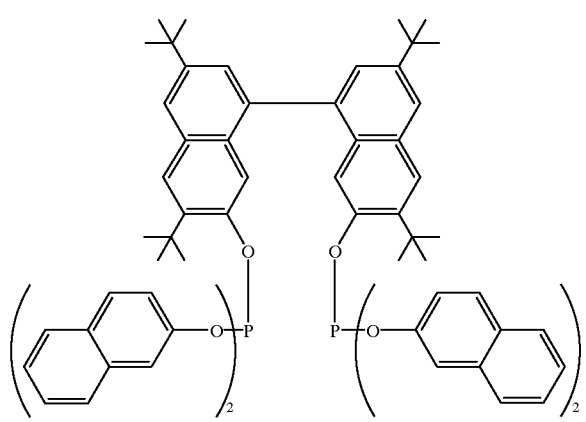
(12)

-continued

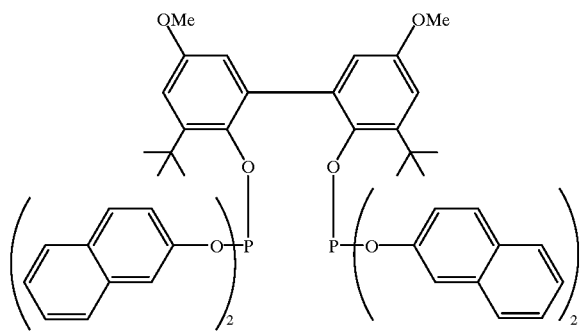
(13)

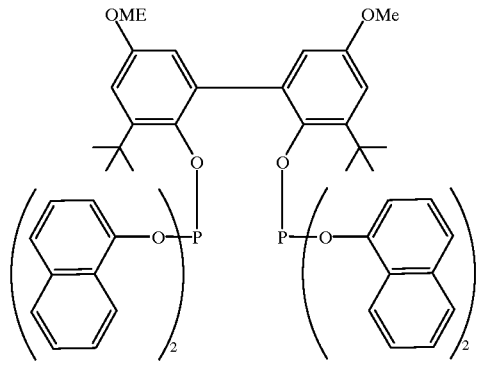
(14)

TABLE 1

| Bisphosphite | $^{31}$PNMR (ppm)[a] | $^{1}$HNMR (ppm) |
|---|---|---|
| (1) | 131.8 | 1.22 (18H, s), 1.61 (18H, s), 6.72~7.12 (20H, m), 7.49 (2H, d, J=2.6 Hz), 7.64 (2H, d, J=2.6 Hz) |
| (2) | 137.4 | 1.13 (18H, s), 1.67 (18H, s), 1.80 (6H, s), 2.20 (6H, s), 6.72~7.07 (16H, m), 7.44 (1H, s), 7.46 (1H, s), 7.56 (1H, s), 7.57 (1H, s) |
| (3) | 132.8 | 1.22 (18H, s), 1.67 (18H, s), 1.95 (6H, s), 2.01 (6H, s), 6.60~7.11 (16H, m), 7.49 (2H, d, J=2.6 Hz), 7.65 (2H, d, J=2.6 Hz) |
| (4) | 132.2 | 1.25 (18H, s), 1.67 (18H, s), 1.96 (6H, s), 1.99 (6H, s), 6.75~7.09 (16H, m), 7.53 (2H, d, J=2.4 Hz), 7.67 (2H, d, J=2.4 Hz) |
| (5) | 137.4 | 1.10 (18H, s), 1.72 (18H, s), 1.76 (6H, s), 1.90 (6H, s), 2.15 (6H, s), 2.23 (6H, s), 6.55~7.12 (12H, m), 7.36 (2H, d, J=2.6 Hz), 7.59 (2H, d, J=2.6 Hz) |
| (6) | 133.9 | 1.21 (18H, s), 1.73 (18H, s), 1.97 (12H, s), 2.03 (12H, s), 6.49 (4H, d, J=11.7 Hz), 6.57 (4H, s), 6.92 (4H, s), 7.49 (2H, d, J=2.5 Hz), 7.67 (2H, d, J=2.5 Hz) |
| (7) | 131.1 | 1.22 (18H, s), 1.66 (18H, s), 6.99~7.30 (36H, m), 7.55 (2H, d, J=2.4 Hz), 7.68 (2H, d, J=2.4 Hz) |
| (8) | 131.7 | 1.17 (18H, s), 1.67 (18H, s), 7.10~7.71 (32H, m) |
| (9) | 136.5 | 0.80 (18H, s), 1.72 (18H, s), 6.81~7.79 (30H, m), 8.53 (2H, m) |
| (10) | 130.3 | 1.29 (18H, s), 1.60 (18H, s), 1.88 (6H, s), 1.99 (6H, s) 2.28 (6H, s), 6.65~6.91 (14H, m) 7.06 (2H, d, J=10.1 Hz), 7.39 (2H, d, J=10.1 Hz), 7.71 (2H, s) |
| (11) | 131.1 | 1.20 (18H, s), 1.71 (18H, s), 2.23 (6H, s), 6.87~7.26 (18H, m), 7.43~7.48 (4H, m), 7.56 (2H, d, J=7.9 Hz), 7.80 (2H, s), 8.11 (2H, d, J=7.9 Hz), 8.21~8.25 (2H, m) |
| (12) | 127.2 | 1.21 (18H, s), 1.53 (18H, s), 6.49 (2H, dd, J=9.0, 2.4 Hz), 6.84~6.87 (2H, m), 7.09~7.48 (24H, m), 7.58~7.65 (6H, m), 7.86 (2H, s) |
| (13) | 134.2 | 1.40 (18H, s), 3.40 (6H, s), 6.60 (2H, s), 6.92 (2H, s), 7.00~7.78 (24H, m) |
| (14) | 136.8 | Not measured |

[a] Chemical shift based on phenyl phosphate.

TABLE 2

| Bisphosphite | Elemental analysis (%)[a] | | |
|---|---|---|---|
| | C | H | P[b] |
| (1) | 74.27 (74.09) | 7.15 (7.17) | 7.46 (7.35) |
| (2) | 75.27 (74.31) | 7.83 (7.62) | 6.47 (6.89) |
| (3) | 75.02 (74.81) | 7.68 (7.62) | 6.68 (6.89) |
| (4) | 74.23 (74.81) | 7.28 (7.62) | 7.00 (6.89) |
| (5) | 75.71 (75.45) | 8.18 (8.02) | 6.18 (6.49) |
| (6) | 74.58 (75.45) | 8.10 (8.02) | 6.35 (6.49) |
| (7) | 79.65 (79.56) | 6.64 (6.68) | 5.06 (5.40) |
| (8) | 78.34 (78.29) | 6.53 (6.57) | 5.94 (5.94) |
| (9) | 78.46 (78.29) | 6.73 (6.57) | 5.80 (5.94) |
| (10) | 75.28 (75.14) | 7.83 (7.83) | 6.45 (6.68) |
| (11) | 78.73 (78.48) | 6.74 (6.77) | 5.58 (5.78) |
| (12) | 80.17 (79.84) | 6.32 (6.35) | 5.04 (5.42) |
| (13) | 75.05 (75.14) | 5.76 (5.70) | 6.19 (6.25) |
| (14) | —[c] | —[c] | —[c] |

[a] Calculated values are in brackets ( ).
[b] XRF measurement
[c] Not measured

Comparative Example 1

A tetrahydrofuran (39 ml) solution of 3,3',6,6'-tetra-t-butyl-1,1'-binaphthyl-2,2'-diol (2.90 g, 5.67 mmol) and pyridine (9.01 g, 113.4 mmol), was dropwise added to a tetrahydrofuran (19 ml) solution of chloro-di-2-naphthyloxyphosphine purified in Example 12 (4.03 g, 11.4 mmol), at 0° C. over a period of about 20 minutes with stirring. After the dropwise addition, the mixture was stirred at room temperature for 2 hours. By product solid LiCl was filtered off, and the filtrate was subjected to vacuum distillation to obtain a residual liquid. However, this residual liquid did not contain bisphosphite (12) at all, and instead, the following compounds (C) (yield: 21%), (D) (yield: 22%) and (E) (yield: 57%) were obtained.

Compound (C)

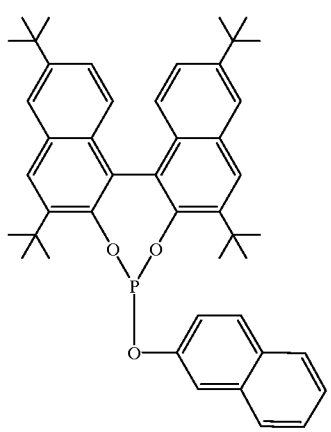

Compound (D)

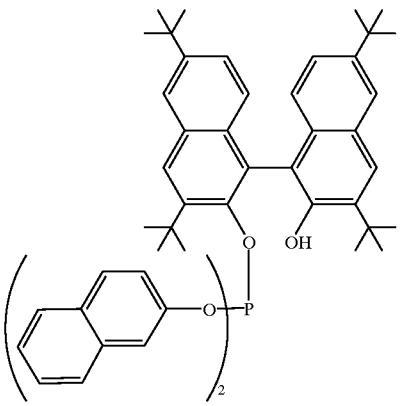

Compound (E)

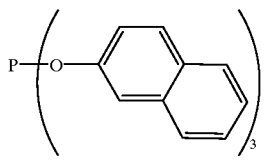

Hydroformylation Reaction

EXAMPLE 15

Into a top and bottom stirring type stainless steel autoclave having an internal capacity of 200 ml, 55 ml of toluene as a solvent, 5 ml of n-heptane as an internal standard, 39.4 mg of $[Rh(OAc)(COD)]_2$ and 491.6 mg of bisphosphite (1) (molar ratio of P/Rh=8.0) were charged under a nitrogen atmosphere, and then the autoclave was sealed. The interior of the autoclave was flushed three times with 10 kg/cm²G of nitrogen gas, and then the pressure was reduced to 0 kg/cm²G of nitrogen gas. Then, 4.5 g of propylene was injected thereto. The temperature was raised to 70° C., and synthesis gas ($H_2/CO=1$) was immediately injected so that the total pressure in the autoclave became 9 kg/cm²G inclusive of the pressure of propylene itself to initiate the reaction. The reaction was continued for 80 minutes while synthesis gas consumed during the reaction was supplemented by a pressure accumulator via a secondary pressure controller to always maintain the total pressure in the reactor at a level of 9 kg/cm²G. After completion of the reaction, the reactor was cooled to room temperature, and the gas phase and the liquid phase in the autoclave were collected and subjected to the analyses of the respective components by means of gas chromatography. The reaction rate constant (k) was 3.0/hr. The yield of $C_4$ aldehydes was 95.8%, and the ratio (n/i) of desired n-butyraldehyde to i-butyraldehyde was 43.5.

EXAMPLE 16

The hydroformylation reaction of propylene was carried out in the same manner as in Example 15 except that instead of 491.6 mg of bisphosphite (1), 524.4 mg of bisphosphite (2) (molar ratio of P/Rh: 8.0) was charged under a nitrogen atmosphere, and the reaction time was changed to 90 minutes. The reaction rate constant (k) was 2.6/hr. The yield of $C_4$ aldehydes was 96.0%, and the ratio (n/i) of desired n-butyraldehyde to i-butyraldehyde was 96.7.

EXAMPLE 17

The hydroformylation reaction of propylene was carried out in the same manner as in Example 15 except that instead of 491.6 mg of bisphosphite (1), 557.1 mg of bisphosphite (3) (molar ratio of P/Rh: 8.2) was charged under a nitrogen atmosphere, and the reaction time was changed to 75 minutes. The reaction rate constant (k) was 2.4/hr. The yield of $C_4$ aldehydes was 95.1%, and the ratio (n/i) of desired n-butyraldehyde to i-butyraldehyde was 39.3.

EXAMPLE 18

The hydroformylation reaction of propylene was carried out in the same manner as in Example 15 except that instead of 491.6 mg of bisphosphite (1), 527.5 mg of bisphosphite (4) (molar ratio of P/Rh: 8.0) was charged under a nitrogen atmosphere, and the reaction time was changed to 85 minutes. The reaction rate constant (k) was 2.3/hr. The yield of $C_4$ aldehydes was 93.9%, and the ratio (n/i) of desired n-butyraldehyde to i-butyraldehyde was 39.4.

EXAMPLE 19

The hydroformylation reaction of propylene was carried out in the same manner as in Example 15 except that instead of 491.6 mg of bisphosphite (1), 557.1 mg of bisphosphite (5) (molar ratio of P/Rh: 8.0) was charged under a nitrogen atmosphere, and the reaction time was changed to 120 minutes. The reaction rate constant (k) was 2.0/hr. The yield of $C_4$ aldehydes was 96.0%, and the ratio (n/i) of desired n-butyraldehyde to i-butyraldehyde was 147.3.

EXAMPLE 20

The hydroformylation reaction of propylene was carried out in the same manner as in Example 15 except that instead of 491.6 mg of bisphosphite (1), 557.1 mg of bisphosphite (6) (molar ratio of P/Rh: 8.0) was charged under a nitrogen atmosphere, and the reaction time was changed to 80 minutes. The reaction rate constant (k) was 2.6/hr. The yield of $C_4$ aldehydes was 94.9%, and the ratio (n/i) of desired n-butyraldehyde to i-butyraldehyde was 32.9.

EXAMPLE 21

The hydroformylation reaction of propylene was carried out in the same manner as in Example 15 except that instead of 491.6 mg of bisphosphite (1), 669.2 mg of bisphosphite (7) (molar ratio of P/Rh: 8.0) was charged under a nitrogen atmosphere, and the reaction time was changed to 65 minutes. The reaction rate constant (k) was 3.2/hr. The yield of $C_4$ aldehydes was 95.0%, and the ratio (n/i) of desired n-butyraldehyde to i-butyraldehyde was 44.6.

EXAMPLE 22

The hydroformylation reaction of propylene was carried out in the same manner as in Example 15 except that instead of 491.6 mg of bisphosphite (1), 608.4 mg of bisphosphite (8) (molar ratio of P/Rh: 8.0) was charged under a nitrogen atmosphere, and the reaction time was changed to 60 minutes. The reaction rate constant (k) was 4.1/hr. The yield of $C_4$ aldehydes was 95.4%, and the ratio (n/i) of desired n-butyraldehyde to i-butyraldehyde was 44.0.

EXAMPLE 23

The hydroformylation reaction of propylene was carried out in the same manner as in Example 15 except that instead of 491.6 mg of bisphosphite (1), 608.4 mg of bisphosphite (9) (molar ratio of P/Rh: 8.0) was charged under a nitrogen atmosphere, and the reaction time was changed to 70 minutes. The reaction rate constant (k) was 3.8/hr. The yield of $C_4$ aldehydes was 96.5%, and the ratio (n/i) of desired n-butyraldehyde to i-butyraldehyde was 113.7.

EXAMPLE 24

The hydroformylation reaction of propylene was carried out in the same manner as in Example 15 except that instead of 491.6 mg of bisphosphite (1), 540.7 mg of bisphosphite (10) (molar ratio of P/Rh: 8.0) was charged under a nitrogen atmosphere, and the reaction time was changed to 75 minutes. The reaction rate constant (k) was 3.2/hr. The yield of $C_4$ aldehydes was 93.2%, and the ratio (n/i) of desired n-butyraldehyde to i-butyraldehyde was 35.5.

EXAMPLE 25

The hydroformylation reaction of propylene was carried out in the same manner as in Example 15 except that instead of 491.6 mg of bisphosphite (1), 624.8 mg of bisphosphite (11) (molar ratio of P/Rh: 8.0) was charged under a nitrogen atmosphere, and the reaction time was changed to 60 minutes. The reaction rate constant (k) was 4.0/hr. The yield of $C_4$ aldehydes was 94.3%, and the ratio (n/i) of desired n-butyraldehyde to i-butyraldehyde was 66.8.

EXAMPLE 26

The hydroformylation reaction of propylene was carried out in the same manner as in Example 15 except that instead of 491.6 mg of bisphosphite (1), 333.4 mg of bisphosphite (12) and 19.7 mg of $[Rh(OAc)(COD)]_2$ (molar ratio of P/Rh: 8.0) were charged under a nitrogen atmosphere, and the reaction time was changed to 78 minutes. The reaction rate constant (k) was 2.7/hr. The yield of $C_4$ aldehydes was 96.0%, and the ratio (n/i) of desired n-butyraldehyde to i-butyraldehyde was 21.7.

EXAMPLE 27

The hydroformylation reaction of propylene was carried out in the same manner as in Example 15 except that instead of 491.6 mg of bisphosphite (1), 578.0 mg of bisphosphite (13) (molar ratio of P/Rh: 8.0) was charged under a nitrogen atmosphere, and the reaction time was changed to 75 minutes. The reaction rate constant (k) was 2.5/hr. The yield of $C_4$ aldehydes was 92.8%, and the ratio (n/i) of desired n-butyraldehyde to i-butyraldehyde was 72.0.

EXAMPLE 28

The hydroformylation reaction of propylene was carried out in the same manner as in Example 15 except that instead of 491.6 mg of bisphosphite (1), 578.0 mg of bisphosphite (14) (molar ratio of P/Rh: 8.0) was charged under a nitrogen atmosphere, and the reaction time was changed to 60 minutes. The reaction rate constant (k) was 2.7/hr. The yield of $C_4$ aldehydes was 93.8%, and the ratio (n/i) of desired n-butyraldehyde to i-butyraldehyde was 160.5.

Comparative Example 2

The hydroformylation reaction of propylene was carried out in the same manner as in Example 15 except that instead of 491.6 mg of bisphosphite (1), 393.5 mg of bisphosphite (F) having the following formula (molar ratio of P/Rh: 8.0) was charged under a nitrogen atmosphere, and the reaction time was changed to 115 minutes. The reaction rate constant (k) was 1.8/hr. The yield of $C_4$ aldehydes was 95.0%, and the ratio (n/i) of desired n-butyraldehyde to i-butyraldehyde was 9.8.

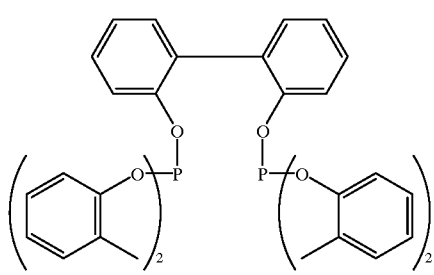

(F)

The results of the reactions in Examples 15 to 28 and Comparative Example 2 are summarized in Table 3.

TABLE 3

| | Bisphosphite | Reaction temp. (°C.) | Reaction rate constant/ (hr) | C₄-aldehydes (yield: %) | C₄-aldehydes (n/i ratio) |
|---|---|---|---|---|---|
| Example 15 | (1) | 70 | 3.0 | 95.8 | 43.5 |
| Example 16 | (2) | 70 | 2.6 | 96.0 | 96.7 |
| Example 17 | (3) | 70 | 2.4 | 95.1 | 39.3 |
| Example 18 | (4) | 70 | 2.3 | 93.9 | 39.4 |
| Example 19 | (5) | 70 | 2.0 | 96.0 | 147.3 |
| Example 20 | (6) | 70 | 2.6 | 94.9 | 32.9 |
| Example 21 | (7) | 70 | 3.2 | 95.0 | 44.6 |
| Example 22 | (8) | 70 | 4.1 | 95.4 | 44.0 |
| Example 23 | (9) | 70 | 3.8 | 96.5 | 113.7 |
| Example 24 | (10) | 70 | 3.2 | 93.2 | 35.5 |
| Example 25 | (11) | 70 | 4.0 | 94.3 | 66.8 |
| Example 26 | (12) | 70 | 2.7* | 96.0 | 21.7 |
| Example 27 | (13) | 70 | 2.5 | 92.8 | 72.0 |
| Example 28 | (14) | 70 | 2.7 | 93.8 | 160.5 |
| Comparative Example 2 | (Comp. 1) | 70 | 1.8 | 95.0 | 9.8 |

*The Rh concentration was one half of the concentration in other Examples.

EXAMPLE 29

A tetrahydrofuran (about 130 ml) solution of 6-hydroxyquinoline (4.50 g, 30.38 mmol) and triethylamine (7.685 g, 75.95 mmol) was dropwise added to a tetrahydrofuran (about 100 ml) solution of phosphorus trichloride (2.086 g, 15.19 mmol) in a nitrogen atmosphere at 0° C. over a period of about 1.5 hours with stirring. Then, by-product solid triethylamine hydrochloride was filtered off, and then solvent was distilled off to obtain a yellow oil. To this residue, toluene (20 ml) was added to obtain a toluene solution containing $ClP(OC_9H_6N)_2$. On the other hand, n-butyl lithium dissolve in hexane (5.99 ml, 10.52 mmol) was dropwise added to a tetrahydrofuran (about 50 ml) solution of 3,3',5,5'-tetra-t-butyl-2,2'-biphenyldiol (2.078 g, 5.06 mmol) in a nitrogen atmosphere at 0° C., followed by boiling and refluxing for about 1 hour to obtain a dilithium salt of 3,3',5,5'-tetra-t-butyl-2,2'-biphenyldiol. Then, the dilithium salt of 3,3',5,5'-tetra-t-butyl-2,2'-biphenyldiol dissolved in tetrahydrofuran, was dropwise added to the previously obtained toluene solution containing $ClP(OC_9H_6N)_2$ in a nitrogen atmosphere at −70° C. over a period of about 90 minutes with stirring. After the dropwise addition, the reaction solution was returned to 0° C. at a temperature raising rate of about 1.2° C./min. Then, about one half of the reaction solution was concentrated under reduced pressure, and the residue was extracted and washed with toluene/water system. The toluene layer was dried over anhydrous magnesium sulfate, and then the solvent was distilled off to obtain about 6 g of an oil. Acetonitrile was added thereto to obtain a uniform solution, which was left to stand overnight at −20° C., whereby the desired bisphosphite (158) was obtained in an amount of 1.25 g (yield: 23.6%) as a substantially white solid powder.

$^{31}$P-NMR (CDCl₃)δ130.9 (based on phenyl phosphate)

$^1$H-NMR (CDCl₃, TMS)δ1.2(18H,s), 1.42(18H,s), 7.1–7.3(14H,m), 7.5(2H,m), 7.66(2H,m), 7.8–7.95(6H,m), 8.75(2H,m), 8.80(2H,m)

EXAMPLE 30

A tetrahydrofuran (about 130 ml) solution of 6-hydroxyquinoline (4.676 g, 32.21 mmol) and triethylamine (8.40 g, 83.0 mmol) was dropwise added to a tetrahydrofuran (about 100 ml) solution of phosphorus trichloride (2.457 g, 17.89 mmol) in a nitrogen atmosphere at 0° C. over a period of about 1.5 hours with stirring. Then, the mixture was stirred in an oil bath of 85° C. for 20 hours. Then, by-product solid triethylamine hydrochloride was filtered off, and then the obtained solution containing ClP $(OC_9H_6N)_2$ was concentrated to about 80 ml. On the other hand, n-butyl lithium dissolved in hexane (10.6 ml, 16.5 mmol) was dropwise added to a tetrahydrofuran (about 30 ml) solution of 3,3',5,5'-tetra-t-butyl-6,6'-dimethyl-2,2'-biphenyldiol (3.532 g, 8.05 mmol) in a nitrogen atmosphere at 0° C., followed by boiling and refluxing for about 1 hour to obtain a dilithium salt of 3,3',5,5'-tetra-t-butyl-6,6'-dimethyl-2,2'-biphenyldiol. Then, the dilithium salt of 3,3', 5,5'-tetra-t-butyl-6,6'-dimethyl-2,2'-biphenyldiol dissolved in tetrahydrofuran, was dropwise added to the previously obtained tetrahydrofuran solution containing ClP $(OC_9H_6N)_2$ in a nitrogen atmosphere at −70° C. over a period of about 15 minutes with stirring. After the dropwise addition, the reaction solution was returned to room temperature at a temperature raising rate of about 0.6° C./min. Then, the solvent of the reaction solution was distilled off under reduced pressure, and the residue was extracted and washed with toluene/water system. The toluene layer was dried over anhydrous sodium sulfate, and then the solvent was distilled off to obtain a brown oil. Acetonitrile was added thereto, and the formed white precipitate was filtered off. Then, the solvent of the filtrate was distilled off under reduced pressure. The residue was dissolved in a small amount of chloroform, and hexane was added thereto. The mixture was cooled to −30° C. with stirring, and the supernatant was removed. The obtained rubbery substance was dissolved in a small amount of acetonitrile, and unnecessary substances were filtered off. The filtrate was evaporated to dryness under reduced pressure to obtain the desired bisphosphite (177) in an amount of 0.676 g (yield: 7.8%) as a yellow white solid powder.

$^{31}$P-NMR (CDCl₃)δ125.75 (based on phenyl phosphate)

$^1$H-NMR (CDCl₃, TMS)δ1.31(18H,s), 1.46(18H,s), 2.13 (6H,s) 7.06(2H,s), 7.08–7.14(14H,m), 7.16–7.20(4H,m) 7.28–7.32(2H,m), 7.54(2H,d,J=3.8Hz), 7.60(2H,s), 7.68 (2H,d,J=3.8Hz). 7.84–7.91(4H,m), 8.67(2H,dd,J=1.7, 0.7Hz), 8.79(2H,dd,J=1.7,0.7Hz)

The bisphosphite compounds obtained in Example 29 and 30 were confirmed to have the following structures (158) and (177) by $^{31}$P-NMR, $^1$H-NMR (Unity 300 Model, manufactured by Valian Company).

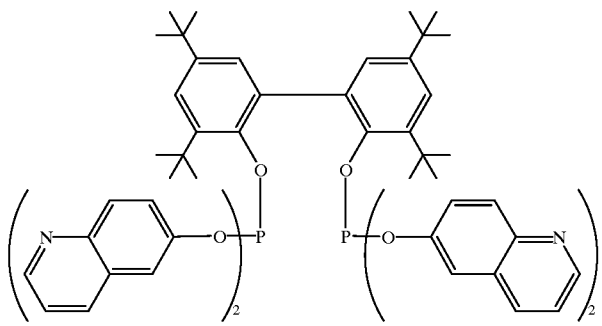

(158)

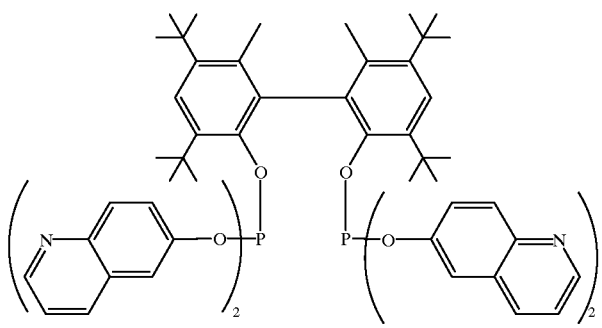

(177)

Hydroformylation Reaction

EXAMPLE 31

Into a top and bottom stirring type stainless steel autoclave having an internal capacity of 200 ml, 55 ml of toluene as a solvent, 5 ml of n-heptane as an internal standard, 19.8 mg of $[Rh(OAc)(COD)]_2$ and 307.0 mg of bisphosphite (158) (molar ratio of P/Rh=8.0) were charged under a nitrogen atmosphere, and then the autoclave was sealed. The interior of the autoclave was flushed three times with 10 kg/cm$^2$G of nitrogen gas, and then the pressure was reduced to 0 kg/cm$^2$G of nitrogen gas. Then, 4.5 g of propylene was injected thereto. The temperature was raised to 70° C., and synthesis gas (H$_2$/CO=1) was immediately injected so that the total pressure in the autoclave became 9 kg/cm$^2$G inclusive of the pressure of propylene itself to initiate the reaction. The reaction was continued for 60 minutes while synthesis gas consumed during the reaction was supplemented by a pressure accumulator via a secondary pressure controller to always maintain the total pressure in the reactor at a level of 9 kg/cm$^2$G. After completion of the reaction, the reactor was cooled to room temperature, and the gas phase and the liquid phase in the autoclave were collected and subjected to the analyses of the respective components by means of gas chromatography. The reaction rate constant (k) was 3.21/hr. The yield of C$_4$ aldehydes was 96.5% and the ratio (n/i) of desired n-butyraldehyde to i-butyraldehyde was 49.0.

EXAMPLE 32

The hydroformylation reaction of propylene was carried out in the same manner as in Example 31 except that instead of 307.0 mg of bisphosphite (158), 313.8 mg of bisphosphite (177) (molar ratio of P/Rh: 8.0) was charged under a nitrogen atmosphere, and the reaction time was changed to 45 minutes. The reaction rate constant (k) was 3.12/hr. The yield of C$_4$ aldehydes was 90.3%, and the ratio (n/i) of desired n-butyraldehyde to i-butyraldehyde was 15.0.

Preparation of Bisphosphite Compound

EXAMPLE 33

2.3 g (yield: 33.7%) of bisphosphite (254) was obtained as a white solid powder in the same manner as in Example 1 except that 1-methyl-2-naphthol (3.81 g, 24.1 mmol) and 3,3',5,5'-tetra-t-butyl-6,6'-dimethyl-2,2'-biphenyldiol (2.64 g, 6.0 mmol) were used instead of phenol (6.36 g, 67.6 mmol) and 3,3',5,5'-tetra-t-butyl-2,2'-biphenyldiol (6.94 g, 16.9 mmol), phosphorus trichloride was 1.74 g (12.7 mmol), pyridine was 2.18 g (27.6 mmol), and n-butyl lithium dissolved in hexane was 7.9 ml (12.3 mmol).

$^{31}$P-NMR δ130.1 (based on phenyl phosphate)

$^1$H-NMR δ1.25(18H,s), 1.43(18H,s), 2.10(6H,s), 2.11 (6H,s), 2.15(6H,s), 7.15(2H,d,J=8.7Hz), 7.21(2H,d,J= 9.0Hz), 7.27–7.31(4H,m), 7.33–7.41(4H,m), 7.45(2H,d,J= 9.0Hz), 7.55–7.57(4H,m), 7.68–7.74(8H,m)

The bisphosphite compound obtained in Example 33 was confirmed to have the following structure (254) by $^{31}$P-NMR, $^1$H-NMR (Unity 300 Model: manufactured by Valian Company).

(254)

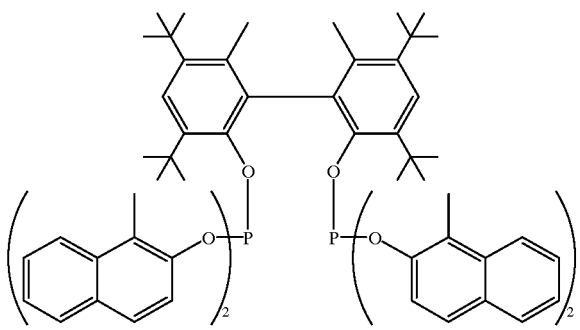

Hydroformylation Reaction

EXAMPLE 34

The hydroformylation reaction of propylene was carried out in the same manner as in Example 15 except that instead of 491.6 mg of bisphosphite (1), 658.2 mg of bisphosphite (254) (molar ratio of P/Rh: 8.0) was charged under a nitrogen atmosphere, and the reaction time was changed to 75 minutes. The reaction rate constant (k) was 2.2/hr. The yield of $C_4$ aldehydes was 92.1%, and the ratio (n/i) of desired n-butyraldehyde to i-butyraldehyde was 53.1.

EXAMPLE 35

The hydroformylation of propylene was carried out in the same manner as in Example 22 except that the reaction temperature was changed to 80° C. The reaction rate constant (k) was 7.3/hr, and the ratio (n/i) of desired n-butyraldehyde to i-butyraldehyde was 40.7.

EXAMPLE 36

The hydroformylation of propylene was carried out in the same manner as in Example 22 except that the molar ratio of P/Rh was changed to 4. The reaction rate constant (k) was 5.4/hr, and the ratio (n/i) of desired n-butyraldehyde to i-butyraldehyde was 44.2.

EXAMPLE 37

The hydroformylation of propylene was carried out in the same manner as in Example 22 except that the molar ratio of P/Rh was changed to 20. The reaction rate constant (k) was 5.6/hr, and the ratio (n/i) of desired n-butyraldehyde to i-butyraldehyde was 42.5.

EXAMPLE 38

The hydroformylation of propylene was carried out in the same manner as in Example 25 except that the molar ratio of P/Rh was changed to 4. The reaction rate constant (k) was 4.0/hr, and the ratio (n/i) of desired n-butyraldehyde to i-butyraldehyde was 76.3.

EXAMPLE 39

The hydroformylation of propylene was carried out in the same manner as in Example 25 except that the molar ratio of P/Rh was changed to 20. The reaction rate constant (k) was 4.0/hr, and the ratio (n/i) of desired n-butyraldehyde to i-butyraldehyde was 77.1.

The bisphosphite compound of the present invention is a novel compound which can be used as a constituting element of a homogeneous metal catalyst for various organic reactions such as hydrogenation, hydroformylation, hydrocyanation, hydrocarboxylation, hydroamidation, hydroesterification and aldol condensation.

Further, by the process of the present invention, it has been made possible to produce industrially advantageously in a simple operation a bisphosphite compound which could not be produced in good yield by conventional methods.

By using the bisphosphite compound having the specific structure as a catalyst component in the hydroformylation process of the present invention, it is possible to attain not only a high catalytic activity but also extremely high selectivity for aldehyde isomers, whereby the hydroformylation reaction can be carried out industrially and advantageously.

what is claimed is:

1. A bisphosphite compound of the following formula (A):

(A)

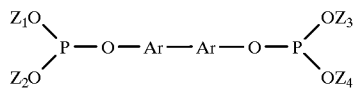

wherein —Ar—Ar— is a bisarylene group represented by any of the following formulae (A-I) to (A-III), and each of $Z_1$ to $Z_4$ is a $C_{4-20}$ aromatic or heteroaromatic group which may have a substituent, wherein each of substituents on carbon atoms of an aromatic ring adjacent to the carbon atom bonded to the oxygen atom in each of $Z_1$ to $Z_4$, is a group selected from the group consisting of hydrogen, methoxy, methyl, ethyl, trifluoromethyl, cyano, nitro and halogen, and each pair of $Z_1$ and $Z_2$, and $Z_3$ and $Z_4$, are not bonded to each other, (A-I)

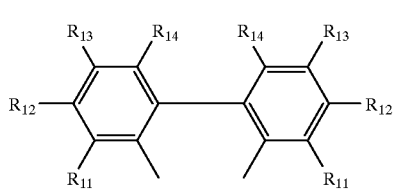

wherein each $R_{11}$ which is independent of the other $R_{11}$, is a $C_{4-20}$ alkyl or cycloalkyl group, and each of $R_{12}$ to $R_{14}$ which are independent of one another, is a hydrogen atom, a $C_{1-20}$ alkyl, alkoxy, cycloalkyl, cycloalkoxy, dialkylamino, aryl, aryloxy, alkylaryl, alkylaryloxy, arylalkyl or arylalkoxy group, a cyano group, a hydroxyl group or a halogen atom, (A-II)

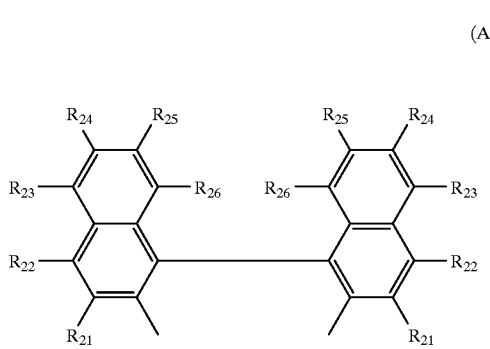

wherein each $R_{21}$ which is independent of the other $R_{21}$, is the same as $R_{11}$ in the formula (A-I), and each of $R_{22}$ to $R_{26}$ which are independent of one another, is the same as $R_{12}$ to $R_{14}$ in the formula (A-I), (A-III)

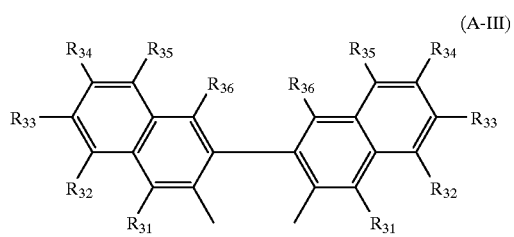

wherein each $R_{31}$ which is independent of the other $R_{31}$, is the same as $R_{11}$ in the formula (A-I), and each of $R_{32}$ to $R_{36}$ which are independent of one another, is the same as $R_{12}$ to $R_{14}$ in the formula (A-I).

2. The bisphosphite compound according to claim 1, which is represented by the following formula (I):

(I)

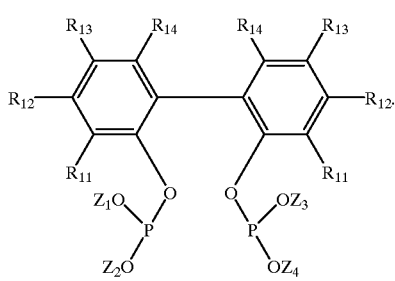

3. The bisphosphite compound according to claim 1, which is represented by the following formula (II):

(II)

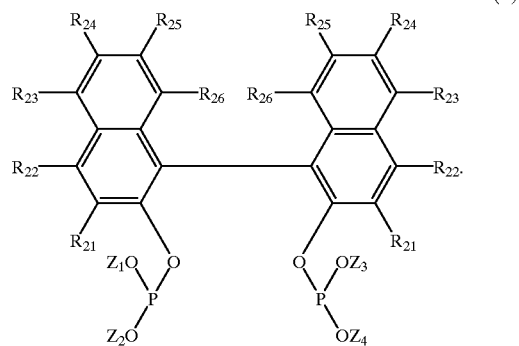

4. The bisphosphite compound according to claim 1, which is represented by the following formula (III):

(III)

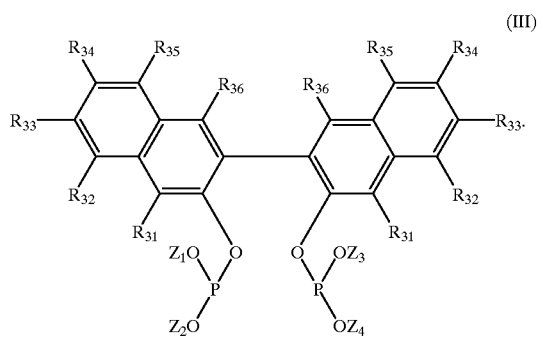

5. The bisphosphite compound according to claim 2, wherein in the formula (I), each $R_{11}$ is a $C_{4-20}$ tertiary alkyl group.

6. The bisphosphite compound according to claim 3, wherein in the formula (II), each $R_{21}$ is a $C_{4-20}$ tertiary alkyl group.

7. The bisphosphite compound according to claim 4, wherein in the formula (III), each $R_{31}$ is a $C_{4-20}$ tertiary alkyl group.

8. A process for producing a bisphosphite compound of the following formula (A):

(A)

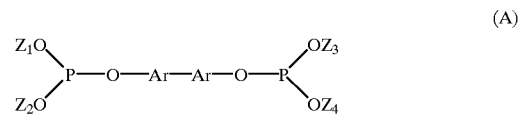

wherein —Ar—Ar— is a bisarylene group presented by any one of the following formulae (A-I) to (A-III), and each of $Z_1$ to $Z_4$ is a $C_{4-20}$ aromatic or heteroaromatic group which may have a substitutent, wherein each of substituents on carbon atoms of an aromatic ring adjacent to the carbon atom bonded to the oxygen atom in each of $Z_1$ to $Z_4$, is a group selected from the group consisting of hydrogen, methoxy, methyl, ethyl, trifluoromethyl, cyano, nitro and halogen, and each pair of $Z_1$ and $Z_2$, and $Z_3$ and $Z_4$, are not bonded to each other, (A-I)

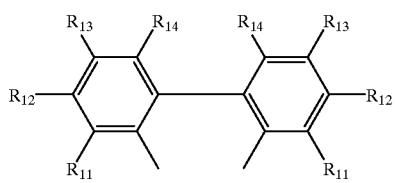

wherein $R_{11}$ which is independent of the other $R_{11}$ is a $C_{3-20}$ alkyl or cycloalkyl group, and each of $R_{12}$ to $R_{14}$ which are independent of one another is a hydrogen atom, a $C_{1-20}$ alkyl, alkoxy, cycloalkyl, cycloalkoxy, dialkylamino, aryl, aryloxy, alkylaryl, alkylaryloxy, arylalkyl or arylalkoxy group, a cyano group, a hydroxyl group or a halogen atom, (A-II)

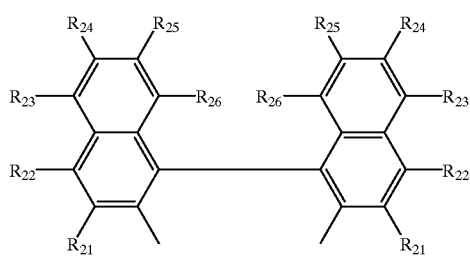

wherein each $R_{21}$ which is independent of the other $R_{21}$, is the same as $R_{11}$ in the formula (A-I), and each of $R_{22}$ to $R_{26}$ which are independent of one another, is the same as $R_{12}$ to $R_{14}$ in the formula (A-I), (A-III)

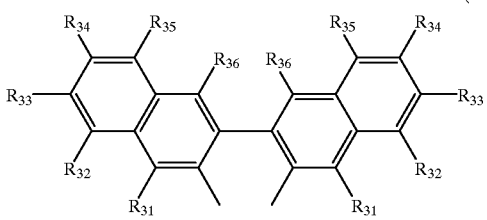

wherein each $R_{31}$ which is independent of the other $R_{31}$, is the same as $R_{11}$ in the formula (A-I), and each of $R_{32}$ to $R_{36}$ which are independent of one another, is the same as $R_{12}$ to $R_{14}$ in the formula (A-I), which comprises a step of contacting a compound of the following formula (B):

wherein —Ar—Ar— is as defined above in the formula (A), and M is an alkali metal or an alkaline earth metal, with a phosphorus compound of the following formula (B-I) and/or (B-II):

(B-I)

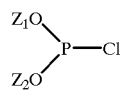

(B-II)

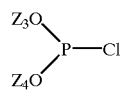

wherein $Z_1$ to $Z_4$ are as defined above in the formula (A), at a temperature of at most 20° C. for at least one minute.

9. A hydroformylation process for producing aldehydes, which comprises reacting an olefinic compound with carbon monoxide and hydrogen in the presence of a compound of an element selected from Groups 8 to 10 of the Periodic Table (hereinafter referred to as a "Group VIII metal"), wherein the reaction is carried out in the presence of a bisphosphite compound of the following formula (A):

(A)

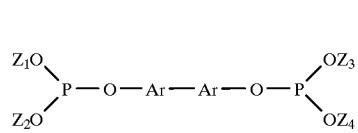

wherein —Ar—Ar— is a bisarylene group represented by any one of the following formulae (A-I) to (A-III), and each of $Z_1$ to $Z_4$ is a $C_{4-20}$ aromatic or heteroaromatic group which may have a substituent, wherein each of substituents on carbon atoms of an aromatic ring adjacent to the carbon atom bonded to the oxygen atom in each of $Z_1$ to $Z_4$, is a group selected from the group consisting of hydrogen, methoxy methyl, ethyl, trifluoromethyl, cyano, nitro and halogen, and each pair of $Z_1$ and $Z_2$, and $Z_3$ and $Z_4$, are not bonded to each other, (A-I)

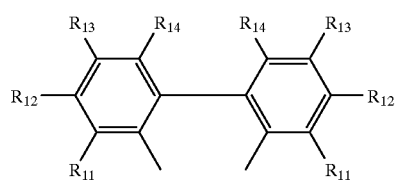

wherein $R_{11}$ which is independent of the other $R_{11}$, is a $C_{3-20}$ alkyl or cycloalkyl group, and each of $R_{12}$ to $R_{14}$ which are independent of one another, is a hydrogen atom, a $C_{1-20}$ alkyl, alkoxy, cycloalkyl, cycloalkoxy, dialkylamino, aryl, aryloxy, alkylaryl, alkylaryloxy, arylalkyl or arylalkoxy group, a cyano group, a hydroxyl group or a halogen atom,

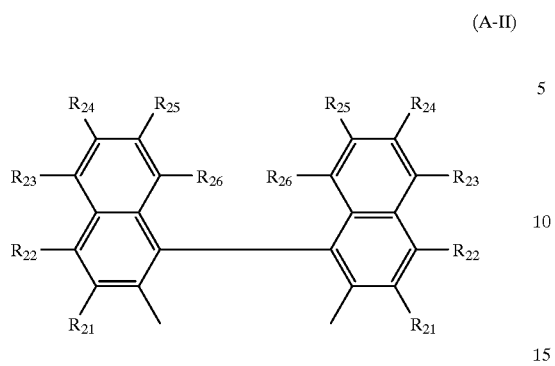
(A-II)

wherein each $R_{21}$ which is independent of the other $R_{21}$, is the same as $R_{11}$ in the formula (A-I), and each of $R_{22}$ to $R_{26}$ which are independent of one another, is the same as $R_{12}$ to $R_{14}$ in the formula (A-I),

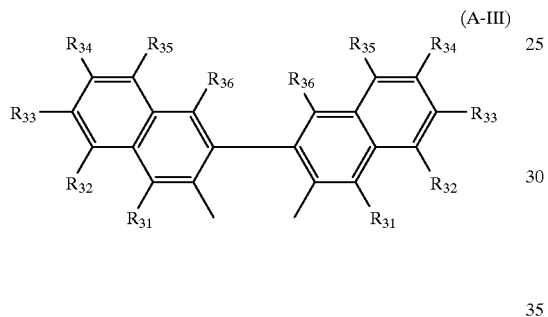
(A-III)

wherein each $R_{31}$ which is independent of the other $R_{31}$, is the same as $R_{11}$ in the formula (A-I), and each of $R_{32}$ to $R_{36}$ which are independent of one another, is the same as $R_{12}$ to $R_{14}$ in the formula (A-I).

10. The hydroformylation process according to claim 9, wherein the reaction is carried out in the presence of a bisphosphite compound of the following formula (I):

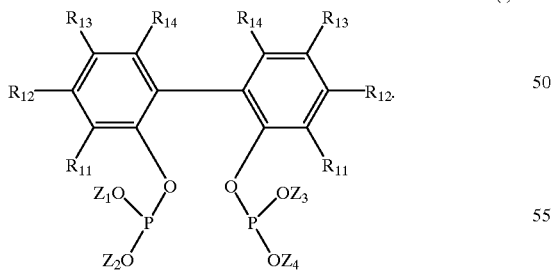
(I)

11. The hydroformylation process according to claim 9, wherein the reaction is carried out in the presence of a bisphosphite compound of the following formula (II):

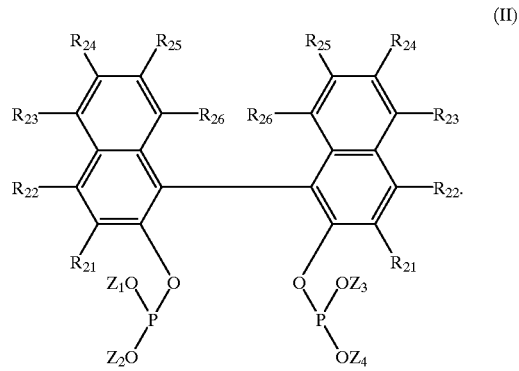
(II)

12. The hydroformylation process according to claim 9, wherein the reaction is carried out in the presence of a bisphosphite compound of the following formula (III):

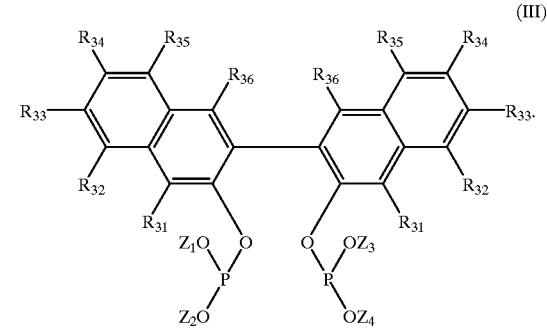
(III)

13. The hydroformylation process according to claim 9, wherein the reaction is carried out in the presence of a bisphosphite compound of the following formula (I):

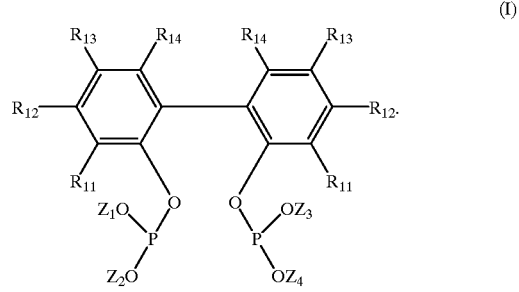
(I)

wherein each $R_{11}$ is a $C_{4-20}$ tertiary alkyl group.

14. The hydroformylation process according to claim 9, wherein the reaction is carried out in the presence of a bisphosphite compound of the following formula (II):

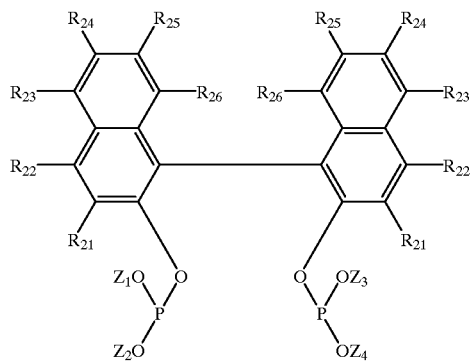
(II)
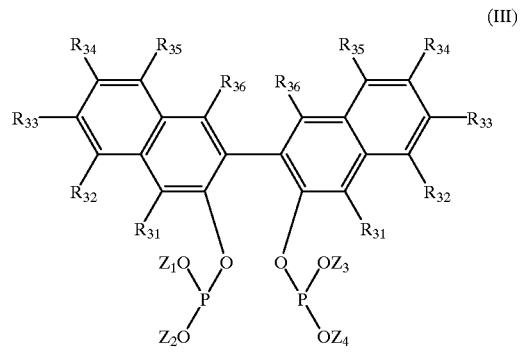
bisphosphite compound of the following formula (III):
(III)
wherein each $R_{21}$ is a $C_{4-20}$ tertiary alkyl group A.
15. The hydroformylation process according to claim 9, wherein the reaction is carried out in the presence of a
wherein each $R_{31}$ is a $C_{4-20}$ tertiary alkyl group (A).
* * * * *